United States Patent
Humes et al.

(10) Patent No.: US 8,425,447 B2
(45) Date of Patent: *Apr. 23, 2013

(54) SELECTIVE CYTOPHERESIS DEVICES AND RELATED METHODS THEREOF

(75) Inventors: H. David Humes, Ann Arbor, MI (US); Deborah Buffington, Ann Arbor, MI (US)

(73) Assignees: The Regents of the University of Michigan, Ann Arbor, MI (US); CytoPherx, Inc., Ann Arbor, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/593,169

(22) Filed: Aug. 23, 2012

(65) Prior Publication Data

US 2012/0322138 A1  Dec. 20, 2012

Related U.S. Application Data

(62) Division of application No. 12/201,576, filed on Aug. 29, 2008, now Pat. No. 8,251, 941.

(60) Provisional application No. 60/969,394, filed on Aug. 31, 2007.

(51) Int. Cl.
*A61M 37/00* (2006.01)

(52) U.S. Cl.
USPC ....... 604/6.03; 604/4.01; 604/5.01; 604/6.01; 604/6.09

(58) Field of Classification Search .......... 604/4.01, 604/5.01, 6.01, 6.03, 5.04, 6.08, 6.07; 210/645
See application file for complete search history.

(56) References Cited

U.S. PATENT DOCUMENTS

| | | | |
|---|---|---|---|
| 3,489,145 | A | 1/1970 | Judson |
| 4,330,410 | A | 5/1982 | Takenaka |
| 4,334,993 | A | 6/1982 | Norton |
| 4,500,309 | A | 2/1985 | Diederich |
| 4,689,191 | A | 8/1987 | Beck |
| 4,980,068 | A | 12/1990 | Lavender |
| 5,032,615 | A | 7/1991 | Ward |
| 5,053,130 | A | 10/1991 | Raff |
| 5,100,564 | A | 3/1992 | Pall |
| 5,104,373 | A | 4/1992 | Davidner et al. |
| 5,147,290 | A | 9/1992 | Jonsson |

(Continued)

FOREIGN PATENT DOCUMENTS

| JP | 10-17493 | 1/1998 |
|---|---|---|
| JP | 10017493 | 1/1998 |

(Continued)

OTHER PUBLICATIONS

Ding, F. et al., "A Novel Selective Cytopheretic Inhibitory Device (SCD) Inhibits Circulating Leukocyte Activation and Ameliorates Multiorgan Dysfunction in a Porcine Model of Septic Shock", J Am Soc Nephrol 19: 2008 pp. 458A.

(Continued)

*Primary Examiner* — Leslie Deak
(74) *Attorney, Agent, or Firm* — Casimir Jones SC

(57) ABSTRACT

The present invention relates to systems and devices to treat and/or prevent inflammatory conditions within a subject and to related methods. More particularly, the invention relates to systems, devices, and related methods that sequester leukocytes and/or platelets and then inhibit their inflammatory action.

27 Claims, 38 Drawing Sheets

U.S. PATENT DOCUMENTS

| | | | |
|---|---|---|---|
| 5,187,102 A | 2/1993 | Stocker et al. | |
| 5,217,627 A | 6/1993 | Pall | |
| 5,229,012 A | 7/1993 | Pall | |
| 5,236,586 A | 8/1993 | Antoni | |
| 5,266,219 A | 11/1993 | Pall | |
| 5,344,561 A | 9/1994 | Pall | |
| 5,383,847 A | 1/1995 | Edelson | |
| 5,486,286 A | 1/1996 | Peterson | |
| 5,501,795 A | 3/1996 | Pall | |
| 5,545,339 A | 8/1996 | Bormann | |
| 5,567,443 A | 10/1996 | Kashiwagi | |
| 5,571,418 A | 11/1996 | Lee | |
| 5,587,070 A | 12/1996 | Pall | |
| 5,601,727 A | 2/1997 | Bormann | |
| 5,616,254 A | 4/1997 | Pall | |
| 5,652,050 A | 7/1997 | Pall | |
| 5,679,264 A | 10/1997 | Gsell | |
| 5,707,526 A | 1/1998 | Kraus | |
| 5,744,047 A | 4/1998 | Gsell et al. | |
| 5,804,079 A | 9/1998 | Brown | |
| 5,830,365 A | 11/1998 | Schneditz | |
| 5,846,419 A | 12/1998 | Nederlof | |
| 5,866,015 A | 2/1999 | Kramer | |
| 5,997,496 A | 12/1999 | Sekiguchi | |
| 6,053,885 A | 4/2000 | Beshel | |
| 6,074,869 A | 6/2000 | Pall | |
| 6,123,859 A | 9/2000 | Lee | |
| 6,231,770 B1 | 5/2001 | Bormann | |
| 6,488,860 B2 | 12/2002 | Mari | |
| 6,498,007 B1 | 12/2002 | Adachi | |
| 6,561,997 B1 | 5/2003 | Weitzel et al. | |
| 6,565,748 B1 | 5/2003 | Wang | |
| 6,566,402 B2 | 5/2003 | Warnock | |
| 6,582,386 B2 | 6/2003 | Min | |
| 6,595,943 B1 | 7/2003 | Burbank | |
| 6,653,131 B2 | 11/2003 | Humes | |
| 6,706,008 B2 | 3/2004 | Vishnoi | |
| 6,730,266 B2 | 5/2004 | Matson | |
| 6,736,972 B1 | 5/2004 | Matson | |
| 6,830,553 B1 | 12/2004 | Burbank | |
| 6,911,007 B2 | 6/2005 | Nier | |
| 6,939,468 B2 | 9/2005 | Wang | |
| 7,125,493 B2 | 10/2006 | Wang | |
| 7,201,730 B2 | 4/2007 | Davidner | |
| 7,297,270 B2 | 11/2007 | Bernard | |
| 7,351,218 B2 | 4/2008 | Bene | |
| 7,410,582 B2 | 8/2008 | Bernard | |
| 7,442,546 B2 | 10/2008 | Humes | |
| 7,524,425 B2 | 4/2009 | Mari | |
| 7,527,737 B2 | 5/2009 | Wang | |
| 7,531,133 B2 | 5/2009 | Hole et al. | |
| 7,591,954 B2 | 9/2009 | Kimura et al. | |
| 7,614,997 B2 | 11/2009 | Bolling | |
| 7,674,235 B2 | 3/2010 | Nier | |
| 7,699,806 B2 | 4/2010 | Ware | |
| 7,799,335 B2 | 9/2010 | Herrmann et al. | |
| 7,829,553 B2 | 11/2010 | Arnold et al. | |
| 7,985,337 B2 | 7/2011 | Heuser | |
| 8,251,941 B2 * | 8/2012 | Humes et al. | 604/6.03 |
| 2002/0107469 A1 | 8/2002 | Bolan et al. | |
| 2005/0143684 A1 | 6/2005 | Bolan | |
| 2005/0215937 A1 | 9/2005 | Spinale | |
| 2005/0281809 A1 | 12/2005 | Roberts | |
| 2007/0014688 A1 | 1/2007 | Hole et al. | |
| 2008/0004712 A1 | 1/2008 | Humes | |
| 2008/0011691 A1 | 1/2008 | Yamada | |
| 2008/0145333 A1 | 6/2008 | Lenz | |
| 2008/0203024 A1 | 8/2008 | Lemke | |
| 2008/0206757 A1 | 8/2008 | Lin | |
| 2008/0260710 A1 | 10/2008 | Kusunoki | |
| 2009/0060890 A1 | 3/2009 | Humes et al. | |
| 2009/0275874 A1 | 11/2009 | Shimagaki | |
| 2009/0324567 A1 | 12/2009 | Spiers | |
| 2010/0266562 A1 | 10/2010 | Humes | |
| 2010/0266563 A1 | 10/2010 | Humes | |
| 2010/0268146 A1 | 10/2010 | Humes | |
| 2010/0268147 A1 | 10/2010 | Humes | |
| 2011/0174733 A1 | 7/2011 | Heinrich | |
| 2011/0196280 A1 | 8/2011 | Humes | |

FOREIGN PATENT DOCUMENTS

| | | |
|---|---|---|
| JP | 2002248165 | 9/2002 |
| JP | 2004243048 | 9/2004 |
| WO | 89/01967 | 3/1989 |
| WO | 93-09783 | 5/1993 |
| WO | 93/24157 | 12/1993 |
| WO | 2007/057065 | 5/2007 |
| WO | 2010/126967 | 4/2010 |

OTHER PUBLICATIONS

Bagshaw, et al., "Is regional citrate superior to systemic heparin anticoagulation for continuous renal replacement therapy? A prospective observational study in an adult regional critical care system", Journal of Critical Care, (2005) 20: pp. 155-161.

Cubattoli, L. et al., "Citrate anticoagulation during CVVH in high risk bleeding patients", The International Journal of Artificial Organs, (2007) 30 (3): pp. 244-252.

Ding, F. et al., "The Effects of a Novel Therapeutic Device on Acute Kidney Injury Outcomes in the Intensive Care Unit: A Pilot Study", ASAIO Journal (2011).

Grooteman, M.P.C. et al., "Hemodialysis-Induced Degranulation of Polymorphonuclear Cells: No Correlation between Membrane Markers and Degranulation Products", Nephron (2000) 85: pp. 267-274.

Hetzel, G. et al., "Regional citrate versus systemic heparin for anticoagulation in critically ill patients on continuous venovenous haemofiltration: a prospective randomized multicentre trial", Nephrol Dial Transplant (2011) 26: pp. 232-239.

Kutsogiannis, D. et al., "Regional citrate versus systemic heparin anticoagulation for continuous renal replacement in critically ill patients", Kidney International (2005) vol. 67, pp. 2361-2367.

Monchi, M. et al., "Citrate vs. heparin for anticoagulation in continuous venovenous hemofiltration: a prospective randomized study", Intensive Care Med (2004) 30: 260-265.

Nurmohamed, S. et al., "Continuous Venovenous Hemofiltration with or without Predilution Regional Citrate Anticoagulation: A Prospective Study", Blood Purif (2007) 25:316-323.

Oudemans-van Straaten, H. et al. "Citrate Anticoagulation for Continuous Renal Replacement Therapy in the Critically Ill" Blood Purif (2010) 29:191-196.

Cruz, D. et al., "The future of extracorporeal support" Crit Care Med (2008) vol. 36, No. 4 (Suppl.) pp. S243-S252.

Oudemans-van Straaten, H. et al., "Citrate Anticoagulation for continuous venovenous hemofiltration" Crit Care Med (2009) vol. 37, No. 2.

Pino, C. et al., "Cardiopulmonary Bypass Surgery Aided by a Selective Cytopheretic Inhibitory Device", ASAIO Bioengineering Abstracts (2011) vol. 57 No. 2 pp. 112.

Ding, F. et al., "A Selective Cytopheretic Inhibitory Device (SCD) Accelerates Renal Recovery and Improves Mortality in ICU Patients with AKI and MOF in an Exploratory Clinical Study", ASAIO Renal Abstracts (2010) vol. 56 No. 2 pp. 140.

Jung, J. et al., "Mechanism of Action of a Selective Cytopheretic Device to Ameliorate Multiorgan Dysfunction in Septic Shock", ASAIO Renal Abstracts (2010) vol. 56 No. 2 pp. 140.

Ding, F. et al., "Central Role of Leukocyte Activation in Acute Kidney Injury and Multiorgan Dysfunction in a Procine Model of Septic Shock", J Am Soc Nephrol (2009) 20: pp. 527A.

Johnston, L. et al., "Integration of a Selective Cytopheretic Inhibitory Device (SCD) into a Protable Sorbent Dialysis System", J Am Soc Nephrol 21: 2010 pp. 363A.

Tumlin, J. et al., "A Multi-Center Pilot Study to Assess the Safety and Efficacy of Selective Cytopheretic Device (SCD) Therapy in Patients with Acute Kidney Injury (AKI)", J Am Soc Nephrol (2011) 22 pp. 24A.

Mehta, R. et al., "A Comparison of Clinical Outcomes between the Selective Cytopheretic Device and Case-Matched historical Controls from the Picard Database", J Am Soc Nephrol (2011) 22 pp. 0127A.

Yevzlin, A. and D. Humes, "Cell Therapy, Advanced Materials, and

New Approaches to Acute Kidney Injury", Hospital Practice, vol. 37:1 (2009) pp. 137-143.

Humes, H. et al., "A Novel Selective Cytopheretic Inhibitory Device (SCD) Improves Mortality in ICU Patients with Acute Kidney Injury (AKI) and Multiorgan Failure (MOF) in a Phase II Clinical Study", J Am Soc Nephrol 19: 2008 pp. 458A.

European Search Report, European Patent Application No. EP 08828222.3, dated Jul. 22, 2011.

Tiranathanagul, K. et al., "Bioartificial kidney in the treatment of acute renal failure associated with sepsis" Nephrology 11, pp. 285-291 (2006).

Yoon, et al., "Spontaneous leukocyte activation and oxygen-free radical generation in end-stage renal disease," Kidney Int 2007;71:167-172 (published online on Nov. 15, 2006).

Humes, H. David, et al., "A Selective Cytopheretic Inhibitory Device to Treat the Immunological Dysregulation of Acute and Chronic Renal Failure," Blood Purification: Published Jan. 8, 2010:29, pp. 183-190.

Ding, Feng, et al., "A Biomimetic Membrane Device That Modulates the Excessive Inflammatory Response to Sepsis," PLoS One, Apr. 2011, vol. 6, Issue 4.

Humes, H. David, et al., "A Selective Cytopheretic Inhibitory Device to Treat the Immunological Dysregulation of Acute and Chronic Renal Failure," Blood Purification, 2010:29, pp. 183-190.

Kidane, Asmeret G., et al., "Anticoagulant and Antiplatelet Agents: Their Clinical and Device Application(s) Together with Usages to Engineer Surfaces," Biomacromolecules 2004, 5, pp. 798-813.

Scholz, Martin, et al., "Fas/FasL Interaction: A Novel Immune Therapy Approach with Immobilized Biologicals," Medicinal Research Review, vol. 25, No. 3, pp. 331-342 (2005).

Wong, Kenneth, et al., "Nitric oxide infusion alleviates cellular activation during preparation, leukofiltration and storage of platelets," Transusion and Apheresis Science 30 (2004), pp. 29-39.

Sutton, SW, et al., "Clinical benefits of continuous leukocyte filtration during cardiopulmonary bypass in patients undergoing valvular repair or replacement," Perfusion (2005); 20:21-29.

International Search Report and Written Opinion, PCT/US2008/074804; mailed Mar. 10, 2009.

Aster, R.H., et a. "Platelet Sequestration in Man. I. Methods," J. Clin. Invest. 43:843-855 (May 1964).

Aster, R.H., et al., "Platelet Sequestration in Man. II. Immunological and Clinical Studies," J. Clin. Invest. 43: 856-869 (May 1964).

Yamaji, Ken, et al., "Current Topics on Cytapheresis Technologies," Therapeutic Apheresis, 5(4):287-292 (2001).

Janatova, J., "Activation and Control of Complement, Inflammation, and Infection Associated with the Use of Biomedical Polymers", ASAIO Journal 2000.

Wang, Song, et al., "Inflammatory response to cardiopulmonary bypass: mechanisms involved and possible therapeutic strategies," Chest, v112.n3 (Sep. 1997): pp676(17); printed Jun. 20, 2007, http://find.galegroup.com/itx/printdoc.do?&prodId=ITOF&userGroupN .
. . .

Itoh, Saotomo, et al., "Platelet activation through interaction with hemodialysis membrances induces neutrophils to produce reactive oxygen specices," published online Jan. 6, 2006 in Wiley InterScience (www.interscience.wiley.corn).

Palanzo, David, A., et al., "Clinical evaluation of the LeukoGuard (LG-6) arterial line filter for routine open-heart surgery," Perfusion 1993; 8:489-496.

Abraham, et al., for the Optimist Trial Study Group: Efficacy and safety of tifacogin (recombinant tissue factor pathway inhibitor) in severe sepsis: a randomized controlled trial. JAMA 390:238-247 (2003).

Alaoja, et al., "Leukocyte filtration to decrease the number of adherent leukocytes in the cerebral microcirculation after a period of deep hypothermic circulatory arrest," J. Thorac Cardiovasc Surg 2006; 132:1339-1347.

Aldea, et al., "Limitation of thrombin generation, platelet activation, and inflammation by elimination of cardiotomy suction in patients undergoing coronary artery bypass grafting treated with heparin-bonded circuits," J Thorac Cardiovasc Surg (2002) 123(4) 742-755.

Andre, P., et al., (2000), "Platelets adhere to and translocate on von Willebrand factor presented by endothelium in stimulated veins," Blood. 96:3322-3328.

Asimakopoulos, et al., "Lung injury and acute respiratory distress syndrome after cardiopulmonary bypass," Ann Thorac Surg (1999) 68(3) 1107-1115.

Balke, et al., "Inhibition of degranulation of human polymorphonuclear leukocytes by complement factor D," FEBS Letters 371 (1995) 300-302.

Bernard, et al., for the Recombinant Human Activated Protein C Worldwide Evaluation in Severe Sepsis (PROWESS) Study Group: Efficacy and safety of recombinant human activated protein C for severe sepsis. N Engl J Med 344: 699-709 (2001).

Bohler, et al., "Mediators of complement-independent granulocyte activation during haemodialysis: role of calcium, prostaglandins and leukotrienes," Nephrology Dialysis Transplantation, 1993, 8:1359-1365.

Bohler, et al., "Reduction of Granulocyte Activation during Hemodialysis with Regional Citrate Anticoagulation: Dissociation of Complement Activation and Neutropenia from Neutrophil Degranulation," J. Am. Soc. Nephrol 7 (2):234-41 (1996).

Bolling, et al., "Prevention of the hypoxic reoxygenation injury with the use of a leukocyte-depleting filter," J. Thorac Cardiovasc Surg 1997;113:1081-1090.

Bologa, et al., "Interleukin-6 predicts hypoalbuminemia, hypocholesterolemia, and mortality in hemodialysis patients," Am J Kidney Dis 1998 3:32:107-114.

Bombeli, et al., (1998), "Adhesion of activated platelets to endothelial cells: evidence for a GPIIblla-dependent bridging mechanism and novel roles for endothelial intercellular adhesion molecule 1 (ICAM-1), alphavbeta3 integrin, and GPIbalpha," J. Exp. Med. 187:329-339.

Bone, et al., "Sepsis, the sepsis syndrome, multi-organ failure: A plea for comparable definitions," Ann Intern Med 114:332-333 (1991).

Bos, et al., "Low polymorphonuclear cell degranulation during citrate anticoagulation: a comparison between citrate and heparin dialysis," Nephrology Dialysis Transplantation, (1997) 12:1387-1393.

Buffington, Deborah H., Abstract of Grant No. 1R43DK074289-01, Project Title: "Cell Therapy for Septic Shock," printed from Computer Retrieval of Information on Scientific Projects on Aug. 29, 2008, 2 pages: http://crisp.cit.nih.gov/crisp/CRISP_LIB.getdoc?textkey=7052152&p_grant_num=1R43DK074289-01&p .
. . .

Buffington, Deborah H., Abstract of Grant No. 1R43DK080529-01, Project Title: "Selective Cytopheresis Therapy in Systemic Inflammatory Response Syndrome," printed from Computer Retrieval of Information on Scientific Projects on Aug. 29, 2008, 2 pages: http://crisp.cit.nih.gov/crisp/CRISP_LIB.getdoc?textkey=7392968&p_grant_num=1R43DK080529-01&p . . . .

Buffington, Deborah H., Abstract of Grant No. 2R44DK074289-03, Project Title: "Cell Therapy for Septic Shock," printed from Computer Retrieval of Information on Scientific Projects on Aug. 29, 2008, 2 pages: http://crisp.citnih.gov/crisp/CRISP_LIB.getdoc?textkey=7536930&p_grant_num=2R44DK074289-03&p .
. . .

Buffington, Deborah H., Abstract of Grant No. 5R43DK074289-02, Project Title: "Cell Therapy for Septic Shock," printed from Computer Retrieval of Information on Scientific Projects on Aug. 29, 2008, 2 pages: http://crisp.cit.nih.gov/crisp/CRISP_LIB.getdoc?textkey=7228623&p_grant_num=5R43DK074289-02&p .
. . .

Carney, et al., "Matrix metalloproteinase inhibitor prevents acute lung injury after cardiopulmonary bypass," Circulation (1999) 100: 400-406.

Chai, et al., "Effects of ischemia on pulmonary dysfunction after cardiopulmonary bypass," Ann Thorac Surg (1999) 67: 731-735.

Chertow, et al., "Mortality after acute renal failure: Models for prognostic stratification and risk adjustment," Kidney International (2006) 70, 1120-1126.

Clark, et al., "Lung injury after cardiopulmonary bypass," Perfusion (2006) 21(4) 225-228.

Coleman, et al., "Leukocyte depletion reduces postoperative oxygen requirements," Ann Thorac Surg (1994) 58:1567-1568.

Deng, et al., "Sepsis-induced suppression of lung innate immunity is mediated by IRAK-M," J Clin Invest 2006: 116:2532-2542.

Dickneite, et al., "Combination of antibiotic treatment with thrombin inhibitor recombinant hirudin for the therapy of experimental *Klebsiella pneumonia* sepsis," Thromb Haemost 71: 768-772 (1994).

Dodd-O, et al., "Effect of NADPH oxidase inhibition on cardiopulmonary bypass-induced lung injury," Am J Physiol Heart Circ Physiol (2004) 287(2) H927-H936.

Eichler, et al., "A rise of MMP-2 and MMP-9 in bronchoalveolar lavage fluid is associated with acute lung injury after cardiopulmonary bypass in a swine model," Perfusion (2003) 18(2) 107-113.

Eichler, et al., "Na/H+ exchange inhibitor cariporide: Effects on respiratory dysfunction after cardiopulmonary bypass," Perfusion (2004) 19(1) 33-40.

El Kebir, "The anti-inflammatory effect of inhaled nitric oxide on poulmonary inflammation in a swine model," Can J Physiol Pharmacol (2005) 83:252-258.

El Kebir, et al., "Effects of inhaled nitric oxide on inflammation and apoptosis after cardiopulmonary bypass," Chest (2005) 128 2910-2917.

Eriksson, et al., Effects of melagatran, a novel direct thrombin inhibitor, during experimental septic shock. Expert Opin Investig Drugs 9:1129Y1137 (2000).

Ferreira, et al., (2001) "Serial evaluation of the SOFA score to predict outcome in critically ill patients," JAMA 286 (14): 1754-8.

Filkins, J., Luzio N: "Heparin protection in endotoxin shock". Am J Physiol 214:1074-1077 (1968).

Fissell, et al., "Bioartificial kidney alters cytokine response and hemodynamics in endotoxin-challenged uremic animals," Blood Purif 2002:20(1):55-60.

Fissell, et al., "Bioartificial kidney ameliorates gram-negative bacteria-induced septic shock in uremic animals," J Am Soc Nephrol 2003:14(2):454-461.

Flanigan, et al., "Reducing the hemorrhagic complication of hemodialysis: A controlled comparison of low-dose heparin and citrate anticoagulation," Am J Kidney Dis 1987:9:147-153.

Frenette, et al., (1998), "Platelet-endothelial interactions in inflamed mesenteric venules," Blood. 91:1318-1324.

Fuhlbrigge, et al., "Sialylated, Fucosylated Ligands for L-Selection Expressed on Leukocytes Mediate Tethering and Rolling Adhesions in Physiologic Flow Conditions," The Journal of Cell Biology, vol. 135, No. 3, pp. 837-848, 1996.

Garrood, et al., "Molecular mechanisms of cell recruitment to inflammatory sites: general and tissue-specific pathways," Rheumatology 2006:45-25-260.

Gritters, et al., "Citrate anticoagulation abolishes degranulationo f polymorphonuclear cells and platelets and reduces oxidative stress during haemodialysis," Nephrology Dialysis Transplantation, 2006, 21:153-159.

Gu, et al., "Leukocyte depletion results in improved lung function and reduced inflammatory response after cardiac surgery," J. Thorac Cardiovasc Surg 1996:112;494-500.

Himmelfarb, et al., "Impaired monocyte cytokine production in critically ill patients with acute renal failure," Kidney Int 66: 2354-2360 (2004).

Himmelfarb, et al., "Plasma aminothiol oxidation in chronic hemodialysis patients," Kidney Int 2002:61(2):705-716.

Himmelfarb, et al., "Plasma protein thiol oxidation and carbonyl formation in chronic renal failure," Kidney Int 2000:58(6):2571-2578.

Horl, et al., "Physicochemical characterization of a polypeptide present in uremic serum that inhibits the biological activity of polymorphonucleear cells," Proc. Natl. Acad. Sci USA, vol. 87, pp. 6353-6357, Aug. 1990.

Humes, et al., "Bioartificial kidney for full renal replacement therapy," Semin Nephrol 2000;20:71-82.

Humes, et al., "Cell therapy with a tissue engineered kidney reduces the multi-organ consequences of septic shock," Crit Care Med 2003:31:2421-2428.

Humes, et al., "Initial clinical results of the bioartificial kidney containing human cells in ICU patients with acute renal failure," Kidney Int 2004:66(4):1578-1588.

Humes, et al., "Metabolic Replacement of Kidney Function of Uremic Animals With a Bioartificial Kidney Containing Human Cells," American Journal of Kidney Diseases, vol. 39, No. 5 (May) 2002, pp. 1078-1087.

Humes, et al., "Renal cell therapy is associated with dynamic and individualized responses in patients with acute renal failure," Blood Purif 21: 64-71 (2003).

Tolwani, et al., "A Practical Citrate Anticoagulation Continuous Venovenous Hemodiafiltration Protocol for Metabolic Control and High Solute Clearance," Clin J Am Soc Nephrol 1:79-87 (2006).

Tschesche, et al., "Inhibition of Degranulation of Polymorphonuclear Leukocytes by Angiogenin and Its Tryptic Fragment" The Journal of Biological Chemistry, vol. 269, No. 48, Dec. 2, 1994, pp. 30274-30280.

Tumlin, et al., "Effect of the Renal Assist Device (RAD) on mortality of dialysis-dependent acute renal failure: A randomized, open-labeled, multicenter. Phase II trial", (abstract). J. Am. Soc. Nephrol 2005:16:46A.

Uchiba, et al., "Effects of various doses of antithrombin III on endotoxin-induced endothelial cell injury and coagulation abnormalities in rats," Thromb Res 89:233-242 (1998).

Vincent, et al., "The SOFA (Sepsis-related Organ Failure Assessment) score to describe organ dysfunction/failure," Intensive Care Med 22:707-710 (1996).

Vincent, Jean-Louis, et al., "Use of the SOFA score to assess the incidence of organ dysfunction/failure in intensive care units: results of a multicenter, prospective study," Critical Care Medicine, Official Journal of the Society of Critical Care Medicine, vol. 26(11), Nov. 1998, 1793-1800.

Wan, et al., "Cytokine responses to cardiopulmonary bypass: Lessons learned from cardiac transplantation," Ann Thorac Surg (1997) 63:269-276.

Wan, et al., "Inflammatory response to cardiopulmonary bypass: Mechanisms involved and possible therapeutic strategies," Chest (1997) 112(3) 676-693.

Warren, et al., High-dose antithrombin III in severe sepsis: a randomized controlled trial. JAMA 286: 1869-1878 (2001).

Wiegmann, et al., "Dialysis Leukopenia, Hypoxemia, and Anaphylatoxin Formation: Effect of Membrane, Bath, and Citrate Anticoagulation," American Journal of Kidney Diseases, vol. XI, No. 5 May 1988, pp. 418-424.

Wiegmann, et al., "Long term comparisons of citrate and heparin as anticoagulants for hemodialysis," Am J Kidney Dis 1987:9:420-435.

Williams, et al., "RAD-002 Study Investigators. Renal bioreplacement therapy (RBT) reduces mortality in ICU patients with acute renal failure (ARF)," (abstract) J Am Soc Nephrol 2006:17:49A.

Xue, at al., "Forecast of the number of patients with end-stage renal disease in the United States to the year 2010," J Am Soc Nephrol (2001) 12:2758-2763.

Ympa, et al., "Has mortality from acute renal failure decreased? A systematic review of the literature," Am. J. Med., 118:827-832 (2005).

Yoon, et al., "Spontaneous leukocyte activation and oxygen-free radical generation in end-stage renal disease," Kidney Int 2007:71:167-172.

Zarbock, et al., (2006), "Complete reversal of add-induced acute lung injury by blocking of platelet-neutrophil aggregation," J. Clin. Inv. 116:3211-3219.

Zehr, et al., "Platelet activating factor inhibition reduces lung injury after cardiopulmonary bypass," Ann Thorac Surg (1995) 59(2) 328-335.

Zelen, M., "The randomization and stratification of patients to clinical trials," J Chronic Dis 27: 365-375 (1974).

Zimmerman, et al., "Inflammation enhances cardiovascular risk and mortality in hemodialysis patients," Kidney Int 1999:55:648-658.

Humes, et al., "Replacement of renal function in uremic animals with a tissue-engineered kidney," Nature Biotechnology, vol. 17, May 1999, pp. 451-455.

Humes, et al., "The bioartificial kidney in the treatment of acute renal failure," Kidney Int 2002:61(Suppl 80):S121- S125.

Humes, et al., Tissue engineering of a bioartificial renal tubule assist device; in vitro transport and metabolic characteristics. Kidney Int 1999:55(6):2502-2514.
Jansen, et al., "Endotoxin release and tumor necrosis factor formation during cardiopulmonary bypass," Ann Thorac Surg (1992) 54: 744-748.
Kaneider NC, et al., "Therapeutic targeting of molecules involved in leukocyte-endothelial cell interactions," FEBS J 2006:273:4416-4424.
Kaplow and Goffinet, "Profound Neutropenia During the Early Phase of Hemodialysis," JAMA, Mar. 25, 1968, vol. 203, No. 13.
Kelly, KJ, "Acute renal failure: Much more than a kidney disease," Semin Nephrol 26: 105-113 (2006).
Kim, et al., "The relative role of the Child-Pugh classification and the Mayo natural history model in the assessment of survival in patients with primary sclerosing cholangitis," Hepatology 29: 1643-1648 (1999).
Kimmel, et al., "Immunologic function and survival in hemodialysis patients," Kidney Int 1998:54:236-244.
Knaus, et al., "Apache II: A severity of disease classification system," Crit Care Med 13(10):818-829 (1985).
Koster, et al., "The more closed the bypass system the better. A pilot study on the effects of reduction of cardiotomy suction and passive venting on hemostatic activation during on-pump coronary artery bypass grafting," Perfusion (2005) 20(5) 285-288.
Lake, et al., "Acute renal failure: Directed therapy to enhance renal tubular regeneration," Semin Nephrol 14:83-97 (1994).
Lohr, et al., "Safety of regional citrate hemodialysis in acute renal failure," Am J Kidney Dis 1989:13:104-107.
Lopes, et al., "Serial Evaluation of the SOFA Score to Predict Outcome in Critically Ill Patients," JAMA, Oct. 10, 2001, vol. 286, No. 14.
Marosznska, et al., "Leukocytes and endothelium interaction as rate limiting step in the inflammatory response and a key factor in the ischemia-reperfusion injury," Ann Transplant 2000:5(4):5-11.
Mehta, et al., "Spectrum of acute renal failure in the intensive care unit: The PICARD experience," Kidney Int 66:1613-1621 (2004).
Messent, et al., "Adult respiratory distress syndrome following cardiopulmonary bypass: Incidence and prediction," Anaesthesia (1992) 47: 267-268.
Meyer, et al., "Heparin in experimental hyperdynamic sepsis," Crit Care Med 21: 84-89 (1993).
Miller: Miller's Anesthesia, 6th ed., "Anticoagulation for CPB," 4 pages, printed on Aug. 23, 2007, http://www.mdconsult.com/das/book/body/76819015-2/0/1255/1438.html?tocnode=53063 . . . .
Miller: Miller's Anesthesia, 6th ed., "Cardiopulmonary Bypass,", 2 pages, printed on Aug. 23, 2007, http://www.mdconsult.com/das/book/body/76818435-2/0/1255/1437.html?tocnode=53063 . . . .
Miller: Miller's Anesthesia, 6th ed., "Common Problems After Cardiopulmonary Bypass," 5 pages, printed on Aug. 23, 2007, http://www.mdconsult.com/das/book/body/76819015-2/0/1255/1445.html?tocnode=53063 . . . .
Miller: Millers Anesthesia, 6th ed., "Heparin Reversal," 2 pages, printed on Aug. 23, 2007, http://www.mdconsult.com/das/book/body/76819015-2/0/1255/1444.html?tocnode=53063 . . . .
Miller: Miller's Anesthesia, 6th ed., "Management of CPB," 6 pages, printed on Aug. 23, 2007, http://www.mdconsult.com/das/book/body/76819015-2/0/1255/1442.html?tocnode=53063 . . . .
Miller: Miller's Anesthesia, 6th ed., "Pathobiology of CPB", 4 pages, printed on Aug. 23, 2007, http://www.mdconsult.com/das/bookbody/76819015-2/0/1255/1440.html?tocnode=53063 . . . .
Miller: Miller's Anesthesia, 6th ed., "Separation From CBP," 2 pages, printed on Aug. 23, 2007, http://www.mdconsult.com/das/book/body/76819015-2/0/1255/1255.html?tocnode=53063 . . . .
Mishra, et al., "Neutrophil gelatinase-associated lipocalin (NGAL) as a biomarker for acute renal injury after cardiac surgery," Lancet (2005) 365(9466) 1231-1238.
Morioka, et al., "Leukocyte and platelet depletion with a blood cell separator: Effects on lung injury after cardiac surgery with cardiopulmonary bypass," J Thorac Cardiovasc Surg (1996) 111(1) 45-54.
Nakamura, et al., "Ceramide Regulates Oxidant Release in Adherent Human Neutrophils," The Journal of Biological Chemistry, vol. 269, No. 28, Issue of Jul. 15, pp. 18384-18389 (1994).
Parikh, et al., "Urinary IL-18 is an early predictive biomarker of acute kidney injury after cardiac surgery," Kidney Int (2006) 70(1) 199-203.
Pennathur, et al., "A hydroxyl radical-like species oxidizes cynomologus monkey artery wall proteins in early diabetic vascular disease," J Clin Invest 2001:107:853-860.
Pennathur, et al., "Mechanisms of oxidative stress in diabetes: Implications for the pathogenesis of vascular disease and antioxidant therapy," Front Biosci 2004:9:565-574.
Picone, et al., "Multiple sequential insults cause post-pump syndrome," Ann Thorac Surg (1999) 67(4) 978-985.
Pinnick, et al., "Regional citrate anticoagulation for hemodialysis in the patient at high risk for bleeding," N Engl J Med 1983:266:372-377.
Rabb, et al., "Acute renal failure leads to dysregulation of lung salt and water channels," Kidney Int 63: 600-606 (2003).
Rinder, et al., (1991), "Activated and unactivated platelet adhesion to monocytes and neutrophils," Blood. 78:1760-1769.
Romo, et al., (1999) "The glycoprotein ib-IX-V complex is a platelet counterrecptor for P-selectin," J Exp Med 190: 803-814.
Salem and Mujais, Dialysis Therapy, Second Edition, Chapter 5, Dialyzers; Editors: Nissensen and Fine, Hanley & Belfus, Inc., Philadelphia, PA. 1993, pp. 65-77.
Sawa, et al., "Evaluation of leukocyte-depleted terminal blood cardioplegic solution in patients undergoing elective and emergency artery bypass grafting," J Thorac Cardiovasc Surg (1994) 108: 1125-1131.
Schiffer, et al., "Evaluation of unfractionated heparin and recombinant hirudin on survival in a sustained ovine endotoxin shock model," Crit Care Med 30:2689-2699 (2002).
Sela, et al., "Primed peripheral polymorphonuclear leukocyte: A culprit underlying chronic low-grade inflammation and systemic oxidative stress in chronic kidney disease," J. Am Soc Nephrol 2005:16:2431-2438.
Simmons, et al., "Plasma cytokine levels predict mortality in patients with acute renal failure," Kidney Int 65: 1357-1365 (2004).
Sutton, et al., "Microvascular endothelial injury and dysfunction during ischemic acute renal failure," Kidney Int 62:539-549 (2002).
Takashi, et al., "A Peptide Against the N-Terminus of Myristoylated Alanine-Rich C Kinase Substrate Inhibits Degranulation of Human Leukocytes In Vitro," Am J Respir Cell Mol Biol, vol. 34, pp. 647-652, 2006.
Tang, et al., "Leukodepletion reduces renal injury in coronary revascularization: A prospective randomized study." Ann Thorac Surg 2002; 74:372-377.
Taylor, et al., "Antithrombin III prevents the lethal effects of *Escherichia coli* infusion in baboons," Circ Shock 26: 227-235 (1988).
Teasdale, et al., "Assessment of coma and impaired consciousness. A practical scale," Lancet 2(7872): 81-84 (1974).
Tevaearai, et al., "In situ control of cardiotomy suction reduces blood trauma," ASAIO J (1998) 44(5): M380-M383.
Thakar, et al., "Renal dysfunction and serious infections after open-heart surgery," Kidney Int 2003:64:239-246.
Tielemans, et al., "Adhesion molecules and leukocyte common antigen on monocytes and granulocytes during hemodialysis," Clinical Nephrology, vol. 39, No. 3, 1993 (158-165).
Tobe, et al., "A Novel Regional Citrate Anticoagulation Protocol for CRRT Using Only Commercially Available Solutions," Journal of Critical Care, vol. 18, No. 2 (Jun.) 2003, pp. 121-129.
Humes et al., (Oct. 10, 2012), "Immunomodulation with a Selective Cytopheretic Device (SCD) Improves Myocardial Contractility and Renal Sodium Excretion in a Canine Model of Congestive Heart Failure," J. Am. Soc. Nephrol., 23(Abstract Supplement): AbstractTH-OR015.
Pino et al., (Apr. 16, 2012), "A Selective Cytopheretic Inhibitory Device (SCD) for use during Cardiopulmonary Bypass Surgery," Perfusion, 27(4):311-9.

* cited by examiner

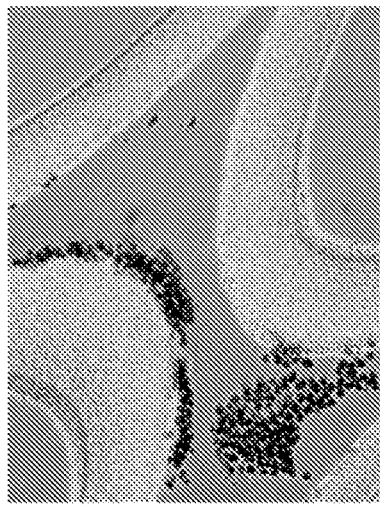
FIG. 14B
FIG. 14A
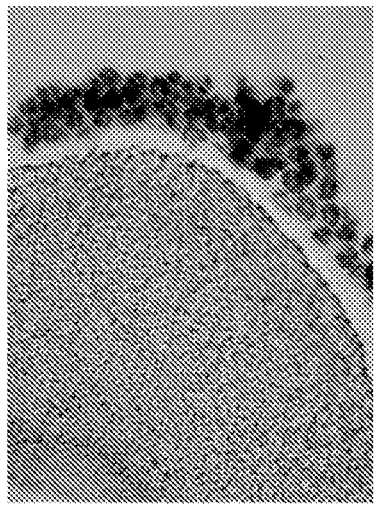
FIG. 14D
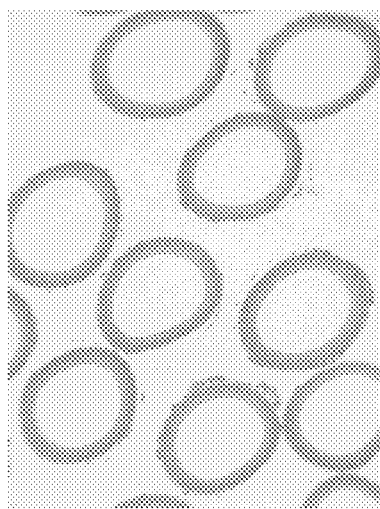
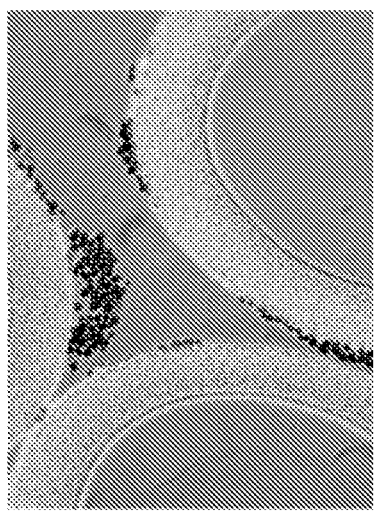
FIG. 14C

```
SEQUENCE LISTING

<160> NUMBER OF SEQ ID NOS: 1

<210> SEQ ID NO 1
<211> LENGTH: 149
<212> TYPE: PRT
<213> ORGANISM: Artificial Sequence
<220> FEATURE:
<223> OTHER INFORMATION: Synthetic

<400> SEQUENCE: 1

Leu His Gly Gly Ser Pro Trp Pro Pro Cys Cys Cys Cys Cys Cys
1               5                   10                  15

Cys Cys Cys Cys Cys Cys Cys Cys Cys Cys Cys Cys Cys Cys Cys
                20                  25                  30

Cys Cys Cys Cys Cys Cys Cys Cys Cys Cys Cys Cys Cys Cys Cys
            35                  40                  45

Cys Cys Cys Cys Cys Cys Cys Cys Cys Cys Cys Cys Cys Cys Cys
        50                  55                  60

Cys Cys Cys Cys Cys Cys Cys Cys Cys Cys Cys Cys Cys Cys Cys
65                  70                  75                  80

Cys Cys Cys Cys Cys Cys Cys Cys Cys Cys Cys Cys Cys Cys Cys
                85                  90                  95

Cys Cys Cys Cys Cys Gln Tyr Arg Gly Leu Thr Ser Pro Cys Cys Cys
                100                 105                 110

Cys Cys Cys Cys Cys Cys Cys Cys Cys Cys Cys Cys Cys Cys Cys
            115                 120                 125

Cys Cys Cys Cys Cys Cys Cys Cys Cys Cys Cys Cys Cys Cys Cys
        130                 135                 140

Cys Cys Cys Cys Lys
145
```

SELECTIVE CYTOPHERESIS DEVICES AND RELATED METHODS THEREOF

RELATED APPLICATIONS

This application is a divisional of U.S. patent application Ser. No. 12/201,576, filed Aug. 29, 2008, which claims the benefit of and priority to U.S. Provisional Patent Application No. 60/969,394, filed Aug. 31, 2007, the entire disclosures of each of which are incorporated by reference herein.

STATEMENT REGARDING FEDERALLY SPONSORED RESEARCH OR DEVELOPMENT

This invention was made with government support under Grant Nos. DK080529 and DK074289 awarded by the National Institutes of Health. The government has certain rights in this invention.

SEQUENCE LISTING

Please incorporate the sequence listing filed herewith as a text filed entitled "14567-US-11-DIV_ST25.txt".

FIELD OF THE INVENTION

The present invention relates to systems, devices, and methods to treat and/or prevent inflammatory conditions within a subject. More particularly, the present invention relates to systems, devices, and related methods that sequester cells associated with inflammation, such as leukocytes and platelets, and then reduce their inflammatory activity.

BACKGROUND

Various medical conditions are caused, exacerbated, and/or characterized by unwanted inflammation. Infections, such as bacterial, viral, and fungal infections; trauma, such as from falls, automobile accidents, gun and knife wounds; cardiovascular events, such as aneurysms and ischemic events often associated with surgery; and endogenous inflammatory reactions, such as pancreatitis and nephritis, often lead to profound dysfunction of the homeostatic mechanisms involved in regulating cardiovascular and immune system function. Several of these conditions, such as ischemia and infections, through abnormal or excessive activation of the immune system, may result in cardiovascular dysfunction that can develop over a period of hours to days, and which, under certain circumstances, can be life threatening or even fatal.

Certain cell types are critical to the dysfunction of the cardiovascular and immune systems. For example, leukocytes, especially neutrophils, contribute to the pathogenesis and progression of various inflammatory conditions, including systemic inflammatory response syndrome (SIRS), sepsis, ischemia/reperfusion injury and ARDS (see, e.g., Kaneider et al. (2006) FEBS J 273:4416-4424; Maroszynska et al. (2000) Ann. Transplant. 5(4):5-11). In addition, activated platelets enhance leukocyte adhesion and promote leukocyte activation. While inflammation and a systemic immune response can be beneficial in certain circumstances, they can also be fatal.

Inflammatory injury in organs can result in microvascular damage induced by leukocyte activation and aggregation, as well as platelet activation and aggregation. These activated cells can contribute to microvascular stasis and reperfusion injury by releasing toxic compounds into a patient's tissue. In acute inflammation, activated leukocytes and platelets interact as a gel-like structure within the vessel. This leads to poor perfusion of the tissue, which normally is supplied with oxygen and nutrients by the capillaries. Activated leukocytes additionally cause damage by extravasating across the endothelium into the tissue, where they release toxic agents normally intended to destroy invading microbes or clear out necrotic debris. Activated platelets additionally cause damage by enhancing the activation and endothelial transmigration of leukocytes. When these processes are not controlled, they can lead to tissue injury and death.

SIRS is the thirteenth leading cause of death in the United States of America. Severe sepsis with SIRS occurs in 200,000 patients annually in the U.S. with a mortality rate of 30-40%, even with use of intensive care units and broad spectrum antibiotics. SIRS is diagnosed largely on observed physiological changes such as increase (fever) or decrease (hypothermia) in body temperature, increased heart rate (tachycardia), increased respiration rate (tachypnea), elevated or diminished white blood cell counts, and inadequate perfusion of tissues and organs. A decrease in blood pressure is a complication associated with SIRS that occurs late in the course of the syndrome. Specifically, a decrease in blood pressure can reflect the development of shock and contribute to multiple organ failure, which is a leading cause of death in these patients. Septic shock is a condition that includes the clinical observations of the presence of an infection and a drop in blood pressure despite fluid resuscitation and proper cardiac blood output. A similar condition, sepsis syndrome, includes similar physiological signals with no evidence of any type of infection. Other insults, which induce a sepsis-like condition include pancreatitis, burns, ischemia, multiple trauma and tissue injury (often due to surgeries and transplants), haemorrhagic shock and immune-mediated organ dysfunction.

The standard therapies for SIRS and septic shock involve administration of antibiotics to bring the infection under control and fluid/colloid therapy to maintain circulating blood volume. Frequently, drugs that help maintain blood pressure, such as dopamine and vasopressin, are also administered.

Cardiopulmonary bypass (CPB) strongly induces SIRS, activating complement and coagulation systems and stimulating cytokine production. A large number of therapeutic approaches are under investigation to limit the activation and accumulation of leukocytes during CPB. In fact, animal and early clinical data suggest amelioration of lung and kidney damage during CPB surgery with the use of leukocyte depletion filters (see, e.g., Gu et al. (1996) J. Thorac. Cardiovasc. Surg. 112:494-500; Bolling et al. (1997) J. Thorac. Cardiovasc. Surg. 113:1081-1090; Tang et al. (2002) Ann. Thorac. Surg. 74:372-377; Alaoja et al. (2006) J. Thorac. Cardiovasc. Surg. 132:1339-1347). It appears, however, that dialysis can produce transient neutropenia (see Kaplow et al. (1968) *JAMA* 203:1135).

Recent strategies for developing more targeted therapies for the treatment of sepsis have been disappointing. In addition, many molecules in the new generation of anti-septic agents are very expensive and can produce adverse immunological and cardiovascular reactions, which make them contra-indicated in some cases, such as non-bacteremic shock.

There remains a need for an effective treatment of inflammatory conditions, such as, cardiovascular shock, sepsis, systemic inflammatory response syndrome and anaphylaxis.

SUMMARY OF THE INVENTION

An inflammatory condition in a subject arises, in part, from the activation of cells associated with inflammation, such as leukocytes and platelets. The present invention relates to systems, devices, and methods to treat and/or prevent this condition by sequestering leukocytes or platelets and inhibiting or deactivating their inflammatory action. The systems, devices, and methods of the invention extracorporeally sequester one or both of leukocytes and platelets and inhibit their inflammatory actions. For example, these cells can be deactivated and/or their release of pro-inflammatory substances can be inhibited. Although there are many ways to practice the invention, one approach is to sequester one or both of leukocytes and platelets in the interior of a device providing a surface with which these cells may associate, and providing an agent capable of deactivating the cells and/or inhibiting the release of a pro-inflammatory substance. In one, non-limiting embodiment, the device contains hollow fibers and the cells associate with the exterior of these fibers. Citrate is provided to deactivate the cells and/or prevent the release of a pro-inflammatory substance. Experiments conducted using this and other embodiments of the present invention provide unprecedented and surprising success in maximizing subject survival. These results exemplify the compelling utility of the systems, devices, and methods of the invention across a range of inflammatory diseases and conditions.

Accordingly, in one aspect, the invention provides a system for treating leukocytes that includes a device defining a passageway that permits a biological sample to flow therethrough and comprising a region configured to sequester one or more leukocytes originating from the sample. The system also includes an agent capable of inhibiting the release of a pro-inflammatory substance from the leukocyte or deactivating the leukocyte.

This aspect of the invention can have one or more of the following features. The leukocyte can be activated and/or primed. The system can further include a second device in series with the device defining the passageway. The agent can be associated with a surface of the passageway. In certain circumstances, the agent can be infused into the passageway. The agent can comprise an immunosuppressant, a serine leukocyte inhibitor, nitric oxide, a polymorphonuclear leukocyte inhibitor factor, a secretory leukocyte inhibitor, and a calcium chelating agent, wherein the calcium chelating agent can be citrate, sodium hexametaphosphate, ethylene diamine tetra-acetic acid (EDTA), triethylene tetramine, diethylene triamine, o-phenanthroline, or oxalic acid. However, the agent preferably is a calcium chelating agent, such as citrate.

The region configured to sequester the leukocyte can include a membrane. The membrane can be porous, semi-porous, or non-porous and/or the membrane can have a surface area greater than about 0.2 m$^2$. The region configured to sequester the leukocyte can be configured such that the shear force within the region is sufficiently low to allow the leukocyte to remain in the region longer than another component of the blood or fluid. For example, the shear force within the region configured to sequester the leukocyte can be less than about 1000 dynes/cm$^2$. Alternatively and/or in conjunction, the region configured to sequester the leukocyte can comprise a cell-adhesion molecule to allow the leukocyte to remain in the region longer than another component of the blood or fluid.

In another aspect, the invention provides a method for processing a leukocyte contained within a body fluid. The method includes (a) sequestering extracorporeally a primed or activated leukocyte, and (b) treating the leukocyte to inhibit the release of a pro-inflammatory substance from the leukocyte and/or deactivate the leukocyte. This aspect of the invention can have one or more of the following features. The leukocyte can be sequestered for a time sufficient to inhibit release of the pro-inflammatory substance from the leukocyte and/or deactivate the leukocyte, and/or for a prolonged period of time, and/or for at least one hour. The method can further comprise the step of returning the leukocyte produced in step (b) back to a subject. In step (b), a calcium chelating agent can be used to inhibit release of the pro-inflammatory substance and/or deactivate the leukocyte. Step (a) can be performed using a device defining a passageway that comprises a region configured to sequester the leukocyte.

In another aspect, the invention provides a method for treating a subject at risk of developing or having an inflammatory condition. The method comprises (a) sequestering extracorporeally a primed or activated leukocyte from the subject and (b) treating the leukocyte to reduce the risk of developing inflammation associated with the inflammatory condition or to alleviate inflammation associated with the inflammatory condition. The inflammatory conditions that this method can treat include, but are not limited to, systemic inflammatory response syndrome (SIRS), cardiopulmonary bypass syndrome, acute respiratory distress syndrome (ARDS), sepsis, rheumatoid arthritis, systemic lupus erythematosis, inflammatory bowel disease, multiple sclerosis, psoriasis, allograft rejection, asthma, chronic renal failure, cardiorenal syndrome, hepatorenal syndrome, acute organ failure from ischemic reperfusion injury to myocardium, central nervous system, liver, kidney, or pancreas, and acute organ failure due to toxic injury, for example, chemotherapy. Step (a) can be performed using a device defining a passageway, which comprises a region configured to sequester the leukocyte.

The systems, devices, and methods of the present invention are not limited to a particular type or kind of leukocyte inhibiting agent. In some embodiments, the leukocyte inhibiting agent is any agent that is able to inhibit release of a pro-inflammatory substance from the leukocyte and/or deactivate the leukocyte. Examples of leukocyte inhibiting agents include, but are not limited to, immunosuppressants, serine leukocyte inhibitors, nitric oxide, polymorphonuclear leukocyte inhibitor factor, and secretory leukocyte inhibitor. In some embodiments, the leukocyte inhibiting agent is a calcium chelating agent (e.g., citrate). The present invention is not limited to a particular type or kind of calcium chelating agent, which include, but are not limited to, citrate, sodium hexametaphosphate, ethylene diamine tetra-acetic acid (EDTA), triethylene tetramine, diethylene triamine, o-phenanthroline, oxalic acid and the like.

It is understood that any of the above-identified aspects or embodiments of the present invention can be equally applied to the sequestration and deactivation or inhibition of platelets (e.g., activated platelets), the combination of leukocytes and platelets, or cells associated with inflammation. Accordingly, in another aspect, the invention provides a method for treating a subject at risk of developing or having an inflammatory condition. The method comprises (a) selectively sequestering extracorporeally a primed or activated cell associated with inflammation from the subject; and (b) treating the cell to reduce the risk of developing inflammation associated with the inflammatory condition or to alleviate inflammation associated with the inflammatory condition. In some embodiments, the activated cell associated with inflammation can be selected from the group consisting of a platelet and a leukocyte. In some embodiments, the primed cell associated with inflammation is a leukocyte.

It should be understood that different embodiments of the invention, including those described under different aspects of the invention, are meant to be generally applicable to all aspects of the invention. Any embodiment may be combined with any other embodiment unless inappropriate. All examples are illustrative and non-limiting.

BRIEF DESCRIPTION OF THE DRAWINGS

The foregoing aspects and embodiments of the invention may be more fully understood by reference to the following detailed description and claims.

In FIGS. 4A-4C, blood treated by a SCID 555 with the ICS capped at both ends (FIGS. 4A and 4B), or by a SCID 655 with one end capped, is recirculated into the portion of the circuit prior to the venous reservoir 450 and oxygenator 460. In FIGS. 4D-4F, blood treated by a SCID 555 with the ICS capped at both ends is recombined with blood in the portion of the circuit following the oxygenator 460. HF/HC represents a hemofilter/hemoconcentrator, P represents a pump 504, and UF represents a reservoir to collect ultrafiltrate.

FIGS. 14A-14D show light micrographs of a SCID containing hollow fiber membranes stained with H&E from three different animals. FIG. 14A is a low power micrograph showing adherent cells around each hollow fiber (160×). FIGS. 14B and 14C are higher power micrographs demonstrating leukocyte clustering along the outer surface of hollow fibers (400×). FIG. 14D is a high-power micrograph displaying predominantly polymorphonuclear cells along with mononuclear cells in the adherent cell clusters (1600×).

DETAILED DESCRIPTION

Figure 1:
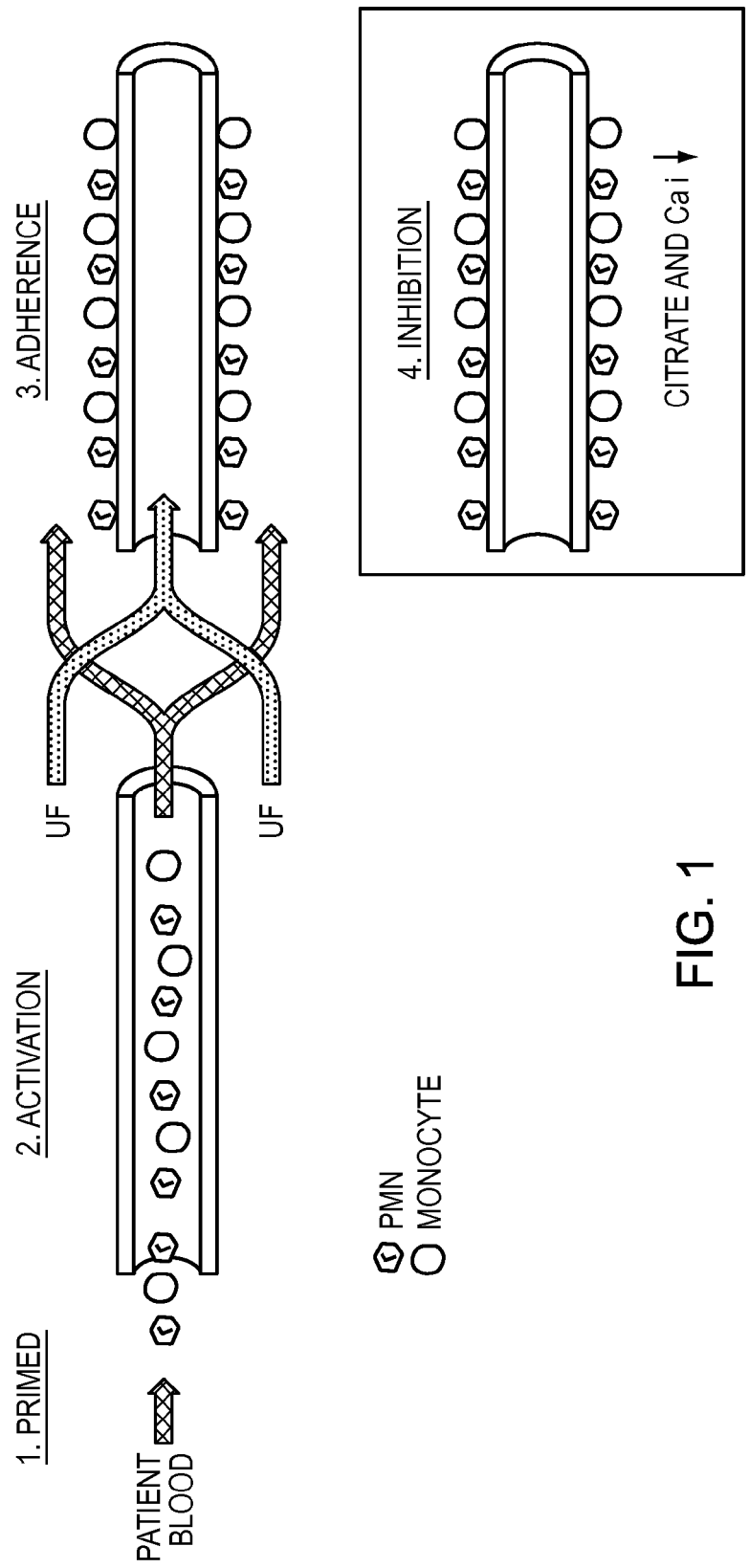
FIG. 1 is a schematic diagram of a section of an exemplary embodiment of devices in a system of the invention. In the Figure, (1) primed leukocytes from a subject's blood are (2) activated by an upstream device in the system, for example, a hemofiltration device. In the upstream device, blood flows through the internal space of a hollow chamber and ultrafiltrate (UF) is filtered through the wall of the chamber. Upon exiting the first device, blood then flows inside a second device, for example, a selective cytopheresis inhibitory device (SCID), along the outside of hollow fibers, while UF flows through the internal space of the hollow fibers. The blood flowing along the outside of the hollow fibers is exposed to conditions (3) that permit leukocytes in the blood to be sequestered, for example, by adhering to the external surface of the hollow fibers, thereby facilitating (4) inhibition of release of a pro-inflammatory substance from the leukocytes and/or deactivation of the leukocytes with a leukocyte inhibiting agent, for example, citrate, which decreases ionized calcium ($Ca_i$).

Cells associated with inflammation, such as leukocytes (or white blood cells) and platelets, normally defend the body against infection and injury. However, many disease states and medical procedures can activate and/or prime these cells, which in turn can produce undesirable immune and inflammatory responses that can be fatal. The present invention relates to systems and devices configured to treat and/or prevent inflammatory conditions within a subject, and related methods. The systems, devices, and methods of the invention extracorporeally sequester one or both of leukocytes and platelets and inhibit their inflammatory actions. Specifically, the present invention includes systems, devices, and methods for sequestering leukocytes, such as activated and/or primed leukocytes, and inhibiting release of a pro-inflammatory substance from the leukocytes and/or deactivating the leukocytes, before returning them to the subject. The present invention also includes systems, devices, and methods for sequestering other types of cells associated with inflammation, such as platelets (e.g., activated platelets) and inhibiting release of a pro-inflammatory substance from these cells, before returning them to the subject.

Although there are many ways to practice the invention, one way is to sequester one or both of leukocytes and platelets in the interior of a device that provides a surface with which these cells may associate and to provide an agent capable of deactivating the cells and/or inhibiting release of a pro-inflammatory substance. In one, non-limiting embodiment, the device contains hollow fibers, and the cells associate with the exterior of these fibers. Citrate is provided to deactivate the cells and/or prevent the release of a pro-inflammatory substance. Although the invention is described herein with regard to blood, the invention is applicable to any biological sample that can flow through an extracorporeal circuit, such as any fluid from a subject's body containing these cells. Exemplary extracorporeal circuits are described, for example, in U.S. Pat. No. 6,561,997.

1. Overview

The systems, devices, and methods of the present invention arose from the unexpected observation that particular device and system configurations not only can sequester activated and/or primed leukocytes but also can inhibit their inflammatory activity, thereby reducing the multi-organ effects of inflammatory diseases and conditions, such as sepsis and SIRS. These acute effects may also have an influence on chronic pro-inflammatory states, such as the chronic pro-inflammatory state associated with end stage renal disease (ESRD). These systems, devices, and methods also showed effective sequestration of platelets. Experiments conducted using embodiments of the present invention provide unprecedented and surprising success in maximizing a subject's survival (see, for example, Example 3) and exemplify the compelling utility of these systems, devices, and methods across a range of diseases and conditions for therapeutic, diagnostic, and research applications.

A schematic representation of one exemplary embodiment is shown in FIG. 1. As shown, blood is exposed to a first device. Thereafter, the leukocytes become activated (and/or primed). The activated (and/or primed) leukocytes then enter a device, generally referred to as a selective cytopheresis inhibitory device (SCID), wherein the activated leukocytes are sequestered. It is understood that rather than being activated by a first device, the leukocytes may be activated (and/or primed) as a result of a primary patient condition or secondary to other types of medical intervention.

In other words, in the SCID, the activated (and/or primed) leukocytes from the blood are sequestered, for example, by temporarily adhering to one or more surfaces inside the SCID. Sequestration of the leukocytes can be achieved by a variety of approaches, for example, by association with molecules in a passageway or passageway region in the SCID that bind leukocytes, for example, activated and/or primed leukocytes, or by setting blood flow within the device to provide low shear stress on leukocytes, allowing them to associate with one or more surfaces inside the SCID. These sequestered leukocytes then are exposed to an agent, for example, citrate, to deactivate the leukocytes or inhibit their release of pro-inflammatory substances. These systems and devices also can apply to other cell types, such as platelets.

Without being bound by theory, it is believed that calcium chelators, for example, citrate, lead to a low $Ca_i$ environment in the device, inhibiting release of a pro-inflammatory substance from the leukocytes and/or deactivating the leukocytes. Pro-inflammatory substances may include destructive enzymes and/or cytokines from the leukocytes. This inhibition and/or deactivation leads to an amelioration of the inflammatory state of the leukocytes. In this way, in the exemplary embodiment shown in FIG. 1 (and other embodiments of the invention), the SCID sequesters leukocytes, for example, neutrophils and monocytes, and inhibits release of a pro-inflammatory substance from the leukocytes and/or deactivates the leukocytes, for example, with citrate and/or a low-$Ca_i$ environment. The sequestration and inhibition and/or deactivation of platelets can be achieved in a similar fashion.

It has been demonstrated that the addition of a calcium chelator, e.g. citrate, to a device of the present invention including a housing containing hollow fibers that sequester leukocytes had the unexpected result of improving a subject's innate immunologic system. Accordingly, the systems, devices, and methods of the present invention can treat or prevent a variety of inflammatory conditions (either as primary disease states or as a result of medical intervention) by directly treating a subject's blood that includes leukocytes (e.g., activated and/or primed leukocytes) or platelets (e.g., activated platelets). Following treatment, the blood is returned to the subject.

Moreover, any method, device, or system that sequesters leukocytes or platelets (such as activated leukocytes, primed leukocytes, or activated platelets) and deactivates such cells or prevents such cells from releasing a pro-inflammatory substance can be used. Accordingly, the following sections describe (1) configurations of systems that may be used to treat an inflammatory condition, (2) examples of how cells associated with inflammation can be sequestered, (3) examples of how such cells can be deactivated and/or inhibited from releasing a pro-inflammatory substance, and (4) the inflammatory conditions that can be treated using the methods, devices, and systems described herein. While the discussion in the sections that follow generally describe sequestration and inhibition and/or deactivation of a particular cell type (e.g., leukocytes), it is understood that the same principles apply to the sequestration and inhibition and/or deactivation of other cell types associated with inflammation (e.g., platelets, such as activated platelets).

2. System Configurations

As used herein, the term "cytopheresis" or "selective cytopheresis" refers to the sequestration of certain particles from blood. Selective cytopheresis is used to sequester certain cells, such as leukocytes (e.g., activated and/or primed leukocytes) or platelets (e.g., activated platelets) from blood for purposes of facilitating inhibition of release of a pro-inflammatory substance from such cells and/or deactivation of such cells. It should be understood that such inhibition and/or deactivation can occur before, during, and/or after sequestration.

"Selective cytopheresis device," "selective cytopheresis inhibitory device," "SCD," and "SCID" refer to embodiments of the present invention that sequester certain cells, such as leukocytes (e.g., activated and/or primed leukocytes) or platelets (e.g., activated platelets). These embodiments can also deactivate and/or inhibit release of pro-inflammatory substances from such cells before, during, and/or after sequestration.

The systems of the present invention are configured to accomplish selective cytopheresis. In basic form, the system includes a SCID, a fluid connection for blood to flow from a blood source (for example, a subject, such as a patient) to the SCID, and a fluid connection for treated blood to flow from the SCID to a receptacle (for example, back to the subject). The SCID acts to sequester leukocytes, such as activated and/or primed leukocytes, and facilitate inhibition of release of a pro-inflammatory substance from the leukocytes and/or deactivate the leukocytes. Sequestration of leukocytes can be achieved by any technique described in Section 3 below. Inhibition of the release of a pro-inflammatory substance from the leukocytes and/or deactivation of the leukocytes can be achieved by any technique described in Section 4 below.

In some embodiments, a system can include a SCID, which optionally can also perform other blood treatments, without additional treatment devices. See, for example, FIGS. 2A-2B and FIG. 8. Other embodiments of a system can include a SCID, which optionally can perform other blood treatments, as well as additional devices that treat blood. See, for example, FIGS. 2C-2D and FIGS. 4A-4F. For example, the additional devices can filter, oxygenate, or otherwise treat the blood before or after the blood enters the SCID. Moreover, the SCID and/or additional devices in a system can include more than one component for treating blood in other or complementary ways, for example, porous filters, oxygen pumps, and/or xenographic or allographic cells (for example, xenographic or allographic renal cells such as renal tubule cells). In some embodiments, the device or devices in the system that facilitate selective cytopheresis are free of such additional components. For example, a SCID of the present invention may be free of cells such as xenographic or allographic cells (e.g., xenographic or allographic renal cells). These basic principles are described in more detail, below.

2.A. Single Device System

Figure 2A:
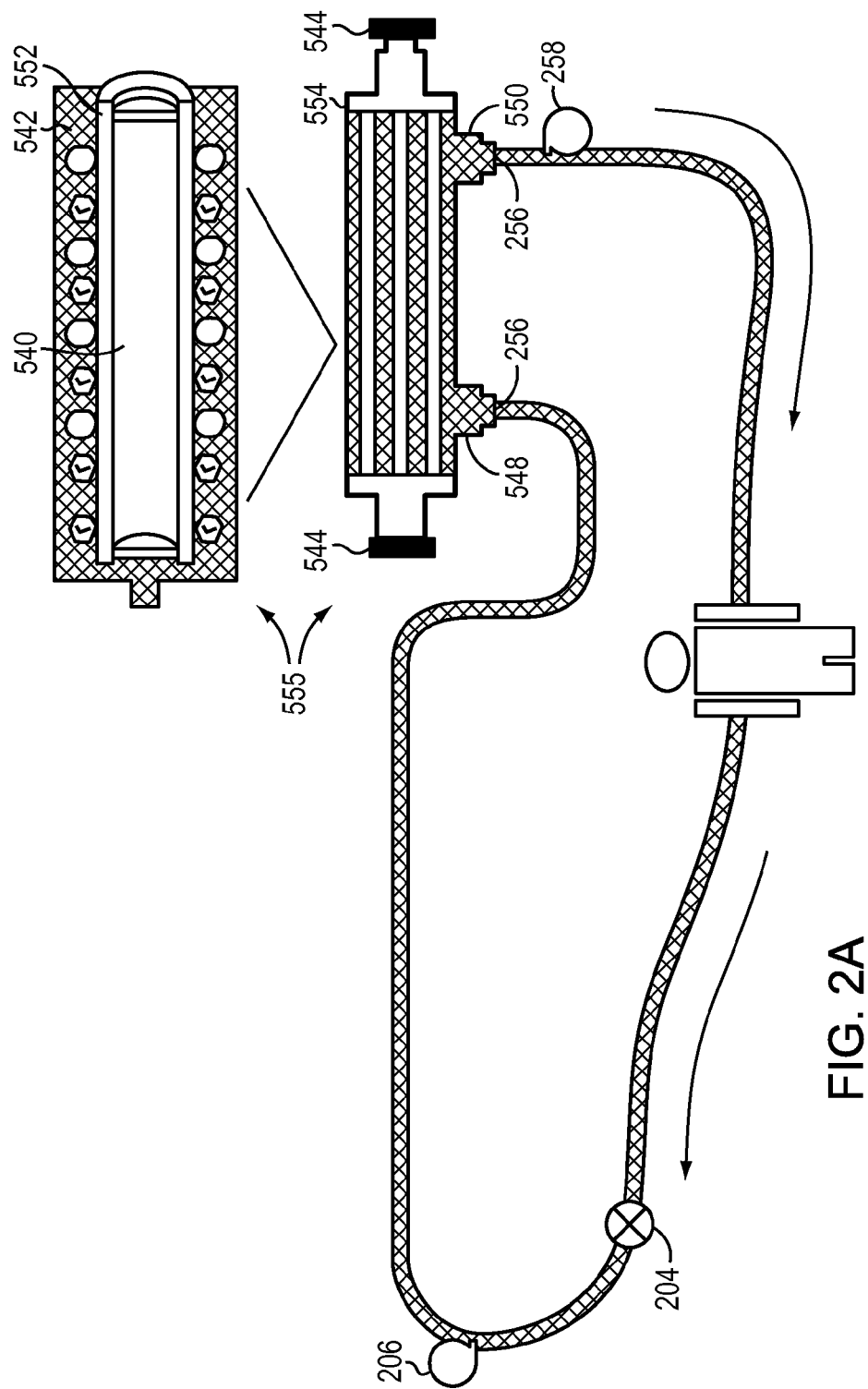
FIG. 2A is a schematic representation of an embodiment of a system of the invention comprising a SCID 555 that is the only device in the system and that includes an intracapillary space (ICS) with both ends capped.
Figure 2B:
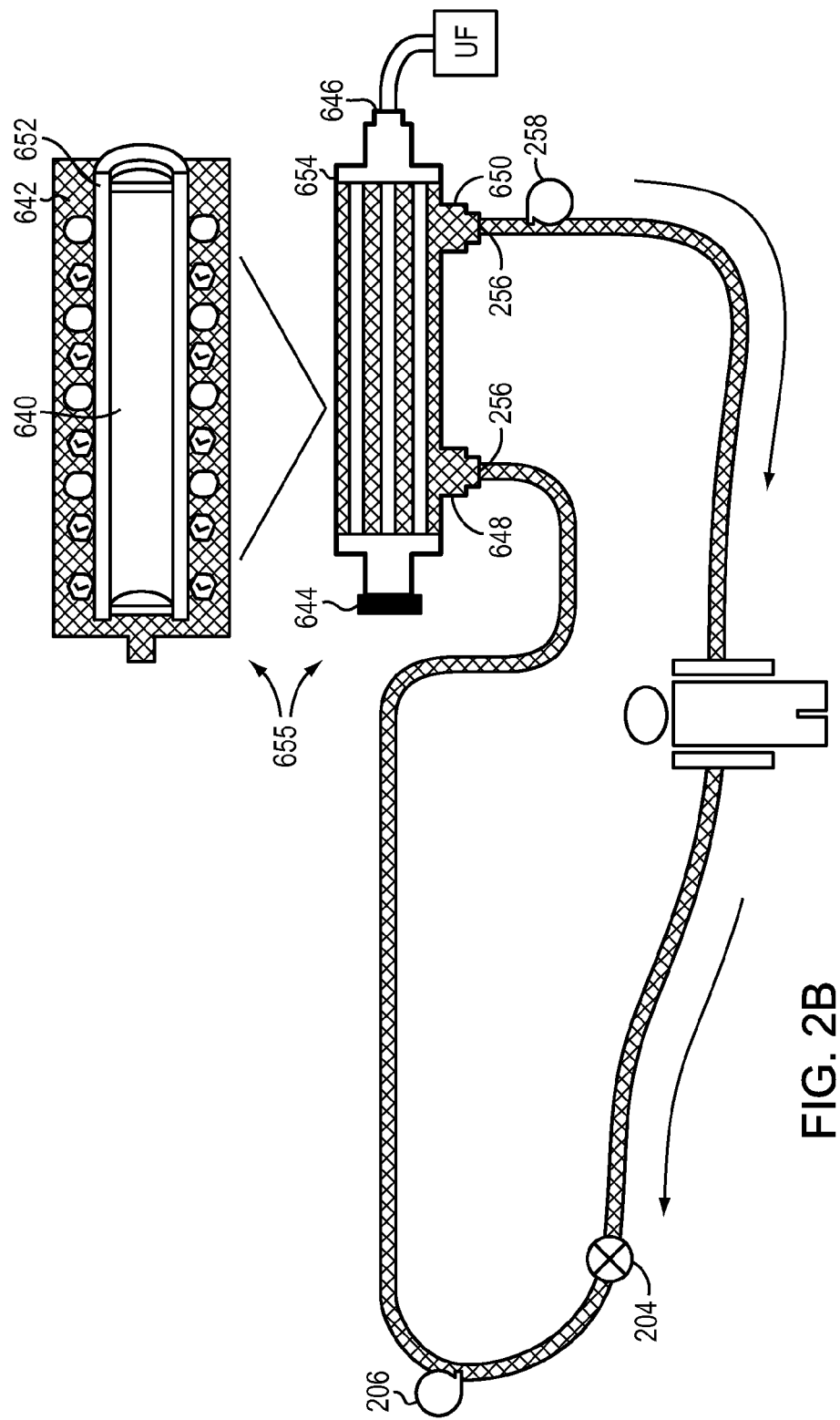
FIG. 2B is a schematic representation of an embodiment similar to FIG. 2A except that ultrafiltrate (UF) is collected from a SCID 655 having only one end of the ICS capped.
Figure 5:
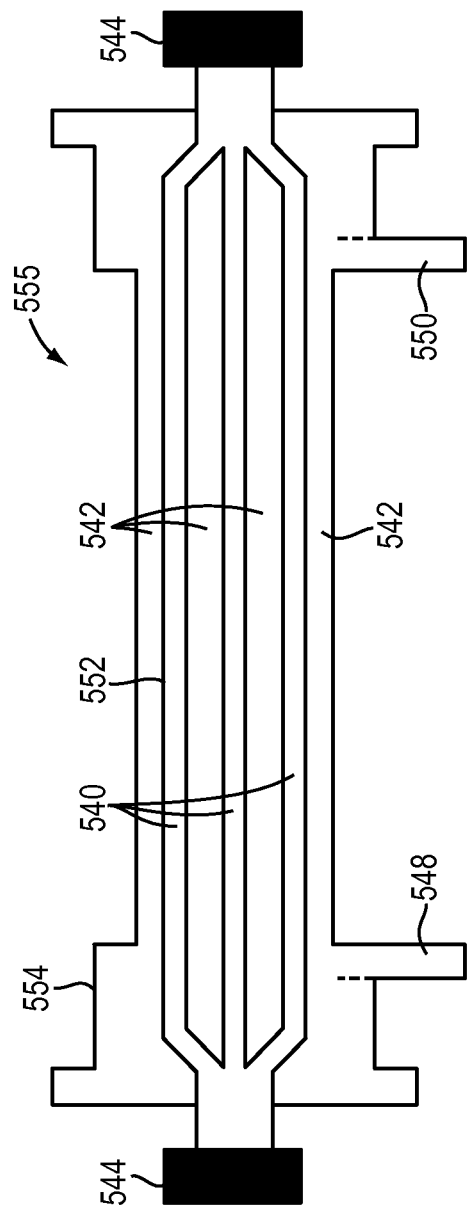
FIG. 5 shows a schematic representation of an embodiment of a SCID 555 of the present invention having an ICS with both ends capped.

As mentioned, a system can contain a SCID to accomplish selective cytopheresis and, optionally, other blood treatments without additional treatment devices in the system (see FIGS. 2A-2B). One embodiment of such a SCID is shown schematically in FIG. 5. In FIG. 5, a SCID 555 contains a plurality of porous membranes, which are hollow fibers 552 (only one is labeled for clarity). The luminal space within these fibers is called the intracapillary space ("ICS") 540. In this embodiment, the ICS inlet and ICS outlet are capped 544. The space 542 surrounding the hollow fibers 552 and within a housing 554 of the SCID 555 is called the extracapillary space ("ECS"). Blood containing leukocytes enters the ECS inlet 548 and moves into the ECS 542 surrounding the fibers 552 (i.e., moves into a passageway). Leukocytes are sequestered in the device, for example, at the external surface of the hollow fibers 552, and exposed to an agent, for example citrate, capable of inhibiting release of a pro-inflammatory substance from a leukocyte and/or deactivating a leukocyte. The agent can be infused into a line upstream of the ECS inlet 548 or may be infused into the SCID itself via a port. Alternatively, or in addition, the SCID can be prepared with the agent, prior to using the SCID. Flow rates in the ECS 542 are chosen in the ranges described herein such that there is a low shear force (in the ranges described herein) at the surface of the fiber 552 to allow leukocytes to associate therewith. In this way, inhibition and/or deactivation of the leukocyte is achieved or initiated. Then, the blood in the ECS exits the SCID via the ECS outlet 550, which enters into an outflow line.

FIG. 2A shows the exemplary SCID 555 of FIG. 5 in a circuit according to the invention. Blood from a subject enters a blood line and is moved through that line via a pump 204. On the same blood line, a leukocyte inhibiting agent (e.g., citrate) can be infused at a port 206, optionally with a pump. The blood in the blood line then enters the ECS inlet 548 and exits the SCID 555 at the ECS outlet 550. Blood lines at the ECS inlet 548 and outlet 550, respectively, are attached using blood line connectors with locking mechanisms 256. Leukocytes are shown sequestered in the ECS 542 at the external surface of the hollow fiber 552. A blood outflow line from the ECS outlet 550 returns blood to the subject. Another agent, such as calcium (e.g., calcium chloride or calcium gluconate), can be infused at a port 258 on this blood outflow line to prepare the blood for re-entry into the subject. In certain embodiments, the ICS can contain xenographic or allographic cells, for example, renal tubule cells, cultured in a monolayer on the lining of the ICS 540 of each fiber to further aid in treatment of the blood. However, in other embodiments, the ICS is cell-free. In the circuit of FIG. 2A, the lumen 540 of the SCID 555 is filled with saline.

Figure 6:
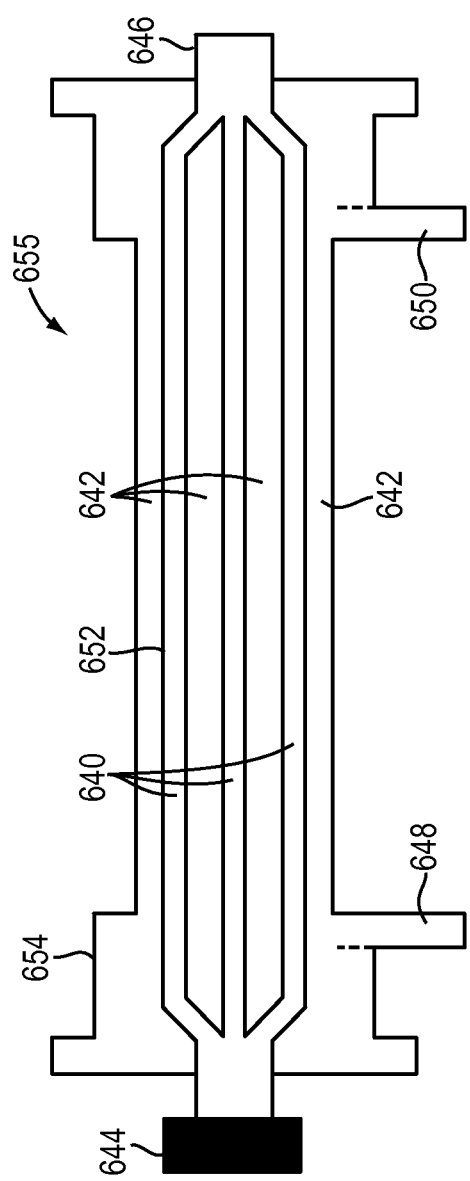
FIG. 6 shows a schematic representation of an embodiment of a SCID 655 of the present invention having an ICS with one end capped.

The circuit of FIG. 2B includes the same components as FIG. 2A and operates in the same manner, except that FIG. 2B utilizes SCID 655 shown in FIG. 6 and ultrafiltrate is produced by this SCID 655. The SCID 655 contains a plurality of porous membranes, which are hollow fibers 652. The luminal space within the fibers is the ICS 640 and the surrounding space outside the fibers 652 and within the SCID housing 654 is the ECS 642. Blood containing leukocytes enters the ECS inlet 648 and moves into the ECS 642 surrounding the fibers 652 and exits at the ECS outlet 650. Leukocyte sequestration and inhibition and/or deactivation can be achieved as described above. However, in SCID 655, only the ICS inlet is capped 644. The ICS outlet 646 is not capped. Accordingly, depending on the characteristics of the porous hollow fibers 652 (e.g., permeability and pore size), a portion of the blood in the ECS 642 can pass across the hollow fibers 652, and into the ICS 640 as ultrafiltrate (UF). A tube can be connected to the ICS outlet 646 for collecting ultrafiltrate (UF), which may be discarded as waste.

Figure 8:
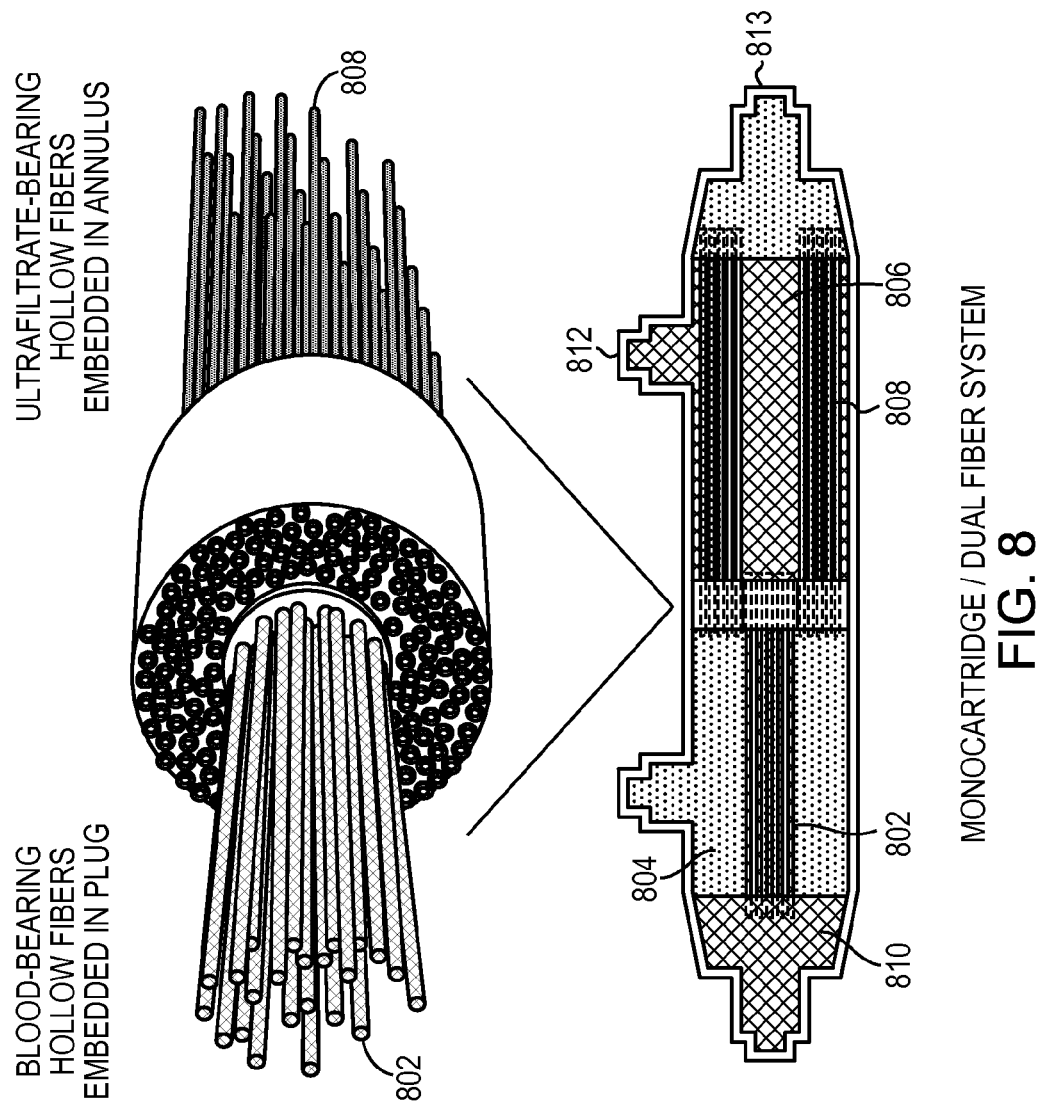
FIG. 8 shows an additional embodiment of a SCID 855 of the present invention.

In another embodiment of a system with a single treatment device, the SCID can be a device as shown in FIG. 8. Blood enters one end 810 of the SCID 855 and travels through hollow fibers 802 through which ultrafiltrate passes into a hollow space 804. The filtered blood from the hollow fibers 802 passes into an ECS 806 and surrounds hollow fibers 808 containing ultrafiltrate, which was passed from the hollow space 804. The blood in the ECS flows over the hollow fibers 808 filled with ultrafiltrate, and leukocytes are sequestered thereon. Flow rates are chosen in the ranges described herein to develop a shear force (in the ranges described herein) at the surface of the ultrafiltrate hollow fibers 808 that permit leukocytes to associate with the fibers. Blood ultimately exits the device at a side port 812, and ultrafiltrate exits as waste via an end port 813. The interior of the ultrafiltrate hollow fibers 808 optionally contain renal tubule cells. This embodiment of a SCID can be placed in a circuit as described for the SCID of FIGS. 2A-2B.

Flow rates and membrane characteristics for the embodiments shown in the circuits of FIGS. 2A-2B with the SCID of FIG. 5, 6, or 8 can be as described below. For example, the ECS flow rate may be from about 100 mL/minute to about 500 mL/minute. The flow rate of the ultrafiltrate waste (e.g., for the SCIDs shown in FIGS. 6 and 8) may include, for example, flow rates from about 5 mL/minute to about 50 mL/minute.

Figure 2C:
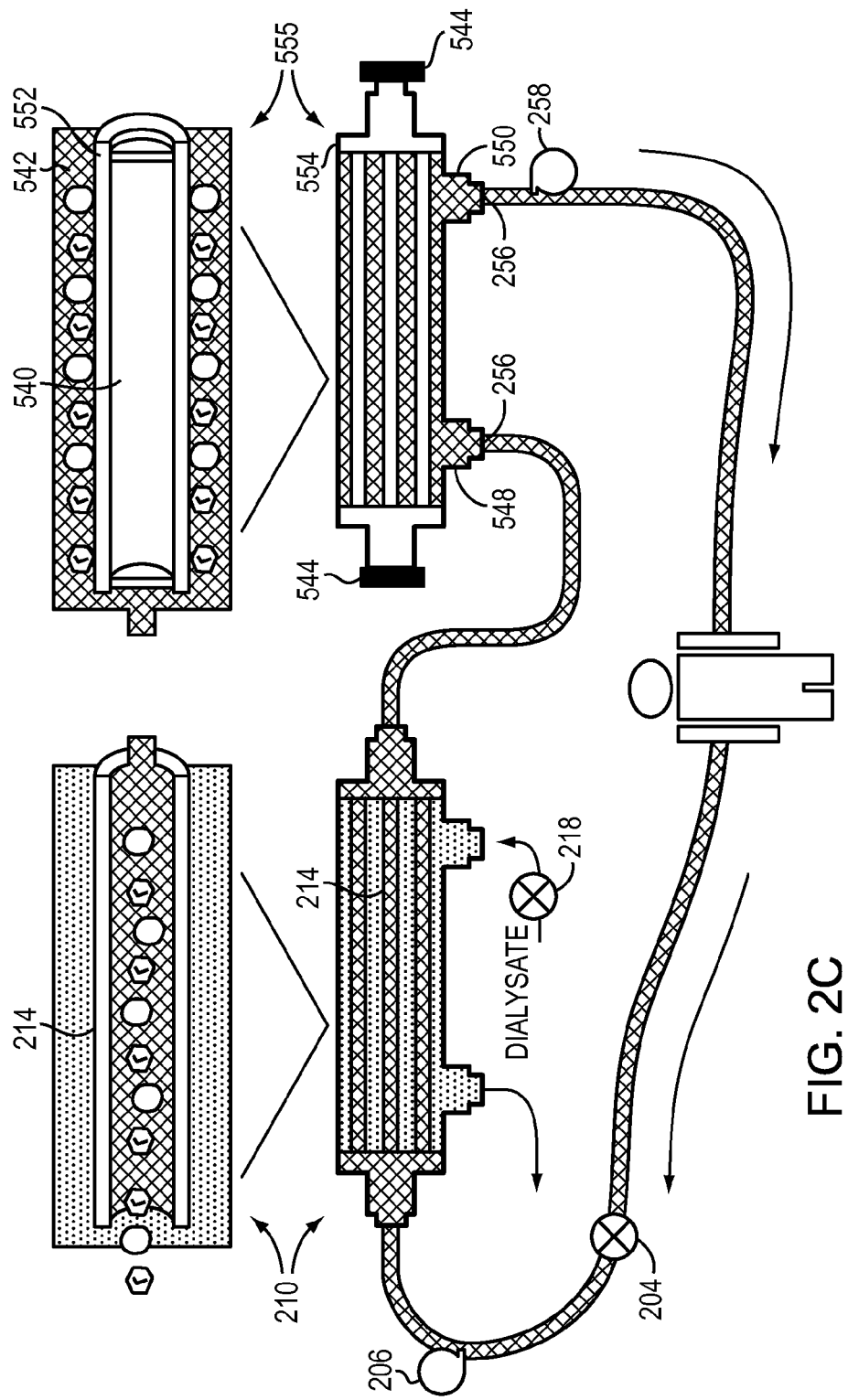
FIG. 2C is a schematic representation of an embodiment of a system of the invention comprising a first device, for example, a hemofiltration device 210, and a SCID 555 that includes an ICS with both ends capped.
Figure 2D:
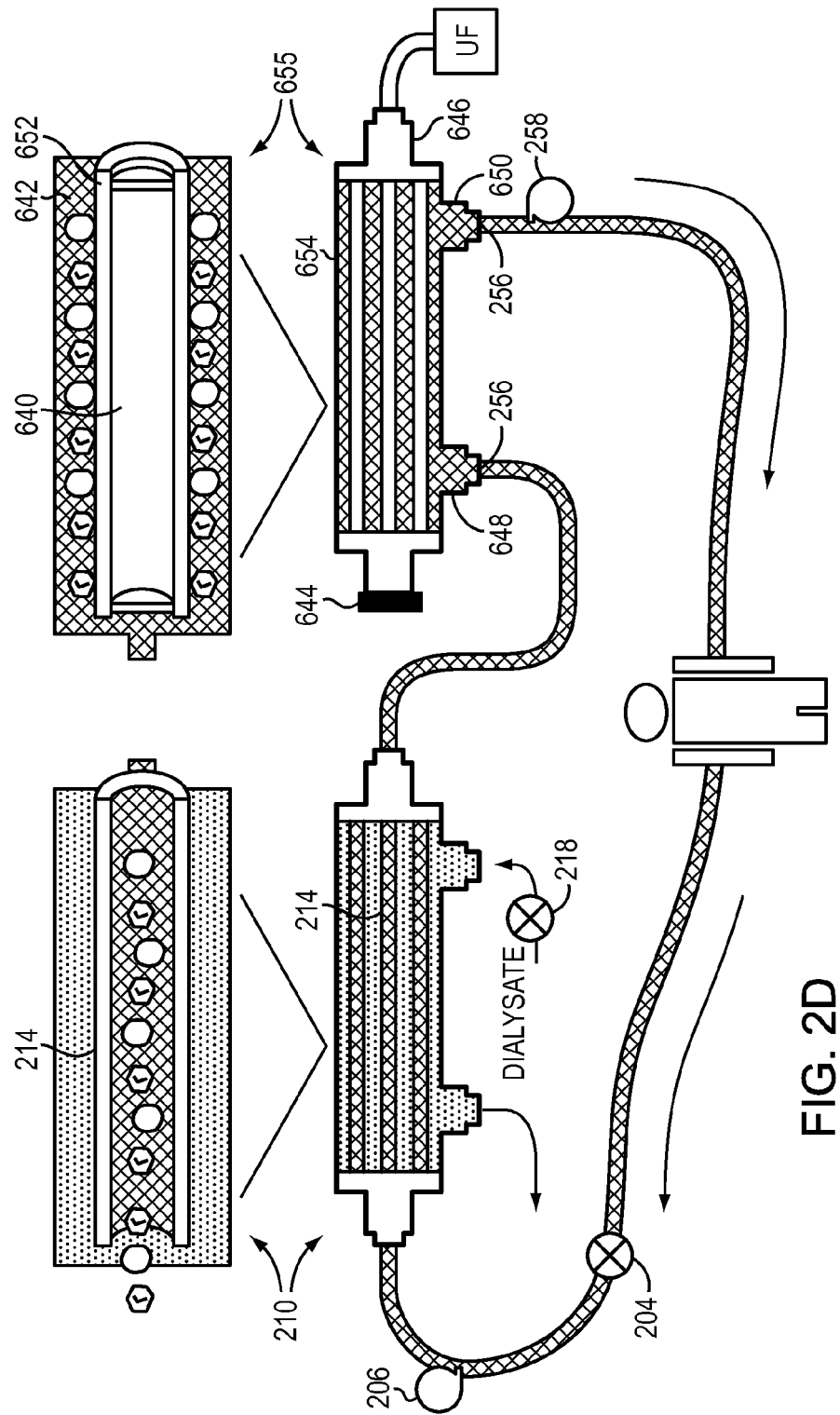
FIG. 2D is a schematic representation of an embodiment similar to FIG. 2C except that ultrafiltrate (UF) is collected from a SCID 655 having only one end of the ICS capped.

2.B. Selective Cytopheresis Inhibitory Device as Part of a Hemodialysis or Hemofiltration System As mentioned, in some embodiments the SCID is part of a system with other devices for treating blood. For example, the SCID can be a part of a hemofiltration system, a hemodialysis system and/or a hemodiafiltration system that includes one or more filtration cartridges separate from the SCID within the system. When describing the part of the system that is not the SCID, the term "hemofiltration" can refer to hemodialysis, hemodiafiltration, hemofiltration, and/or hemoconcentration and "hemofilter" can include a device (e.g., a cartridge) for performing one or more of hemodialysis, hemodiafiltration, hemofiltration, and/or hemoconcentration. The hemofiltration cartridge(s) can be configured to be in parallel or series with a SCID within an extracorporeal blood circuit, and associated blood pumps and tubing can be used to move the blood through the extracorporeal circuit. For example, as shown in FIGS. 2C and 2D, blood flows from a subject through a blood line. The blood is moved through the blood line via a pump 204. A leukocyte inhibiting agent (e.g., citrate) can be infused into the same blood line at a port 206, optionally with a pump. The blood then flows through hollow fibers 214 in a conventional hemofilter 210. Dialysate is infused into the ECS surrounding the hollow fibers 214 and within the hemofilter 210 housing, and dialysis occurs with solutes being removed as "waste" from the blood across the hemofilter filtration membrane 214 (the hollow fibers) and into the dialysate. The dialysate flows in a counter current fashion relative to the blood, and the dialysate is moved with a dialysate pump 218. Additionally, molecules and fluid from the blood can pass across the hemofilter filtration membrane 214 (the hollow fibers) as ultrafiltrate, depending on the pore size through the membrane.

The exemplary system of FIG. 2C shows a circuit with the SCID 555 of FIG. 5. Blood exits the hemofilter 210 and enters the SCID 555 at the ECS inlet 548. The blood then is processed through the SCID, which sequesters leukocytes on the hollow fibers 552 and inhibits release of a pro-inflammatory substance from a leukocyte and/or deactivates a leukocyte in the manner described for FIGS. 2A-2B, above. The blood lines into and out of the SCID 555 are attached using a connection with a locking mechanism 256. The blood is then returned to the subject via a blood outflow line from the ECS outlet 550. Another agent, such as calcium, can be infused at a port 258 on the this blood outflow line in order to prepare the blood for re-entry into the subject. In certain embodiments, the intracapillary space (ICS) of the SCID can contain xenographic or allographic cells, for example, renal tubule cells, cultured in a monolayer on the lining of the lumen of each fiber to further aid in treatment of the blood. However, in other embodiments the ICS is cell free. In the circuit of FIG. 2C, the ICS 540 of the SCID 555 is filled with saline and the end ports of the ICS are capped 544.

The circuit of FIG. 2D includes the same components as FIG. 2C and operates in the same manner, except that FIG. 2D utilizes the SCID 655 of FIG. 6 and ultrafiltrate is produced by this SCID 655. The flow of blood through the SCID 655 is described above in the context of FIG. 2B. Additionally, SCID 655 functions as described above, in the context of FIG. 2B. As noted above, SCID 655 has only the ICS inlet capped 644. The ICS outlet 646 is not capped. Accordingly, depending on the characteristics of the porous hollow fibers 652, a portion of the blood in the ECS 642 can pass across the hollow fibers 652, and into the ICS as ultrafiltrate (UF). A tube can be connected to the ICS outlet 646 for collecting ultrafiltrate (UF), which may be discarded as waste.

Without wishing to be bound by theory, it is contemplated that the flow geometry in these embodiments of the SCID system (and those shown in FIGS. 1, 2A-2B, 3, and 4A-4F) allows leukocytes to exist in a low shear force environment in the ECS of the SCID and, therefore, associate with one or more internal surfaces in the SCID, for example, the hollow fibers. Conversely, in a typical use of a hemofiltration cartridge (for example, the first device 210 in the circuits of FIGS. 2C and 2D), blood flow through the small diameter lumens of the hollow fibers yields a higher shear force (than that in the SCID) that prohibits association of leukocytes with the hollow fibers and sequestration of leukocytes within the device. Accordingly, a hemofiltration device having the conventional flow circuit supporting its operation reversed (i.e., blood flowing outside the hollow fibers rather than inside the hollow fibers) can act as a SCID to sequester potentially damaging and circulating activated leukocytes. These sequestered leukocytes can be treated with a leukocyte inhibiting agent (e.g. citrate).

Further, it is contemplated that the inflammatory response of sequestered leukocytes is inhibited and/or deactivated in the presence of low $Ca_i$ (caused, for example, by citrate) before, during, and/or after sequestration. The low-$Ca_i$ environment may inhibit the inflammatory activity of, or deactivate, the leukocytes.

In certain embodiments, rather than both dialysate and ultrafiltrate being produced by the hemofilter (e.g., the hemofilter 210 of FIGS. 2C and 2D), only ultrafiltrate is produced. During ultrafiltration, blood is separated into ultrafiltrate, which has been filtered through a medium, such as a membrane, and a retentate, which does not pass through the medium. One example of this type of system is the SCID 755 of FIG. 7 in the system of FIG. 3. Briefly, in this system the blood flows in through the ECS inlet 748 of the SCID 755, into the ECS 742 defined by the SCID housing 754 and hollow fibers 752, and out through the ECS outlet 750 in the SCID 755. Additionally, an ultrafiltrate line 320 from the hemofilter 210 is in communication with the ICS 740 of the SCID 755 via an ICS inlet 745 and provides ultrafiltrate to the ICS 740. The filtered blood (in the ECS 742) and the ultrafiltrate (in the ICS 740) are separate but can interact with one another across the membranes of the hollow fibers 752. The ultrafiltrate in the ICS 740 and the filtered blood in the ECS 742 of the SCID 755 can flow in a cocurrent or countercurrent manner. Processed ultrafiltrate exits the ICS 740 at the ICS outlet 746 of the SCID 755 and can be discarded as a waste product. Accordingly, in this embodiment, the ICS inlet 745 and ICS outlet 746 are not capped, but the SCID 755 is otherwise substantially the same as the one shown in FIG. 5 and FIG. 6.

Figure 3:
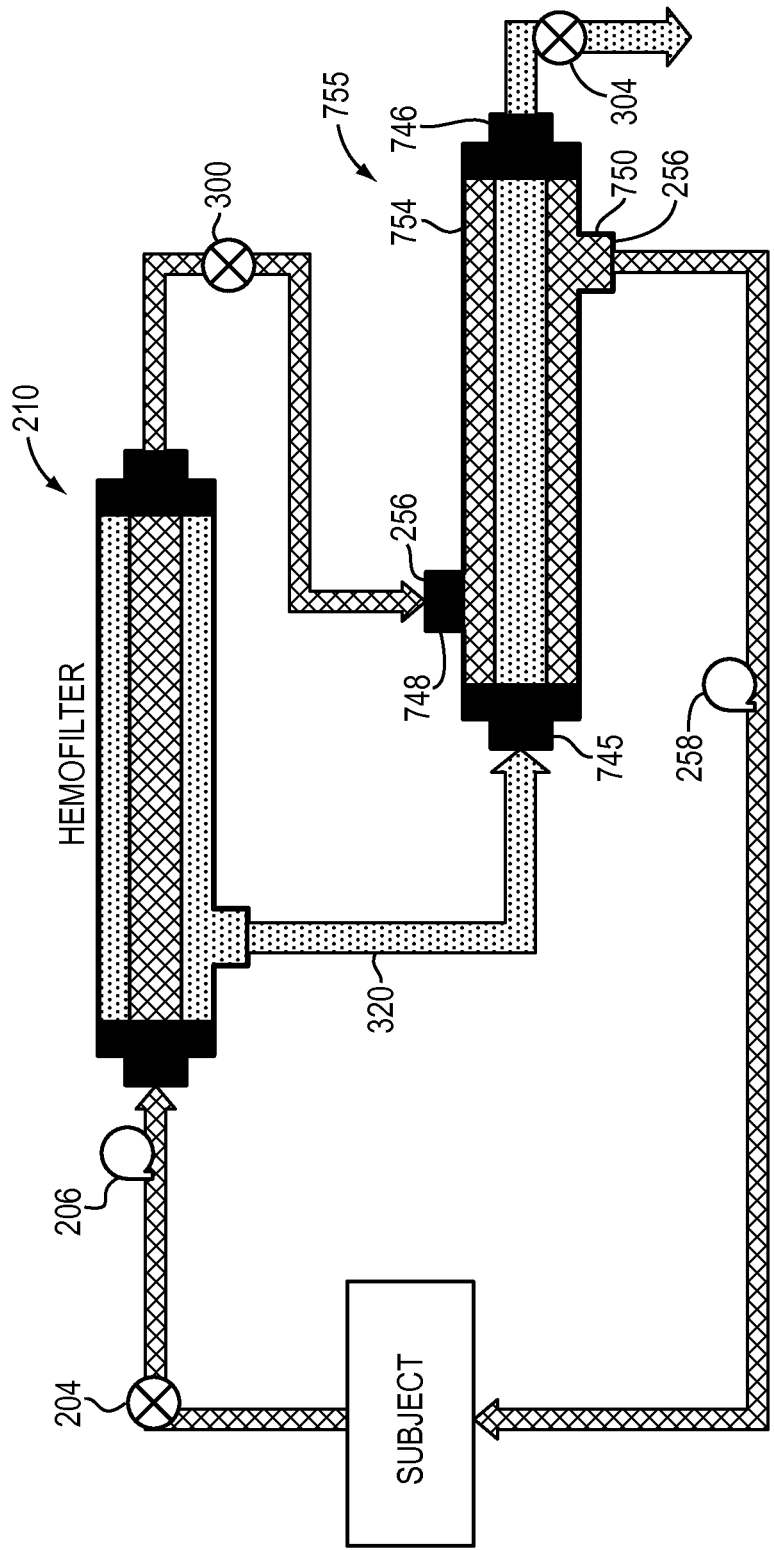
FIG. 3 is a schematic representation of an embodiment of a system of the invention including a SCID 755 without a cap on its ICS.
Figure 7:
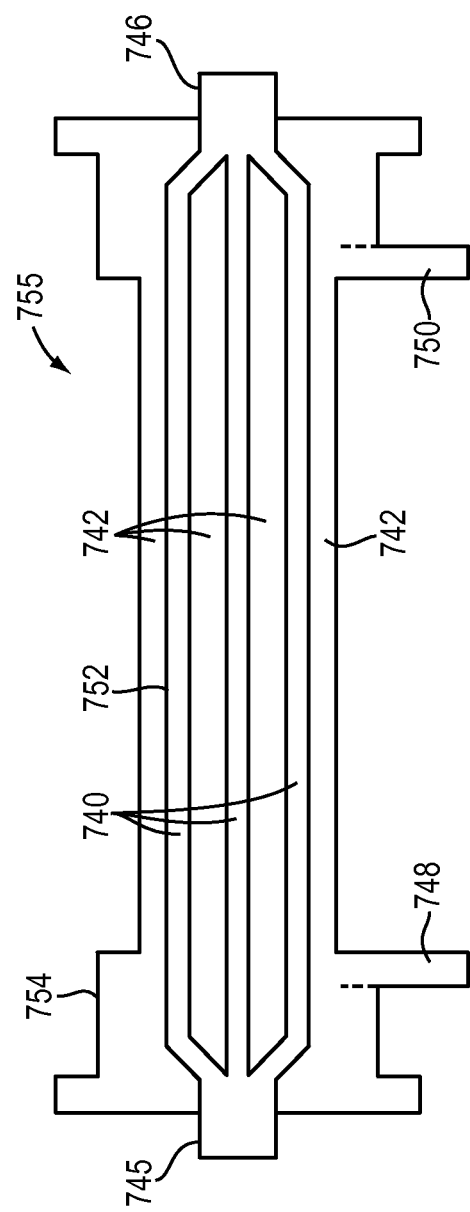
FIG. 7 shows a schematic representation of an embodiment of a SCID 755 of the present invention having an ICS inlet 745 and ICS outlet 746, neither of which is capped.

More particularly, in the system of FIG. 3 using the SCID 755 according to FIG. 7, blood is moved from a subject (for example, a patient or any animal) in a blood line. Blood is pumped through the blood line with a pump 204. A leukocyte inhibiting agent, such as citrate, can be infused at port 206, optionally with a pump. The blood then enters hollow fibers of a hemofilter 210 and deposited into the ECS of the hemofilter 210 in a manner described for FIGS. 2C-2D above. Ultrafiltrate is produced across the hollow fibers of the hemofilter 210 and is deposited into the ECS of the hemofilter 210. The ultrafiltrate then passes through an ultrafiltrate line 320 from the hemofilter 210 and enters the SCID 755 at an ICS inlet 745. The ultrafiltrate moves through the ICS 740 of the hollow fibers 752 and exits at the ICS outlet 746. The hollow fibers can be porous, semi-porous, or non-porous membranes.

The filtered blood remaining in the ICS of the hollow fibers of the hemofilter 210 (i.e., the lumens of the hollow fibers in the hemofilter 210) exits the hemofilter 210 and is pumped with pump 300 into the ECS inlet 748 of the SCID 755. Optionally, this pump can be placed on the blood line between the SCID and the subject or a third pump (not shown) can be placed on the blood line between the SCID and the subject. The blood flows into the ECS 742 surrounding the hollow fibers 752 (i.e., moves in a passageway). Leukocytes, such as activated and/or primed leukocytes, are sequestered in the device, for example, at the external surface of the hollow fibers 752. Blood then exits the SCID 755 at the ECS outlet 750 and returns to the subject. Blood line connectors 256 with a locking mechanism attach the blood lines to the ECS inlet 748 and the ECS outlet 750. Another agent, such as calcium, can be infused at a port 258 on the blood outflow line returning to the subject to prepare the blood for re-entry into the subject. Also, an ultrafiltrate pump 304 moves ultrafiltrate from the ICS 740 to waste. However, depending on the pump flow rates in the system, none, some, or all of the ultrafiltrate can cross the hollow fibers 752 and return to the filtered blood in the ECS 742.

The use of the SCID of FIG. 7 in the circuit shown in FIG. 3 has been evaluated in over 100 large animals in pre-clinical testing and in nearly 100 patients in Phase I, IIa, and IIb clinical studies with no unanticipated adverse events related to the SCID and the perfusion circuit. Although the ICS can be cell free, it is understood that this system optionally also can include cells within the ICS 740, for example renal tubule cells. The rate of the blood flow is chosen to have a sufficiently low shear force (in the ranges described herein) at the surface of the porous, hollow fibers to allow sequestration of leukocytes by association with the fibers, for example at a blood flow rate from about 100 mL/minute to about 500 mL/minute. Alternatively, the blood flow rate through the extracorporeal circuit, through the lumens of the hollow fibers in the hemofilter 210, and through the ECS 742 of the SCID 755 can be about 120 mL/minute. The ultrafiltrate can be moved at rates in the ranges described herein, for example, at flow rates less than about 50 mL/minute, from about 5 mL/minute to about 50 mL/minute, and from about 10 mL/minute to about 20 mL/minute. Alternatively, the ultrafiltrate flow rate can be maintained at 15 mL/minute. Optionally, a balanced electrolyte replacement solution (e.g., a solution containing bicarbonate base) can be infused into the bloodline on a 1:1 volume replacement for ultrafiltrate produced. The fluid (e.g., ultrafiltrate) and blood (or leukocyte-containing fluid) can flow in the same direction or in opposite directions.

In this and other embodiments, the blood flow configuration through the SCID is opposite the blood flow configuration through a typical hemofiltration cartridge. That is, blood flows through the interior of the hollow fibers of the hemofiltration cartridge in its intended use versus around the outside of the hollow fibers of the SCID. This unconventional blood flow configuration through the SCID allows for a lower shear force within the ECS at the exterior surface of the hollow fiber relative to the higher shear force within the lumen of the hollow fibers of a hemofilter, thus facilitating sequestration of leukocytes in the ECS of the SCID. Conversely, the blood flow through the interior of the hollow fibers of the hemofilter prohibits leukocyte sequestration due to high shear force created by blood flowing through the small diameter lumens of the hollow fibers. For example, tests have shown that blood within the interior of a hollow fiber of a hemofilter creates a shear force of $1.5 \times 10^7$ dynes/cm$^2$ while blood flow through the ECS of certain embodiments of a SCID creates a shear force of 5.77 dynes/cm$^2$, or $10^6$ less shear force. For comparison, the shear force at a typical arterial wall is 6 to 40 dynes/cm$^2$ and the shear force at a typical vein wall is 1-5 dynes/cm$^2$. Thus, a capillary wall has a shear stress of less than 5 dynes/cm$^2$.

Accordingly, in some embodiments, the present invention uses a sufficiently low shear force at a surface in a region of a passageway configured to sequester leukocytes to be able to associate leukocytes with that surface and sequester leukocytes, such as activated and/or primed leukocytes in the region. For example, in some embodiments a shear force of less than 1000 dynes/cm$^2$, or less than 500 dynes/cm$^2$, or less than 100 dynes/cm$^2$, or less than 10 dynes/cm$^2$, or less than 5 dynes/cm$^2$, is useful at a surface in the passageway region configured to sequester leukocytes. It should be understood that these shear forces may be useful in any of the SCID embodiments described herein. In certain embodiments, having two devices, such as a hemofilter and a SCID, the difference in shear force between blood flowing in the hemofilter and blood flowing in the SCID can be at least 1000 dynes/cm$^2$.

In these and other embodiments, so long as the unconventional flow configuration is followed (i.e., blood flows outside of the hollow fibers, rather than inside the hollow fibers) to yield the requisite shear force, the SCID can be comprised of a conventional 0.7 m$^2$ polysulfone hemofilter (e.g., Model F40, Fresenius Medical Care North America, Waltham, Mass., U.S.A.), which is approved by the FDA for use in acute and chronic hemodialysis. Similarly, the extracorporeal perfusion circuit of this or any other embodiment can use standard dialysis arteriovenous blood tubing. The cartridges and blood tubing can be placed in any dialysate delivery pump system (e.g., Fresenius 2008H) that is currently in use for chronic dialysis.

In one exemplary system, the system includes tubing leading from a subject (a blood line) with a bag of a citrate solution infused into the tubing by an infuser. A first F40 hemofilter cartridge is connected with the blood line at a point after the citrate enters the blood line. Blood in the blood line then flows through the interior of hollow fibers (the ICS) inside the cartridge, from an end port inlet to an end port outlet, and dialysate flows outside these hollow fibers and within the cartridge (the ECS) from one side port to a second side port in a countercurrent manner with respect to the blood flow. A dialysate/ultrafiltrate mixture exiting from the second side port is collected. Substantially no blood cells, platelets, or plasma cross from the ICS to the ECS, and substantially no leukocytes adhere to the interior of the hollow fibers. The hollow fibers are disposed parallel to one another in a bundle, and each fiber has a diameter of approximately 240 micrometers. Furthermore, the pores of the hollow fibers are small enough to prevent passage of albumin, a molecule of about 30 angstroms, through the fibers, and the pores are generally this size across the entire fiber. The filtered blood then continues from the end port outlet, through tubing, to a side port inlet of a second F40 cartridge (i.e., the SCID). The blood flows through the ECS of the second F40 cartridge and exits the cartridge at a side port outlet. Any ultrafiltrate that is produced in the second F40 cartridge enters the ICS and exits through an end port. The other end port of the cartridge is capped. Substantially no blood cells, platelets, or plasma cross from the ECS to the ICS, and leukocytes adhere to the exterior of the hollow fibers for some period of time. Blood exiting the second F40 cartridge enters tubing where a calcium solution is infused into the blood using an infuser. Finally, the tubing returns the processed blood to the subject. In certain embodiments, the blood flow rate in the system does not exceed 500 mL/minute, and blood does not displace air in the system at any point. Additionally, the pumping and infusion rates can be manually changed in view of bedside readings of electrolytes and white blood cell counts. An i-STAT® handheld monitoring device produces these readings from a small amount of blood withdrawn from the subject.

The risk of using such a system is similar to the risk associated with hemodialysis treatment and includes, for example, clotting of the perfusion circuit, air entry into the circuit, catheter or blood tubing kinking or disconnection, and temperature dysregulation. However, dialysis machines and associated dialysis blood perfusion sets have been designed to identify these problems during treatment with alarm systems and to mitigate any clot or air embolism to the subject with clot filters and air bubble traps. These pump systems and blood tubing sets are FDA approved for this treatment indication.

As mentioned above, infusion of a leukocyte inhibition agent, for example, citrate, can be local to the SCID, regional, or throughout the system. In this or any embodiment, citrate can also be used as an anti-clotting agent, in which case perfusion throughout the system would be useful. Clinical experiences suggest that if clotting occurs within a hemofiltration system, it is initiated in the first dialysis cartridge. Anticoagulation protocols, such as systemic heparin or regional citrate, are currently established and routinely used in clinical hemodialysis.

2.C. Selective Cytopheresis Inhibitory Device as Part of a Cardiopulmonary Bypass System As shown in FIGS. 4A-4F and as described in Examples 8 and 9 herein, a SCID can be used within a cardiopulmonary bypass (CPB) circuit to treat and/or prevent inflammatory conditions secondary to surgeries (e.g., bypass surgery). FIGS. 4A, 4B, 4D, 4E, and 4F show the SCID of FIG. 5 in exemplary CPB systems. FIG. 4C shows the SCID of FIG. 6 in an exemplary CPB system. CPB is used to divert blood from both the left and right sides of the heart and lungs. This is achieved by draining blood from the right side of the heart and perfusing the arterial circulation. However, since systemic-to-pulmonary collaterals, systemic-to-systemic collaterals, and surgical site bleeding return blood to the left side of the heart, special drainage mechanisms of the left side of the heart are required during CPB. Optionally, cardioplegia can be delivered through a special pump and tubing mechanism. A standard CPB system has several features that can be broadly classified into three subsystems. The first subsystem is an oxygenating-ventilating subsystem that supplies oxygen and removes carbon dioxide from the blood. The second subsystem is a temperature control system. The third subsystem includes in-line monitors and safety devices.

Figure 4A:
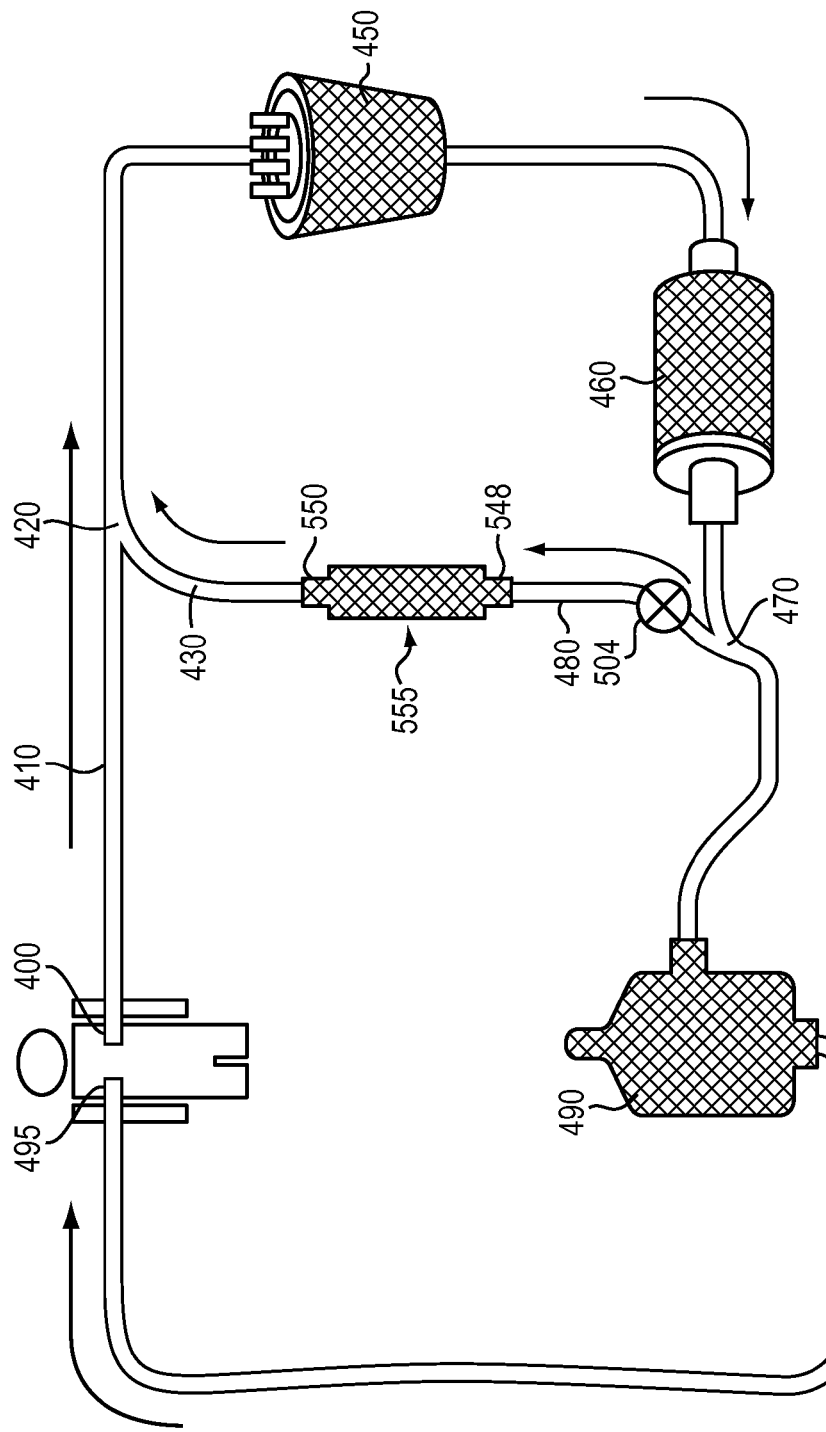
FIGS. 4A-4F are schematic representations of embodiments of system configurations of the present invention as utilized in a CPB circuit.

As shown in the embodiment of FIG. 4A, blood is moved via a venous cannula 400 from a subject into a blood line 410. Blood flows through the blood line 410, passing a recirculation junction 420, which is connected to a SCID outflow line 430. The SCID outflow line 430 contains blood treated by the SCID device 555. The blood in the blood line 410 mixes with the SCID-treated blood and continues to a venous reservoir 450 and onto an oxygenator 460 where the blood is oxygenated. The oxygenated blood then flows from the oxygenator 460 to a junction 470 with a SCID inflow line 480. Here, where a portion of the blood in the blood line 410 is diverted to the SCID 555 via the SCID inflow line 480 for treatment by the SCID 555. The flow of blood through the SCID inflow line 480 is controlled by a pump 504. The SCID 555 is designed to sequester select cells associated with inflammation, for example, leukocytes or platelets. In this embodiment, no leukocyte inhibiting agent is added to the blood entering the SCID 555. Blood containing leukocytes enters the ECS inlet 548 and moves into the ECS 542 surrounding the hollow fibers 552. Leukocytes are sequestered in the device, for example, at the external surface of the hollow fibers 552. Flow rates at pump 504 can be chosen at ranges described herein such that there is a low shear force (in the ranges described herein) at the surface of the hollow fibers 552 to allow leukocytes to associate therewith. Blood in the ECS 542 exits the SCID via the ECS outlet 550 and enters the SCID outflow line 430. At junction 470, a portion of the blood in the blood line 410 also continues to an arterial filter/bubble trap 490, before being returned to the subject at an arterial cannula 495.

Figure 4B:
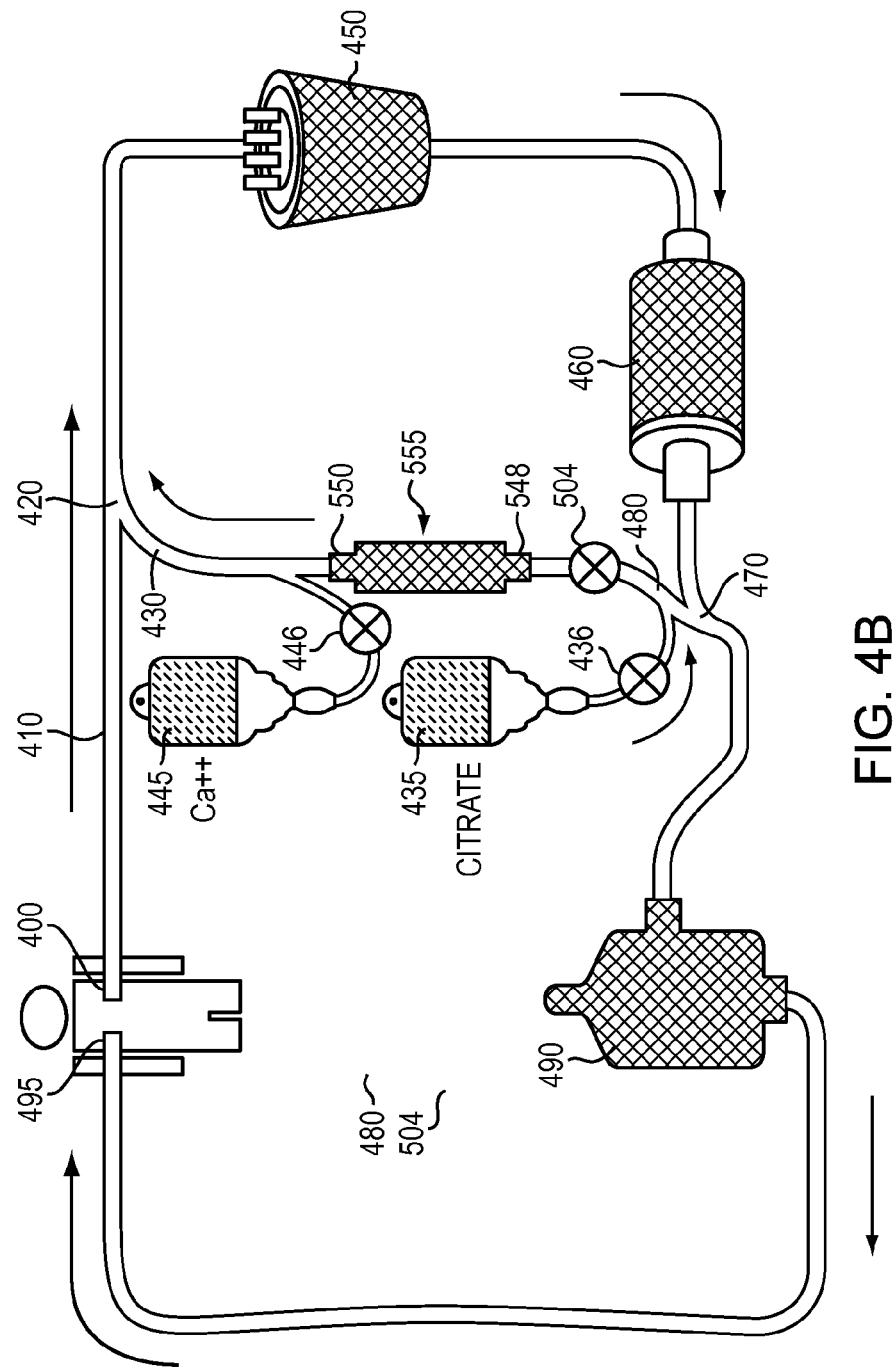
Figure 4C:
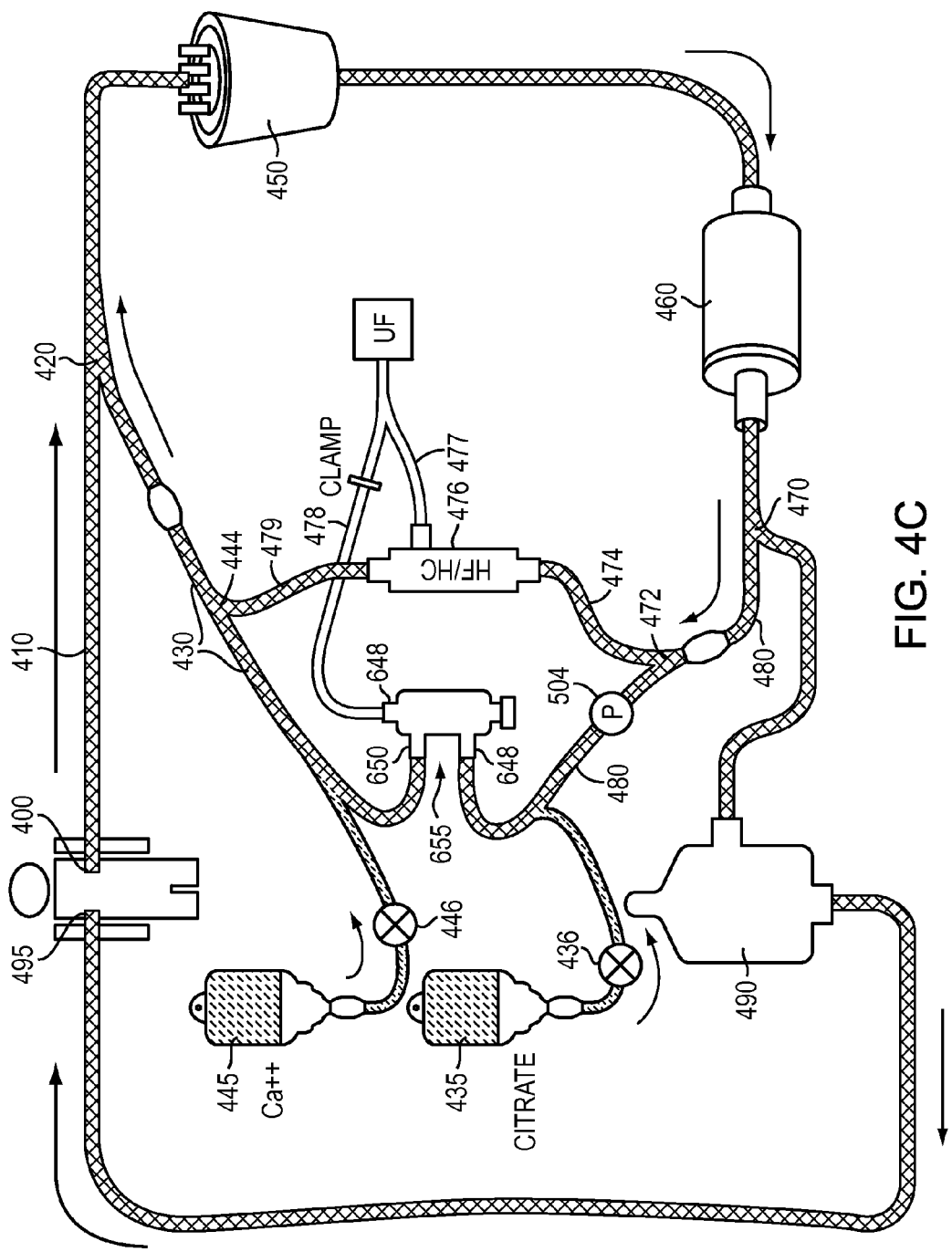

The circuit in FIG. 4B flows in the same fashion as the circuit in FIG. 4A, with the additional features of a citrate feed 435 and citrate pump 436 to add citrate to the blood in the SCID inflow line 480 and a calcium feed 445 and calcium pump 446 to add calcium to the blood in the SCID outflow line 430. Citrate (or another leukocyte inhibiting agent described herein) is added to the blood flowing into the SCID 555 from the citrate feed 435 to inhibit and/or deactivate cells associated with inflammation, such as leukocytes. Calcium can be added back into the blood to prepare the blood for reentry into the subject.

The circuit in FIG. 4C functions in a similar fashion as the circuit in FIG. 4B, with additional features associated with a hemofilter/hemoconcentrator (HF/HC) 476. Specifically, the portion of the oxygenated blood that is diverted at junction 470 toward the SCID 655 via the SCID inflow line 480 is further split at junction 472 into a portion that flows to the SCID 655 and a separate portion that flows to the HF/HC 476 via a HF/HC inflow line 474. The HF/HC can filter or concentrate the blood, with ultrafiltrate passing from the device via a waste tube 477. The filtered or concentrated blood exits the HF/HC 476 via a HF/HC outflow line 479 that returns the filtered or concentrated blood to the SCID outflow line 430 at a junction 444. The SCID shown in FIG. 4C is the SCID of FIG. 6, as described above. Blood flows from the SCID inflow line 480, into the ECS inlet 648, through the ECS, out the ECS outlet 650, and into the SCID outflow line 430. Ultrafiltrate may be produced across the hollow fibers in the SCID (from the ECS to the ICS), with ultrafiltrate passing from the SCID at the ICS outlet 646 into a waste tube 478.

Blood flow to the SCID 655 can be controlled by the pump 504. Pump 504 is preferred to maintain constant flow in embodiments that infuse agents, such as citrate, that inhibit or deactivate the leukocytes, and/or another agent, such as calcium, following SCID treatment. Alternatively, blood flow to the SCID can be controlled by selecting a smaller caliber of the SCID inflow line 480 between junction 472 and the SCID 655 relative to the caliber of the HF/HC inflow line 474, so that only about 200 mL/5 L (about 4% of the flow volume) is diverted to the SCID at the junction 472. This results in low shear force in the SCID, which can facilitate sequestration.

Figure 4D:
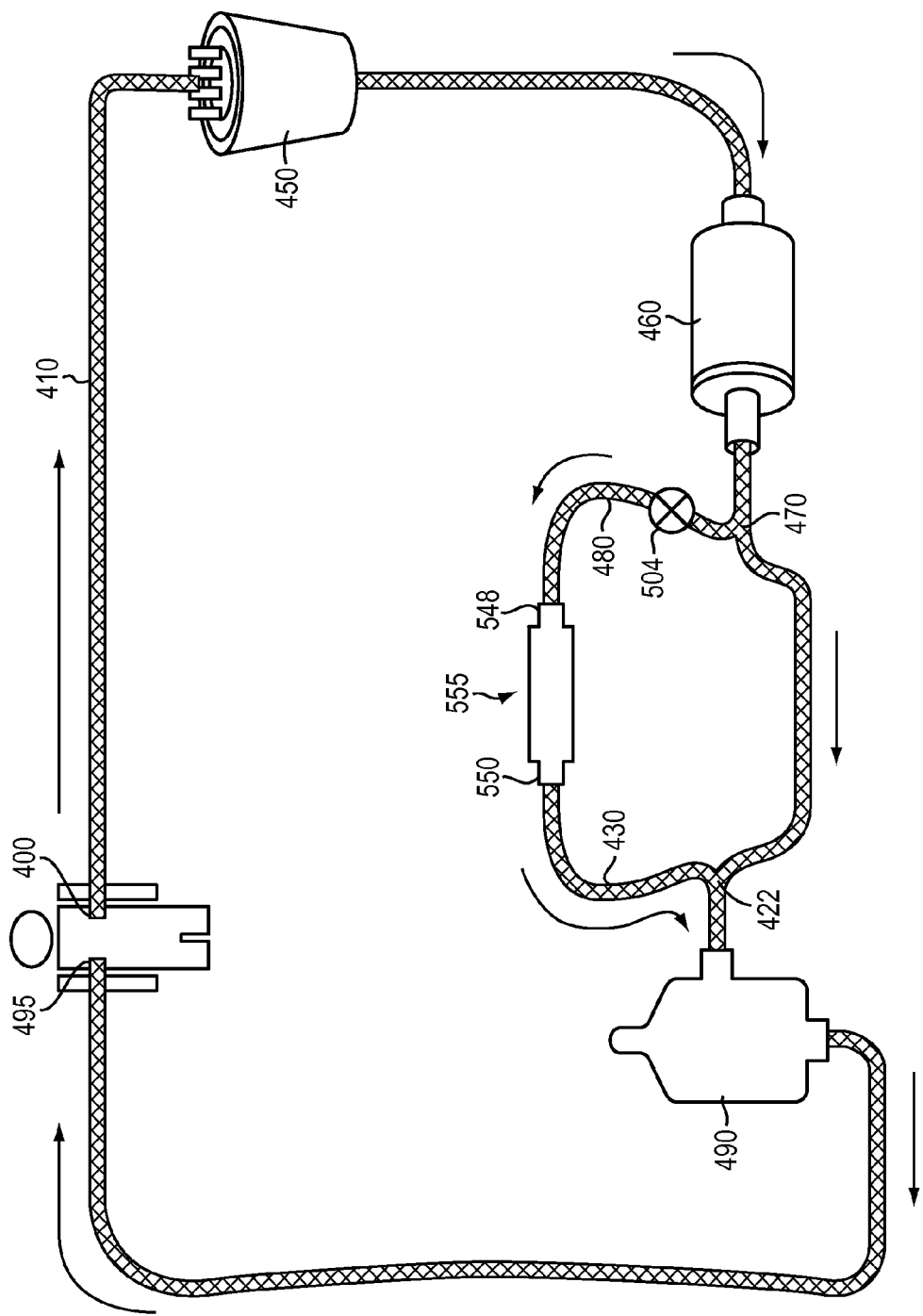
Figure 4E:
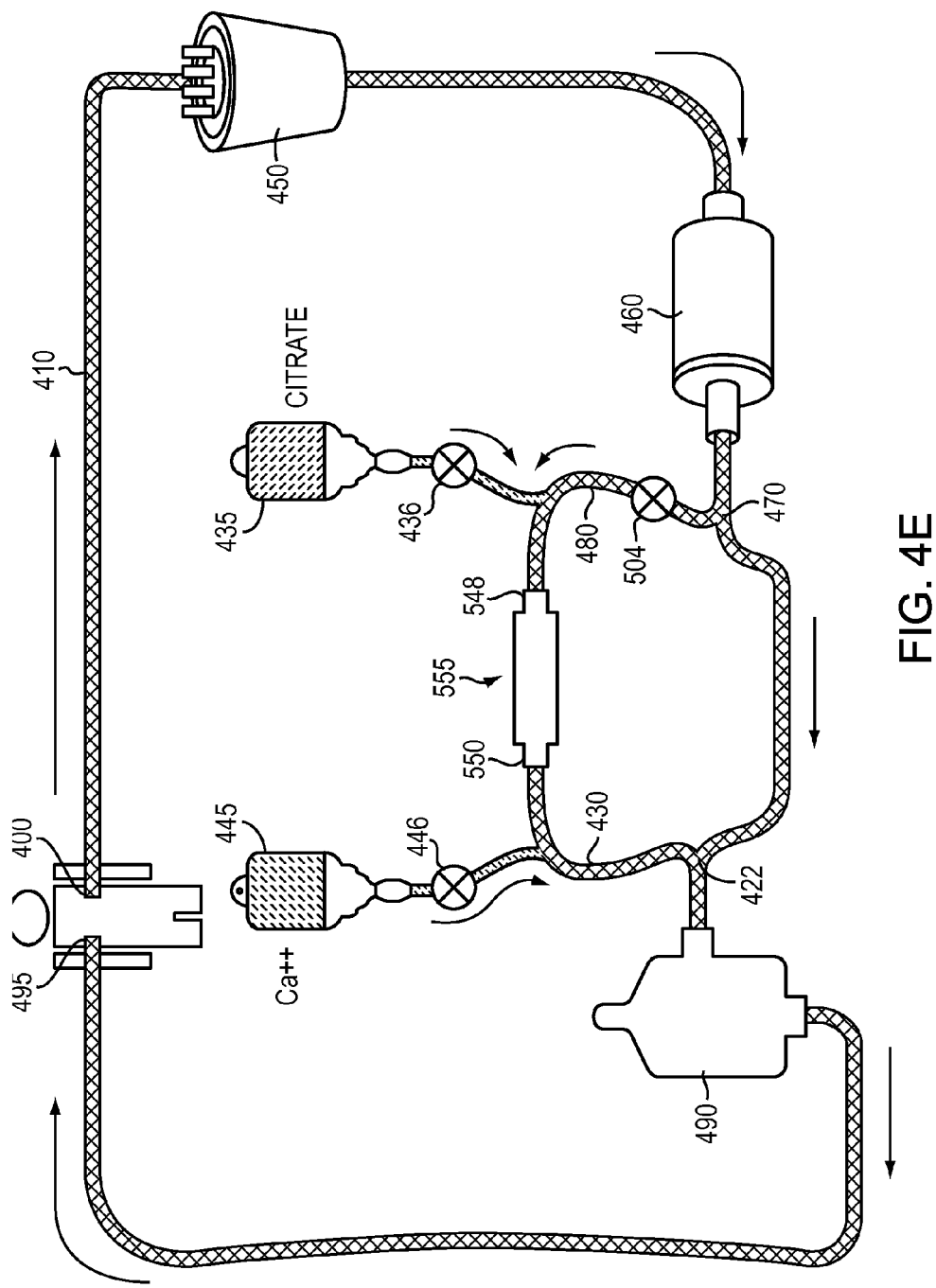
Figure 4F:
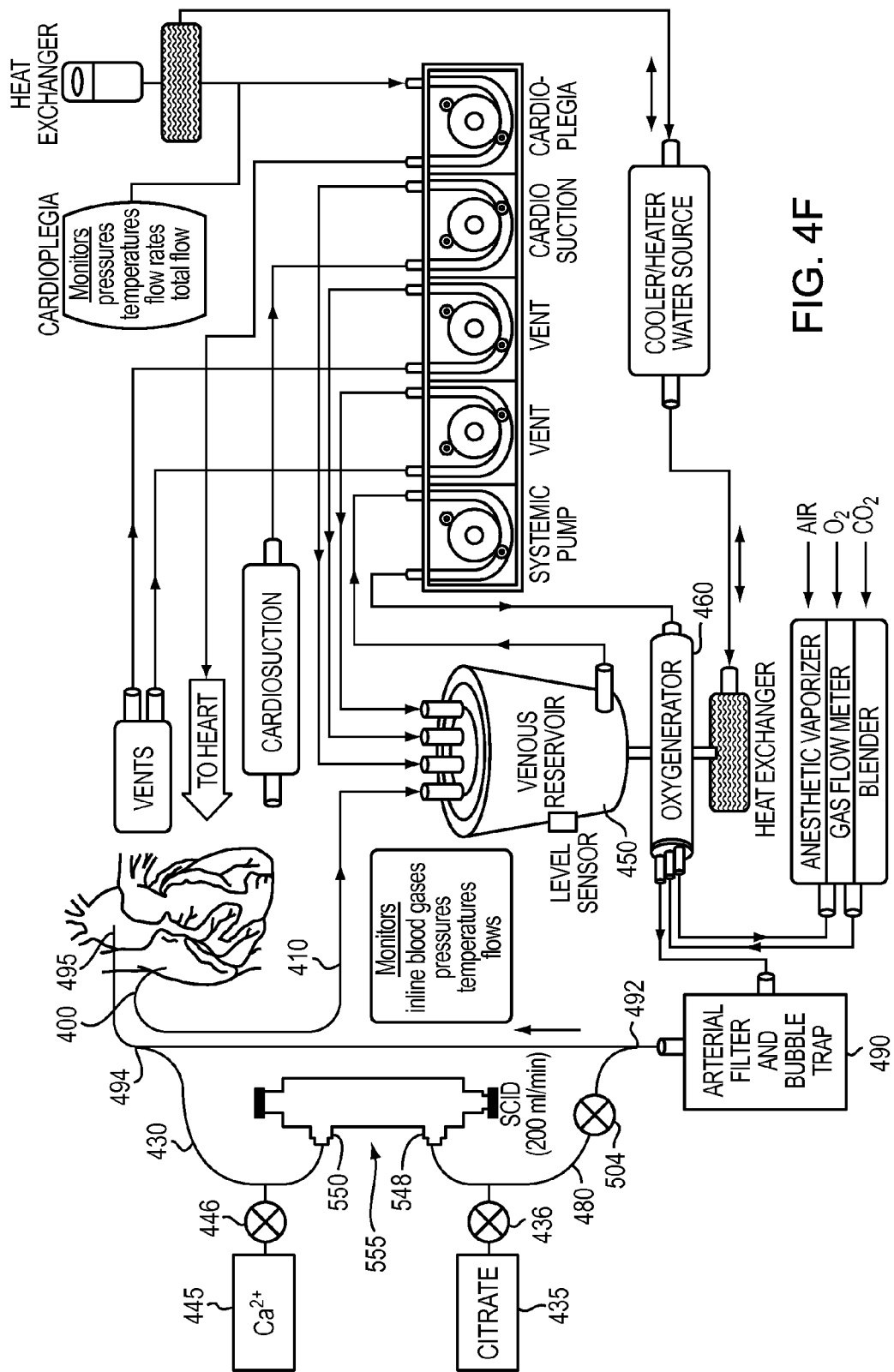

The circuits shown in FIGS. 4D-4F are different from the circuits of FIGS. 4A-4C in that they do not recirculate blood within the circuit, for example, at a recirculation junction 420. Rather, as shown in FIG. 4D, blood is moved via the venous cannula 400 from a subject into the blood line 410, where the blood flows directly to the venous reservoir 450 and onto an oxygenator 460 where the blood is oxygenated. The oxygenated blood then flows from the oxygenator 460 to the junction 470 with the SCID inflow line 480. Here, a portion of the blood in the blood line 410 is diverted to the SCID 555 via the SCID inflow line 480 for sequestration of leukocytes by the SCID 555, as described above for FIG. 4A. Blood exiting the SCID 555 enters the SCID outflow line 430 and mixes with oxygenated blood at junction 422. After blood from the SCID mixes with blood in the blood line 410 it continues in the blood line 410 to the arterial filter/bubble trap 490, before being returned to the subject at the arterial cannula 495.

The circuit in FIG. 4E flows in the same fashion as the circuit in FIG. 4D, with the additional features of a citrate feed 435 and citrate pump 436 to add citrate to the blood in the SCID inflow line 480 and a calcium feed 445 and calcium pump 446 to add calcium to the blood in the SCID outflow line 430. As described for FIG. 4B, citrate or any other leukocyte inhibiting agent is added to the blood from the citrate feed 435 to inhibit and/or deactivate cells associated with inflammation, such as leukocytes. Calcium can be added back into the blood to prepare the blood for reentry into the subject.

The circuit in FIG. 4F flows in a similar fashion as the circuit in FIG. 4E, except that the junction that diverts a portion of the blood from the blood line 410 to the SCID inflow line 480 and the junction which returns SCID-treated blood via the SCID outflow line 430 to the bloodflow line 410, are positioned after the arterial filter/bubble trap 490 in the circuit. These junctions are labeled 492 and 494, respectively. FIG. 4F also depicts other subsystems and features, such as heat exchangers, additional pumps, gas meters and exchangers, and monitors, that can be used in any of the above-identified embodiments. Moreover, the SCID in any of the embodiments described in FIGS. 4A-4F can be configured with characteristics (e.g., configurations of devices such as the SCID, membrane characteristics, flow rates) in accordance with any embodiment described herein.

2.D. Additional Features of Selective Cytopheresis Inhibitory Devices

In some embodiments, the devices of the present invention are configured for treating and/or preventing a certain disorder. It is understood, however, that a number of different configurations can be used to treat and/or prevent a particular disorder.

Moreover, the SCID of any embodiment can be oriented horizontally or vertically and placed in a temperature controlled environment. The temperature of a SCID containing cells preferably is maintained at about 37° C. to about 38° C. throughout the SCID's operation to ensure optimal function of the cells in the SCID. For example, but without limitation, a warming blanket may be used to keep the SCID at the appropriate temperature. If other devices are utilized in the system, different temperatures may be needed for optimal performance.

In some embodiments, the devices and systems of the present invention are controlled by a processor (e.g., computer software). In such embodiments, a device can be configured to detect changes in activated leukocyte levels within a subject and provide such information to the processor (e.g., information as to leukocyte level and/or increased risk for developing an inflammation disorder). In some embodiments, when a certain activated leukocyte level is reached or a subject is deemed at a certain risk for developing an inflammation disorder (e.g., SIRS), the subject's blood is processed through a SCID for purposes of reducing the possibility of developing an inflammation disorder. In some embodiments, the device or system automatically processes the subject's blood through the SCID in response to these measurements. In other embodiments, a health professional is alerted to the elevated leukocyte level or increased risk within the subject, and the professional initiates the treatment.

It is contemplated that the devices of the present invention can be included with various kits or systems. For example, the kits or systems may include the devices of the present invention or various parts of the devices, for example, hollow fiber hemofilter cartridges, leukocyte inhibiting agents (e.g., calcium chelating agents, such as citrate), allographic cells (e.g., renal tubule cells), or other parts. Additionally, the kits or systems may be combined with various surgical instruments necessary for implanting the filtration device into a subject.

3. Sequestration of Cells Associated with Inflammation

While the systems and devices of the present invention should be configured to sequester leukocytes from a subject and ameliorate (e.g., inhibit) their inflammatory activity (e.g., inflammatory response), the systems, devices, and methods of the present invention are not limited to a particular design or technique for sequestering a leukocyte and facilitating inhibition of release of a pro-inflammatory substance from a leukocyte and/or deactivation of a leukocyte. Sequestration of leukocytes (such as activated and/or primed leukocytes) can be achieved with any system, device, or component thereof. The terms "sample" and "specimen" are used in their broadest sense. On the one hand, they are meant to include a specimen or culture. On the other hand, they are meant to include both biological and environmental samples. These terms encompass all types of samples obtained from humans and other animals, including but not limited to, body fluids such as urine, blood, serum, plasma, fecal matter, cerebrospinal fluid (CSF), semen, and saliva, as well as solid tissue. However, these examples are not to be construed as limiting the sample types applicable to the present invention. The term sample in the context of the present specification frequently refers to blood from a subject. The term "blood" refers to any aspect of the blood, for example, whole blood, treated blood, filtered blood, or any liquid derived from blood.

In the systems or devices of the present invention, one or more passageways for flowing a biological sample, or one or more regions thereof, can be configured in any of a variety of ways to sequester leukocytes. If more than one passageway is used, they can be positioned in series and/or in parallel. In some embodiments, one or more passageways may be contained within a cartridge, for example a disposable cartridge. A passageway or a passageway region can be defined by any number of surfaces, for example, 1, 2, 3, 4, 5, 10, 20, 50, 100, or more surfaces. Examples of surfaces include, but are not limited to, the walls of a device, such as cylindrical device walls and flat device walls, and/or the exterior surfaces of the hollow fibers described herein.

The surfaces that define a passageway or passageway region can be selected from a variety of forms that sequester leukocytes. For example, flat surfaces (e.g., sheets), curved surfaces (e.g., hollow tubes or fibers), patterned surfaces (e.g., z-folded sheets or dimpled surfaces), irregularly-shaped surfaces, or other configurations can be used in a passageway (or a region thereof) configured to sequester leukocytes. Any of these surfaces may include pores and be porous, selectively-porous, or semi-porous. For example, the surface can be a membrane. The term "membrane" refers to a surface capable of receiving a fluid on both sides of the surface, or a fluid on one side and gas on the other side of the surface. A membrane typically is porous (e.g., selectively-porous or semi-porous) such that it is capable of fluid or gas flow therethrough. It is understood that the term "porous" as used herein to describe a surface or membrane includes generally porous, selectively-porous and/or semi-porous surfaces or membranes. Moreover, additional surfaces in a passageway or passageway region (that may or may not define the passageway) can facilitate leukocyte sequestration, such as particle (e.g. bead) surfaces, surfaces of one or more projections into the passageway, or surfaces of one or more membranes exposed to the flowing biological sample. These additional surfaces also can be selected from amongst the flat surfaces, curved surfaces, patterned surfaces, irregularly-shaped surfaces, and other configurations described above and the materials described below, and can have the enhancements described below.

Passageway surfaces or passageway region surfaces (e.g., the external surfaces of hollow fibers) that define and/or are part of a passageway or passageway region configured to sequester leukocytes are not limited to a particular type, kind or size, and may be made of any appropriate material. For example, a surface may be any biocompatible polymer comprising one or more of nylon, polyethylene, polyurethane, polyethylene terephthalate (PET), polytetrafluoroethylene (PTFE), polyarylethersulfone, CUPROPHAN (a cellulose regenerated by means of the cuprammonium process, available from Enka), HEMOPHAN (a modified CUPROPHAN with improved biocompatibility, available from Enka), CUPRAMMONIUM RAYON (a variety of CUPROPHAN, available from Asahi), BIOMEMBRANE (cuprammonium rayon available from Asahi), saponified cellulose acetate (such as fibers available from Teijin or CD Medical), cellulose acetate (such as fibers available from Toyobo Nipro), cellulose (such as that are regenerated by the modified cuprammonium process or by means of the viscose process, available from Terumo or Textikombinat (Pima, GDR) respectively), polyacrylonitrile (PAN), polysulphone, acrylic copolymers (such as acrylonitrile-NA-methallyl-sulfonate copolymer, available from Hospal), polycarbonate copolymer (such as GAMBRONE, a fiber available from Gambro), polymethylmethacrylate copolymers (such as fibers available from Toray), and ethylene vinyl copolymer (such as EVAL, a ethylene-vinyl alcohol copolymer available from Kuraray). Alternatively, a surface may be nylon mesh, cotton mesh, or woven fiber. The surface can have a constant thickness or an irregular thickness. In some embodiments, surfaces may include silicon, for example, silicon nanofabricated membranes (see, e.g., U.S. Patent Publication No. 20040124147). In some embodiments, surfaces may include polysulphone fibers. Other suitable biocompatible fibers are known in the art, for example, in Salem and Mujais (1993) Dialysis Therapy 2d Ed., Ch. 5: Dialyzers, Eds. Nissensen and Fine, Hanley & Belfus, Inc., Philadelphia, Pa. Cartridges comprising hollow fibers are not limited to particular dimensions (e.g., length, width, weight, or other dimension).

The passageway can include any combination of surfaces. For example, the surface(s) of a passageway or passageway region can include any combination of flat, curved, patterned, and/or irregularly shaped aspects. Moreover, a passageway or passageway region can be defined by or otherwise include surfaces of more than one material. Further, a passageway may include two or more regions. These different regions can have the same or different surfaces.

As discussed above, one embodiment of the SCID that has been used successfully includes a housing containing hollow fibers. A passageway for blood is defined by the interior of the housing and the exterior of the hollow fibers. Leukocytes from the blood associate with a particular region within the passageway, specifically, with the exterior surface of the hollow fibers. Accordingly, in certain embodiments, a passageway region configured to sequester leukocytes may include a porous membrane that permits smaller molecules to pass therethrough but forces larger molecules and/or cells to flow along the membrane. Moreover, in certain embodiments, the passageway region configured to sequester leukocytes is bounded by a surface of a housing and is bounded by, and may include, the exterior surface or surfaces of hollow fibers configured such that the biological sample (e.g., a subject's blood or filtered blood) flows over these surfaces (i.e., over the hollow fibers). See, for example, FIG. 1. The hollow fibers may be porous, semi-porous, or non-porous and a different fluid (e.g., ultrafiltrate) may optionally flow or be present within the hollow fibers. The fibers can be formed from any suitable material described herein.

In some embodiments, the systems, devices, and methods of the present invention are configured to sequester the leukocytes for any desired amount of time, for example, from 1 to 59 seconds, from 1 to 59 minutes, from 1 to 24 hours, from 1 to 7 days, one or more weeks, one or more months, or one year or more. In some embodiments, the devices are configured to sequester leukocytes for an amount of time sufficient to permit the subsequent inhibition of release of a pro-inflammatory substance from the leukocytes and/or deactivation the leukocytes.

Any technique or combination of techniques that facilitates sequestration of the leukocytes can be used, including, for example, biological, chemical, mechanical and/or physical techniques. In some embodiments, biological or chemical techniques for sequestration can be used. Such techniques include using tissues, cells, biomolecules (for example, proteins or nucleic acids), or small molecules to sequester leukocytes. When a leukocyte is activated, selectins are produced by the leukocyte. This altered selectin production can facilitate binding between the leukocyte and other leukocytes. In turn, the binding between leukocytes can increase selectin production in the additionally bound leukocytes, yielding exponential binding of leukocytes. Thus, selectins may be useful to enhance sequestration. Proteins, protein complexes, and/or protein components known to bind leukocytes include CD11a, CD11b, CD11c, CD18, CD29, CD34, CD44, CD49d, CD54, podocalyxin, endomucin, glycosaminoglycan cell adhesion molecule-1 (GlyCAM-1), mucosal addressin cell adhesion molecule-1 (MAdCAM-1), E-selectin, L-selectin, P-selectin, cutaneous lymphocyte antigen (CLA), P-selectin glycoprotein ligand 1 (PSGL-1), leukocyte functional antigen-1 (LFA-1), Mac-1, leukocyte surface antigen p150,95, leukocyte integrin CR4, very late antigen-4 (VLA-4), lymphocyte Peyers patch adhesion molecule-1 (LPAM-1), intracellular adhesion molecule-1 (ICAM-1), intracellular adhesion molecule-2 (ICAM-2), intracellular adhesion molecule-3 (ICAM-3), inactivated C3b (C3bi), fibrinogen, fibronectin, peripheral lymph node addressin (PNAd), endothelial vascular adhesion protein 1 (VAP-1), fractalkine, CCL19, CCL21, CCL25, and CCL27. Other large molecules known to bind leukocytes include hyaluronic acid, glycosaminoglycans (GAGs), and fucosylated oligosaccharides and their precursors. In certain embodiments, small molecules or adherents used to sequester a leukocyte can include, but are not limited to, peptides, such as peptides comprising the amino acid sequence arginine-glycine-aspartic acid (RGD), and molecules comprising sialic acid. Accordingly, any of these materials can be used to enhance sequestration.

In use, any of these biological or chemical materials may be bound to a surface of a system or device of the present invention (e.g., within a passageway of a SCID) to facilitate or enhance sequestration. Alternatively or in combination, any of these materials may be in solution in a system or device of the present invention. In this instance, the materials may sequester leukocytes in conjunction with additional techniques. For example, these materials may bind leukocytes in solution, agglomerating them to increase overall size relative to the size of a single leukocyte. The agglomerated leukocytes then can be captured with a membrane having a particular pore size.

In some embodiments, a system or device of the present invention accomplishes retention of leukocytes through control of mechanical forces. For example, leukocytes may be sequestered on one or more surfaces of (or in) a passageway or passageway region (e.g., the outside of a porous hollow fiber) by utilizing a flow rate and device configuration that minimizes shear force between the leukocytes and the surface(s), allowing the leukocytes to associate with the surface(s). Useful shear forces between the flowing leukocytes and the sequestration surface(s) include a shear force of less than 1000 dynes/cm$^2$, or less than 500 dynes/cm$^2$, or less than 100 dynes/cm$^2$, or less than 10 dynes/cm$^2$, or less than 5 dynes/cm$^2$. Exemplary flow rates of blood through systems and devices according to the invention that are useful to achieve these shear forces include, for example, less than about 500 mL/minute, from about 100 mL/minute to about 500 mL/minute, and from about 200 mL/minute to about 500 mL/minute.

In some embodiments, a device may physically retain the leukocytes, for example, at one or more passageway surfaces, or regions thereof, by using surfaces such as membranes or filters or by exposing the leukocytes to increased passageway surface area, for example, a surface area greater than about 0.2 m$^2$, or from about 0.2 m$^2$ to about 2.0 m$^2$, or from about 0.5 m$^2$ to about 1.0 m$^2$, or about 0.7 m$^2$, so as to increase the amount of leukocytes that are sequestered and/or the time that a leukocyte is sequestered within the device.

In some embodiments, a system can achieve sequestration by subjecting the leukocytes to a series of devices, for example, 2, 4, 10, 20, or more cartridges (e.g., hollow fiber cartridges), each comprising one or more sequestration passageways, or passageway regions, so as to increase the length of the region configured to sequester the leukocytes and the residence time of the leukocytes therein. In any of the aforementioned embodiments, the devices are configured to accomplish sequestration of leukocytes in a manner permitting inhibition of release of a pro-inflammatory substance from a leukocyte and/or deactivation of a leukocyte before, during, or after sequestering. Inhibition of release of a pro-inflammatory substance from a leukocyte and/or deactivation of a leukocyte can be achieved both during sequestration and during transport through a passageway, passageway region, or entire system of the present invention.

It should be understood that the sequestration techniques described herein also can apply to platelets. In the case of platelets, similar bioglocial, chemical, mechanical and/or physical techniques as described above may be used to sequester platelets. In certain embodiments, agents used to sequester platelets include one or more of glycoprotein Ibα (GPIbα), glycoprotein IIb (GPIIb), glycoprotein IIIa (GPIIIa), CD41, CD61, von Willebrand Factor, $β_2$-integrin macrophage antigen-1, selectins such as P-selectin, and a cell-adhesion molecule.

4. Inhibition and/or Deactivation of Cells Associated with Inflammation

The systems and devices of the present invention are configured, and the methods of the present invention are designed, to inhibit release of a pro-inflammatory substance from leukocytes and/or deactivate leukocytes, such as primed or activated leukocytes, in a subject's blood such that an inflammatory response within the subject is prevented and/or diminished. Various techniques can be used. For example, in some embodiments, the devices and systems can inhibit release of a pro-inflammatory substance from a leukocyte and/or deactivate a leukocyte by exposing the leukocytes (e.g., sequestered activated and/or primed leukocytes) to leukocyte inhibiting agents. A leukocyte inhibiting agent can be bound, covalently or noncovalently, to a surface of a passageway, for example, a hollow fiber. Additionally or alternatively, a leukocyte inhibiting agent can be infused into the device or system before, during, or after sequestration of the leukocytes, for example, at or near a membrane surface. As mentioned, the proof-of-concept SCID treated leukocytes with citrate, leading to increased subject survival.

The present invention is not limited to a particular type or kind of leukocyte inhibiting agent. Leukocyte inhibiting agents include, for example, anti-inflammatory biological agents, anti-inflammatory small molecules, anti-inflammatory drugs, anti-inflammatory cells, and anti-inflammatory membranes. In some embodiments, the leukocyte inhibiting agent is any material or compound capable of inhibiting activated leukocyte activity including, but not limited to, non-steroidal anti-inflammatory drugs (NSAIDs), anti-cytokines, imatinib mesylate, sorafenib, sunitinib malate, anti-chemokines, immunosuppressant agents, serine leukocyte inhibitors, nitric oxide, polymorphonuclear leukocyte inhibitor factor, secretory leukocyte inhibitor, and calcium chelating agents. Examples of calcium chelating agents include, but are not limited to, citrate, sodium hexametaphosphate, ethylene diamine tetra-acetic acid (EDTA), triethylene tetramine, diethylene triamine, o-phenanthroline, oxalic acid and the like. The leukocyte inhibiting agent can be any protein or peptide known to inhibit leukocytes or immune cells including, but not limited to, angiogenin, MARCKS, MANS, Complement Factor D, the disulfide C39-C92 containing tryptic angiogenin fragment LHGGSPWPPC$^{92}$QYRGLTSPC$^{39}$K (SEQ ID NO: 1) and synthetic homologs of the same; the agent also can be those proteins, peptides, and homologs reported by Tschesche et al. (1994) J. Biol. Chem. 269(48): 30274-80, Horl et al. (1990) PNAS USA 87: 6353-57, Takashi et al. (2006) Am. J. Respirat. Cell and Molec. Biol. 34: 647-652, and Balke et al. (1995) FEBS Letters 371: 300-302, that may facilitate inhibition of release of a pro-inflammatory substance from a leukocyte and/or deactivate a leukocyte. Moreover, the leukocyte inhibiting agent can be any nucleic acid known to inhibit release of a pro-inflammatory substance from the leukocyte and/or deactivate the leukocyte. The leukocyte inhibiting agent can be in solution or lyophilized.

Any amount or concentration of leukocyte inhibiting agent can be used to inhibit the release of pro-inflammatory substances from a leukocyte and/or deactivate the leukocyte. The leukocyte inhibiting agent can be introduced into a passageway, passageway region, device, device region, or system region of a system by any methods known in the art. For example, the leukocyte inhibiting agent can be infused at a port. The amount of leukocyte inhibiting agent infused in a passageway can be sufficient to inhibit release of a pro-inflammatory substance from a leukocyte and/or deactivate a leukocyte sequestered within the same passageway or within an adjacent passageway. In some embodiments, a leukocyte inhibiting agent, for example, citrate, can be infused into the system, a region of the system, or one or more devices within the system, including devices that perform other functions and do not sequester leukocytes. More particularly, the leukocyte inhibiting agent (e.g. citrate) can be infused upstream from, into, or downstream from a passageway that sequesters leukocytes. Alternatively, the leukocyte inhibiting agent can be contained in one or more passageways, passageway regions, devices, or system regions within a system. For example, a leukocyte inhibiting agent can be bound to a surface in the passageway configured to sequester leukocytes, or in another passageway, in an amount sufficient to inhibit release of a pro-inflammatory substance from the leukocytes and/or deactivate the leukocytes.

The inhibition of release of a pro-inflammatory substance from a leukocyte and/or deactivation of a leukocyte can occur temporally before, during, and/or after sequestration of the leukocyte. Moreover, the leukocyte can remain inhibited or deactivated for a period of time following sequestration. In certain embodiments, a leukocyte can be inhibited or deactivated during the period of time that the leukocyte is exposed to a target concentration of a leukocyte inhibiting agent or is exposed to a target a concentration of $Ca_i$ (typically from about 0.20 mmol/L to about 0.40 mmol/L) that results from exposure to a leukocyte inhibiting agent such as citrate. The period of time that the leukocyte is exposed to the target concentration of leukocyte inhibiting agent or target concentration of $Ca_i$ can precede, include, and/or follow the period of time that the leukocyte is sequestered. In certain embodiments, the leukocyte can continue to become or remain inhibited or deactivated for a period of time following exposure to the leukocyte inhibiting agent.

The time of exposure to the leukocyte inhibiting agent can vary depending upon the agent used, the extent of leukocyte activation, the extent of production of pro-inflammatory substances, and/or the degree to which the inflammatory condition has compromised patient health. Exposure can be, for example, from 1 to 59 seconds, from 1 to 59 minutes, from 1 to 24 hours, from 1 to 7 days, one or more weeks, one or more months, or one year or more. The leukocyte inhibiting agent can be applied to the system before or during operation the system. In certain embodiments, the leukocyte inhibiting agent is applied during operation of the system and the amount of leukocyte inhibiting agent applied to the system is monitored.

In some embodiments, a leukocyte inhibiting agent can be titrated into the system (e.g., at a port 206 as shown in FIGS. 2A-2D and 3 or from a feed 435 and pump 436 as shown in FIGS. 4B, 4C, 4E, and 4F). The titration can be adjusted relative to a monitored blood characteristic. For example, citrate can be titrated into the system to keep the $Ca_i$ in the blood at a certain level, for example, at a $Ca_i$ concentration of about 0.2 to about 0.4 mmol/L. Any type of citrate that is biologically compatible can be used, for example, 0.67% trisodium citrate or 0.5% trisodium citrate. See, e.g., Tolwani et al. (2006) Clin. J. Am. Soc. Nephrol. 1: 79-87. In some embodiments, a second solution can be added into the system following inhibition of the release of pro-inflammatory substances from a leukocyte and/or deactivation of the leukocyte (e.g., at port 258 as shown in FIGS. 2A-2D and 3, or from a feed 445 and pump 446 as shown in FIGS. 4B, 4C, 4E, and 4F), to readjust the blood for reentry into the subject. For example, in embodiments in which a calcium chelating agent is used as the leukocyte inhibiting agent, calcium can be added back into the blood before reentry into the subject.

In one embodiment, a 1000 mL bag containing a citrate solution, for example ACD-A (Baxter Fenwal, Chicago Ill.; contents per 100 mL: dextrose 2.45 g, sodium citrate 2.2 g, citric acid 730 mg, pH 4.5-5.5 at 25° C.) can be attached to an infusion pump and then attached to an arterial line (outflow from subject to devices) of the system (e.g. at port 206; the outflow from a subject in a CPB situation is called a venous line, and infusion occurs from, for example, the feed 435 and pump 436). A negative pressure valve can be employed to facilitate citrate pump function (infusing into a negative pressure area proximal to the blood pump). The initial rate of citrate infusion can be constant, for example, about 1.5 times, in mL/hour, the blood flow rate, in mL/minute (e.g., if the blood flow rate is about 200 mL/minute, then the initial constant rate of citrate infusion may be about 300 mL/hour). In addition, a calcium chloride infusion at a concentration of about 20 mg/mL may be added near the venous port of the system (e.g., port 258; the analogous location in the CPB situation is shown as a feed 445 and pump 446 in FIGS. 4B, 4C, 4E, and 4F). The initial calcium infusion can be set at 10% of the citrate infusion rate (e.g., 30 mL/hour). The $Ca_i$ can be monitored continuously or at various times, for example, every two hours for the first eight hours, then every four hours for the next sixteen hours, then every six to eight hours thereafter. The monitoring can be increased as needed and can be monitored at more than one location in the system, for example, after citrate infusion and after calcium infusion.

Exemplary citrate and calcium chloride titration protocols are shown in Table 1 and in Table 2, respectively. In this embodiment, the target $Ca_i$ range in the SCID is from about 0.20 mmol/L to about 0.40 mmol/L, with the $Ca_i$ target concentration achieved by infusion of citrate (e.g., ACD-A citrate solution). As this is a dynamic process, the rate of citrate infusion may need to changed to achieve the target $Ca_i$ range in the SCID. The protocol for doing so is shown below, with infusion occurring at the infusion points described above.

TABLE 1

Citrate Infusion Titration Guidelines

| Circuit Ionized $Ca^{2+}$ (between the SCID and patient) | Infusion Adjustment with ACD-A citrate solution (as described above) |
|---|---|
| If circuit ionized $Ca^{2+}$ is less than 0.20 mmol/L | then decrease the rate of citrate infusion by 5 mL/hour |
| If circuit ionized $Ca^{2+}$ is 0.20-0.40 mmol/L (Optimal Range) | then make no change to the rate of citrate infusion |
| If circuit ionized $Ca^{2+}$ is 0.41-0.50 mmol/L | then increase the rate of citrate infusion by 5 mL/hour |
| If circuit ionized $Ca^{2+}$ is greater than 0.50 mmol/L | then increase the rate of citrate infusion by 10 mL/hour |

TABLE 2

Calcium Infusion Titration Guidelines

| Patient Ionized $Ca^{2+}$ (drawn systemically from patient) | $Ca^{2+}$ Infusion (20 mg/mL $CaCl_2$) Adjustment |
|---|---|
| If patient ionized $Ca^{2+}$ is greater than 1.45 mmol/L | then decrease the rate of $CaCl_2$ infusion by 10 mL/hour |
| If patient ionized $Ca^{2+}$ is 1.45 mmol/L (maximum allowable amount) | then decrease the rate of $CaCl_2$ infusion by 5 mL/hour |
| If patient ionized $Ca^{2+}$ is 0.9 mmol/L (minimum allowable amount) | then increase the rate of $CaCl_2$ infusion by 5 mL/hour |
| If patient ionized $Ca^{2+}$ is less than 0.9 mmol/L | then administer a 10 mg/kg $CaCl_2$ bolus and increase the rate of $CaCl_2$ infusion by 10 mL/hour |
| Default Range (preferred target level) | 1.0-1.2 mmol/L |

It should be understood that the deactivation techniques described herein also can apply to platelets. In certain embodiments, agents used to deactivate a platelet and/or inhibit release of a pro-inflammatory substance from a platelet include, but are not limited to, agents that inhibit thrombin, antithrombin III, meglatran, herudin, Protein C and Tissue Factor Pathway Inhibitor. In addition, some leukocyte inhibiting agents can act as platelet inhibiting agents. For example, calcium chelating agents, such as citrate, sodium hexametaphosphate, ethylene diamine tetra-acetic acid (EDTA), triethylene tetramine, diethylene triamine, o-phenanthroline, and oxalic acid can deactivate a platelet and/or inhibit release of a pro-inflammatory substance from a platelet.

5. Indications

The methods, devices, and systems of the present invention can be used for treating and/or preventing a number of conditions that are associated with inflammation. As used herein, the term "inflammatory condition," includes any inflammatory disease, any inflammatory disorder, and/or any leukocyte activated disorder wherein the organism's immune cells are activated. Such a condition can be characterized by (i) a persistent inflammatory response with pathologic sequelae and/or (ii) infiltration of leukocytes, for example, mononuclear cells and neutrophils, leading to tissue destruction. Inflammatory conditions include primary inflammatory diseases arising within a subject and/or secondary inflammatory disorders arising as a response to a medical procedure. The systems, devices, and methods of the present invention can treat any inflammatory condition for any subject. As used herein, the term "subject" refers to any animal (e.g., a mammal), including, but not limited to, a human (e.g., a patient), a non-human primate, a rodent, and the like, which is to be the recipient of a particular diagnostic test or treatment.

Leukocytes, for example, neutrophils, are major contributors to the pathogenesis and progression of many clinical inflammatory conditions, including systemic inflammatory response syndrome (SIRS), sepsis, ischemia/reperfusion injury and acute respiratory distress syndrome (ARDS). Several different and diverse types of leukocytes exist; however, they are all produced and derived from a pluripotent cell in the bone marrow known as a hematopoietic stem cell.

Leukocytes, also referred to as white blood cells, are found throughout the body, including in the blood and lymphatic system. There are several different types of leukocytes including granulocytes and agranulocytes. Granulocytes are leukocytes characterized by the presence of differently staining granules in their cytoplasm when viewed under light microscopy. These granules contain membrane-bound enzymes, which primarily act in the digestion of endocytosed particles. There are three types of granulocytes: neutrophils, basophils, and eosinophils, which are named according to their staining properties. Agranulocytes are leukocytes characterized by the absence of granules in their cytoplasm and include lymphocytes, monocytes, and macrophages.

Platelets, or thrombocytes, also contribute to inflammatory conditions, as well as to homeostasis. Upon activation, platelets aggregate to form platelet plugs, and they secrete cytokines and chemokines to attract and activate leukocytes. Platelets are found throughout the body's circulation and are derived from megakaryocytes.

The molecules that are primarily responsible for initiation of leukocyte and platelet adhesion to endothelium are P-selectin and von Willebrand factor, respectively. These molecules are found in the same granules, known as Weibel-Palade bodies, in endothelial cells. Upon activation of endothelial cells, the Weibel-Palade bodies migrate to the cell membrane to expose P-selectin and soluble von Willebrand factor at the endothelial cell surface. This, in turn, induces a cascade of leukocyte and platelet activity and aggregation.

Accordingly, the systems, devices, and methods of the present invention can treat and/or prevent any inflammatory condition, including primary inflammatory diseases arising within a subject and/or secondary inflammatory disorders arising as a response to a medical procedure (e.g., dialysis or cardio-pulmonary bypass). Examples of applicable inflammatory conditions, including inflammatory diseases and/or disorders, include, but are not limited to, systemic inflammatory response syndrome (SIRS), cardiopulmonary bypass syndrome, acute respiratory distress syndrome (ARDS), sepsis, systemic lupus erythematosis, inflammatory bowel disease, pancreatitis, nephritis, multiple sclerosis, psoriasis, allograft rejection, asthma, chronic renal failure, cardiorenal syndrome, hepatorenal syndrome, and any acute organ failure from ischemic reperfusion injury to myocardium, central nervous system, liver, lungs, kidney, or pancreas.

Additional examples of inflammatory conditions include, but are not limited to, transplant (such as organ transplant, acute transplant, xenotransplant) or heterograft or homograft (such as is employed in burn treatment) rejection; ischemic or reperfusion injury such as ischemic or reperfusion injury incurred during harvest or organ transplantation, myocardial infarction or stroke; transplantation tolerance induction; arthritis (such as rheumatoid arthritis, psoriatic arthritis or osteoarthritis); respiratory and pulmonary diseases including but not limited to chronic obstructive pulmonary disease (COPD), emphysema, and bronchitis; ulcerative colitis and Crohn's disease; graft vs. host disease; T-cell mediated hypersensitivity diseases, including contact hypersensitivity, delayed-type hypersensitivity, and gluten-sensitive enteropathy (Celiac disease); contact dermatitis (including that due to poison ivy); Hashimoto's thyroiditis; Sjogren's syndrome; Autoimmune Hyperthyroidism, such as Graves' Disease; Addison's disease (autoimmune disease of the adrenal glands); Autoimmune polyglandular disease (also known as autoimmune polyglandular syndrome); autoimmune alopecia; pernicious anemia; vitiligo; autoimmune hypopituatarism; Guillain-Barre syndrome; other autoimmune diseases; glomerulonephritis; serum sickness; uticaria; allergic diseases such as respiratory allergies (hayfever, allergic rhinitis) or skin allergies; scleroderma; mycosis fungoides; acute inflammatory and respiratory responses (such as acute respiratory distress syndrome and ischemia/reperfusion injury); dermatomyositis; alopecia greata; chronic actinic dermatitis; eczema; Behcet's disease; Pustulosis palmoplanteris; Pyoderma gangrenum; Sezary's syndrome; atopic dermatitis; systemic sclerosis; morphea; trauma, such as trauma from a gun, knife, automobile accident, fall, or combat; and cell therapy, such as autologous, allogenic or xenogenic cell replacement. Additional inflammatory conditions are described elsewhere herein or are otherwise known in the art.

The systems, devices, and methods of the present invention may also be used to support the development and use of tissues and organs ex vivo. For example, the present invention may be used to support organ harvesting procedures for transplantation, tissue engineering applications, ex vivo generation of organs, and the manufacture of and use of bio-microelectromechanical systems (MEMs).

In light of the foregoing description, the specific non-limiting examples presented below are for illustrative purposes and not intended to limit the scope of the invention in any way.

EXAMPLES

Example 1

Treatment of Inflammation Associated with Acute Sepsis and Acute Renal Failure in an Animal Model This example describes a series of experiments used to evaluate an embodiment of the present invention to treat inflammation associated with the conditions of acute sepsis and acute renal failure.

(I) Background and Rationale

Leukocytes, especially neutrophils, are major contributors to the pathogenesis and progression of many clinical inflammatory disorders, including SIRS, sepsis, ischemia/reperfusion injury and acute respiratory distress syndrome (ARDS). A large number of therapeutic approaches are under investigation to limit the activation and tissue accumulation of leukocytes at sites of inflammation in order to minimize tissue destruction and disease progression. Severe sepsis with SIRS occurs in 200,000 patients annually in the U.S. with a mortality rate of 30-40%, even with use of intensive care units and broad spectrum antibiotics.

The origins of this research emanate from ongoing encouraging pre-clinical and clinical studies utilizing renal tubule progenitor cells in an extracorporeal device to treat acute renal failure (ARF). ARF arises from acute tubular necrosis (ATN) secondary to nephrotoxic and/or ischemic renal tubule cell injury in a cascade of events culminating in multi-organ failure and death. Mortality rates from ATN requiring renal replacement therapy range from 50 to 70 percent. This high mortality rate has persisted over the last several decades despite greater understanding of the pathophysiology of the disorder and improvements in hemodialysis and hemofiltration therapy.

The utilization of renal tubule progenitor cells as a therapy for these conditions was based upon the thesis that renal tubule cells play an important immunologic regulatory role in septic shock. Specifically, severe septic shock has been shown to result in acute tubular necrosis (ATN) and ARF within hours of bacteremia in a porcine model of septic shock. Thus, ARF develops early in the time course of septic shock, a time frame not appreciated clinically since it takes several days to observe a rise in blood urea nitrogen and serum creatinine after the acute insult. The loss of the kidney's immunoregulatory function in ARF and ATN results in a propensity to develop SIRS, sepsis, multiorgan failure and a high risk of death. A recent report has demonstrated a rise in sepsis events from 3.3% to nearly 60% in patients who develop ARF during the post-op course following open heart surgery.

The disorder of ARF, or ATN, may be especially amenable to therapy in conjunction with continuous hemofiltration techniques, since acute hemodialysis or hemofiltration alone has yet to reduce the mortality rate of ATN below 50 percent, despite advances in synthetic materials and extracorporeal circuits. ATN develops predominantly due to the injury and necrosis of renal proximal tubule cells. The early replacement of the functions of these cells during the episode of ATN, which develops concurrently with septic shock, may provide almost full renal replacement therapy in conjunction with hemofiltration. The addition of metabolic activity, such as ammoniagenesis and glutathione reclamation, endocrine activity, such as vitamin D3 activation, and cytokine homeostasis may provide additional physiological replacement activities to change the current natural history of this disease progression.

One system used to test the effects of renal tubule progenitor cells on this condition consisted of a filtration device (a conventional high-flux hemofilter) followed in series by a renal assist device (RAD), generally as described in U.S. Pat. No. 6,561,997. In those earlier experiments, a RAD referred to an extracorporeal system utilizing a standard hemofiltration cartridge containing human renal epithelial cells grown along the inner surface of the fibers. This arrangement allowed the filtrate to enter the internal compartments of the hollow fiber network, lined with renal tubule cells for regulated transport and metabolic function. Blood pumped out of the subject entered the fibers of the first hemofilter, where ultrafiltrate (UF) was formed and delivered into the lumens of the hollow fibers within the RAD downstream of the hemofilter. Processed UF exiting the RAD was collected and discarded as "urine." The filtered blood exiting the initial hemofilter entered the RAD through the extracapillary space (ECS) port and dispersed among the fibers of the device. Upon exiting the RAD, the processed blood was returned to the subject's body via a third pump. That extracorporeal blood circuit was based upon blood pump systems and blood tubing identical to those used for continuous or intermittent hemodialysis therapy in patients with renal failure.

In vitro studies of renal tubule progenitor cells in the RAD demonstrated that the cells retained differentiated active transport properties, differentiated metabolic activities and important endocrine processes. Additional studies showed that the RAD, when incorporated in series with a hemofiltration cartridge in an extracorporeal blood perfusion circuit, replaced filtration, transport, metabolic, and endocrine functions of the kidney in acutely uremic dogs. Furthermore, the RAD ameliorated endotoxin shock in acutely uremic animals.

To better understand the immunoregulatory role of renal tubule cell therapy, the tissue-specific consequences of sepsis with or without RAD therapy were evaluated with bronchoalveolar lavage (BAL). BAL specimens were used to assess pulmonary microvascular damage and inflammation in response to SIRS. Preliminary data detailed below demonstrated that renal cell therapy was associated with less protein leak from damaged blood vessels and less inflammation.

With this experimental model system, the role of renal cell therapy on systemic and tissue-specific inflammatory processes could be more carefully evaluated in a second series of evaluations. At the same time, in the clinical trials evaluating the RAD, a barrier to enrollment was the requirement for systemic anticoagulation with heparin to maintain blood perfusion of the extracorporeal blood lines and dialysis cartridges. Over the last decade, to relieve the requirement for systemic heparinization and better maintenance of blood perfusion in continuous renal replacement therapy (CRRT) circuits, regional anticoagulation with citrate as a calcium binder has become a standard therapeutic modality.

Thus, a comparison in pre-clinical animal models using sham non-cell cartridges and cell-containing cartridges was performed to confirm that citrate and low $Ca_i$ levels in the blood circuit did not reduce the efficacy of renal tubule cell therapy observed with systemic heparin treatment. As detailed below, citrate anticoagulation in a two-cartridge system showed profound and unexpected results.

(II) Experiment A—Initial Experiment of the Animal Model

To initially evaluate an embodiment of the present invention, an established reproducible model of SIRS in a porcine model of sepsis was employed. (See, e.g., Humes et al. (2003) Crit. Care Med. 31:2421-2428.)

Methods and Materials

Normal pigs (30-35 kg) were prepared by the introduction of appropriate catheters to assess cardiovascular parameters and treatment with continuous venovenous hemofiltration (CVVH). The pigs then received intraperitoneally $30 \times 10^{10}$ bacteria/kg body weight of E. coli. Within 15 minutes after bacteria infusion, the animals were placed in a CVVH circuit with two cartridges, the first being a hemofilter and the second being a renal assist device (RAD) comprising porous, hollow fibers. For this experiment, the RAD refers to the device shown schematically in FIG. 7 in the circuit shown in FIG. 3. In FIG. 7, the RAD contains a plurality of membranes, which are hollow fibers 752 (only one is labeled for clarity). The luminal space within the fibers is called the intracapillary space ("ICS") 740. The surrounding space is called the extracapillary space ("ECS") 742 within a housing 754 of the RAD. Blood containing activated leukocytes enters the ECS inlet 748, moves into the ECS 742 surrounding the fibers 752, and exits the RAD via the ECS outlet 750, which enters into an outflow line. For this experiment, the hollow fibers 752 of the RAD are porous and contain allographic renal tubule cells, cultured in a monolayer on the lining of the lumen 740 of each fiber. The control was a sham-RAD that contained no renal tubule cells but was otherwise the same as the RAD.

As shown in FIG. 3, blood exiting the animals was pumped into the fibers of the first hemofilter, where ultrafiltrate (UF) was formed and delivered into the ICS 740 within the RAD hollow fibers 752 downstream of the hemofilter. Processed UF exiting the RAD was collected and discarded as waste using a UF pump 304. The filtered blood exiting the initial hemofilter entered the RAD through the extracapillary space (ECS) inlet 748 and dispersed among the fibers 752 of the device. Upon exiting the RAD via ECS outlet 750, the processed blood was returned to the subject's body. The blood moved through the system via blood pumps 204 and 300 placed before and after the hemofiltration device and a third blood pump (not shown in FIG. 3) placed between the RAD and the animal. Citrate or heparin was added to the system at 206 and, if necessary, a second agent (to prepare the blood for re-entry) was added at 258 before re-entry of the blood into the subject.

During the first hour following bacteria infusion, animals were resuscitated with volume consisting of 80 mL/kg of crystalloid and 80 mL/kg of colloid (Hepspan). At 15 minutes following bacteria infusion, animals received 100 mg/kg of the antibiotic Ceftriaxone to replicate the clinical situation. No animals received vasopressor or inotropic agents.

Results and Discussion

Blood pressure, cardiac output, heart rate, pulmonary capillary wedge pressure, systemic vascular resistance and renal blood flow were measured throughout the study. Using this model, it was shown that RAD treatment maintained better cardiovascular performance over controls as determined by cardiac output and renal blood flow. The improved renal blood flow was due to a lower renal vascular resistance in RAD animals compared to controls.

The improved cardiovascular parameters resulted in greater survival times. Control animals (treated with a sham-RAD, which has no renal tubule cells) all expired within 7 hours, whereas all RAD-treated animals survived greater than 7 hours. The RAD group survived 10±2 hours compared to 5±1 hour in the controls (p<0.02). Plasma levels of interleukin (IL-6), a prognostic inflammatory indication in septic shock, as well as interferon-gamma (IFN-γ), an initiator of the cytokine inflammatory response, were lower in the RAD group compared to the control group.

The initial data demonstrated that the porcine model was a dependable model of acute septic shock and that RAD treatment improved cardiovascular performance associated with changes in cytokine profiles and resulted in a significant survival advantage. The initial data also demonstrated that RAD therapy can ameliorate the multiorgan dysfunction that arises in septic shock.

To improve the reproducibility of this model, the volume resuscitation protocol was increased from 100 mL/hour to 150 mL/hour immediately after the crystalloid/colloid bolus infusion at the time of bacteria administration. In addition to this improved resuscitation protocol, the tissue-specific consequences of sepsis with or without RAD therapy were evaluated with bronchoalveolar lavage (BAL) to better understand the immunoregulatory role of renal tubule cell therapy. BAL specimens were used to assess pulmonary microvascular damage and inflammation in response to SIRS. It was shown that renal cell therapy was associated with less protein leak from damaged blood vessels and less inflammation in BAL fluid samples as well as improvement of other cardiovascular effects of SIRS.

The above described refined animal model utilizing volume resuscitation was used in a series of studies to evaluate if the efficacy of RAD therapy under citrate regional anticoagulation was similar to that under systemic heparin anticoagulation. Thus, the comparison in pre-clinical animal models of sham RAD (non-cell) cartridges and RAD (cell-containing) cartridges was begun to assess whether citrate and low $Ca_i$ levels in the blood circuit negatively affected the efficacy of renal tubule cell therapy observed with systemic heparin treatment.

Unexpectedly, the results showed that citrate anticoagulation using the RAD without renal cells (i.e., a SCID treated with citrate) was effective in ameliorating the lung damage from SIRS and was almost as effective in reducing the cardiovascular dysfunction and time to death from septic shock in this large animal model, as detailed below.

(III) Experiment B—Large Animal Model Comparison of Systems Utilizing or Lacking Renal Epithelial Cells The improved porcine model of septic shock described above was used to assess the multi-organ effects of intervention with a renal assist device (RAD) versus a selective cytopheresis inhibitory device (SCID). In this experiment, both RAD and SCID refer to the device of FIG. 7 in the circuit of FIG. 3, as described above. However, the RAD system contains porcine renal epithelial cells in the ICS 740 of the RAD 755 and receives heparin anticoagulation treatment. The SCID system contains no cells in the ICS 740 of the SCID 755 and receives citrate treatment (with no heparin). The following data were derived from a total of 14 animals. Seven animals were treated with sham controls, which were the RAD without porcine renal epithelial cells in the ICS and received heparin anticoagulation treatment, denoted as "Sham/Heparin" in FIGS. 9-13. Four animals were treated with a RAD that included porcine renal epithelial cells and systemic heparin therapy, denoted as "Cell RAD" in FIGS. 9-13. Three animals were treated with a SCID that included no cells in the ICS and received citrate regional anticoagulation, denoted as "Sham/Citrate" in FIGS. 9-13.

Observations of Cardiovascular Parameters

Figure 9:
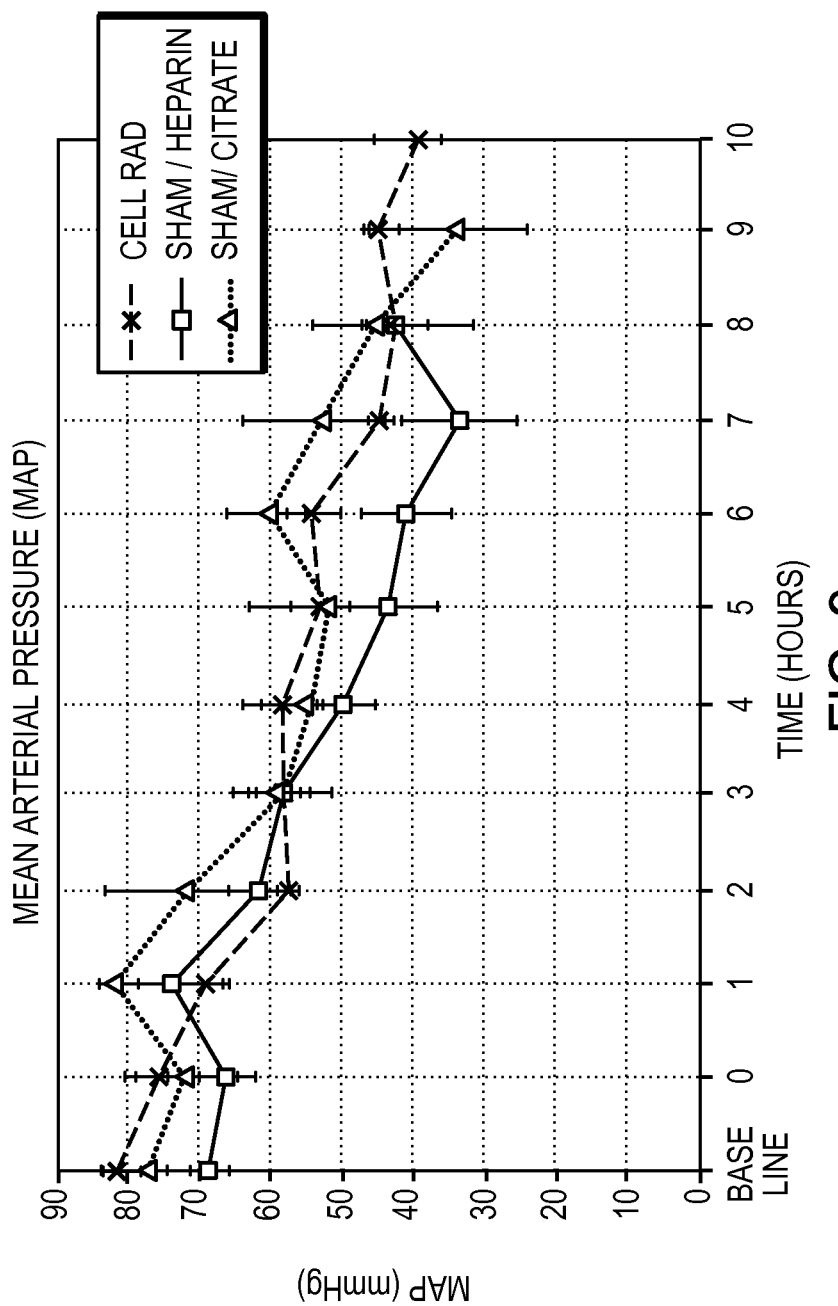
FIG. 9 shows the mean arterial pressure for porcine model groups treated with a system of the present invention, as described in Example 1.
Figure 10:
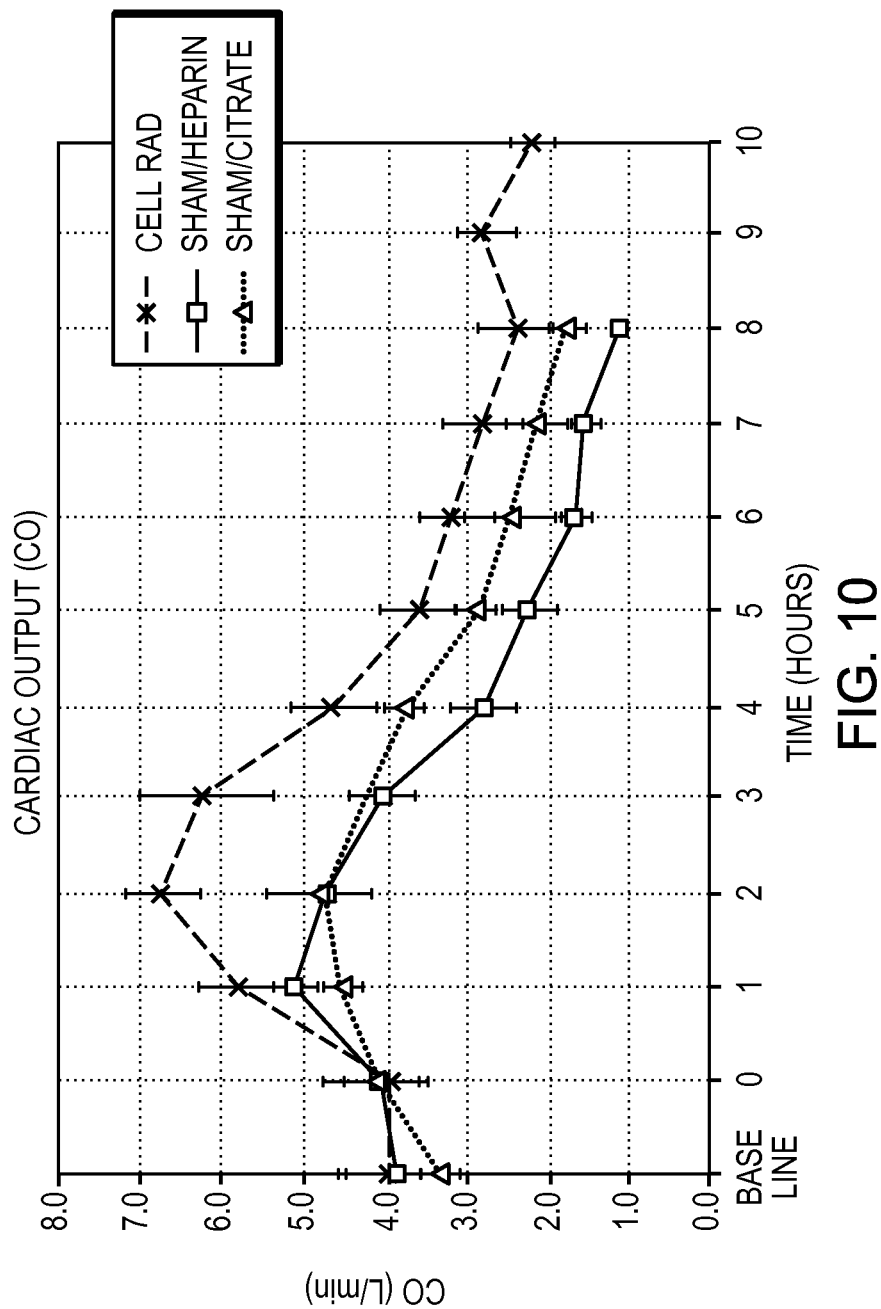
FIG. 10 shows the cardiac output in porcine model groups treated with a system of the present invention, as described in Example 1.

As demonstrated in FIG. 9, the administration of bacteria described above into the peritoneal cavity induced a rapid, profound, and eventually fatal decline in mean arterial pressure (MAP) in all groups. The early data suggested that the SCID with citrate attenuated the effect on MAP compared to sham/heparin control. The cardiac outputs (CO) are detailed for each group in FIG. 10. The CO was substantially higher in the RAD group compared to the other groups. The citrate effect reached significance with more animals, although it was less pronounced than the RAD effect compared to the sham/heparin controls. A similar trend among the groups was observed in stroke volume as well.

Figure 11:
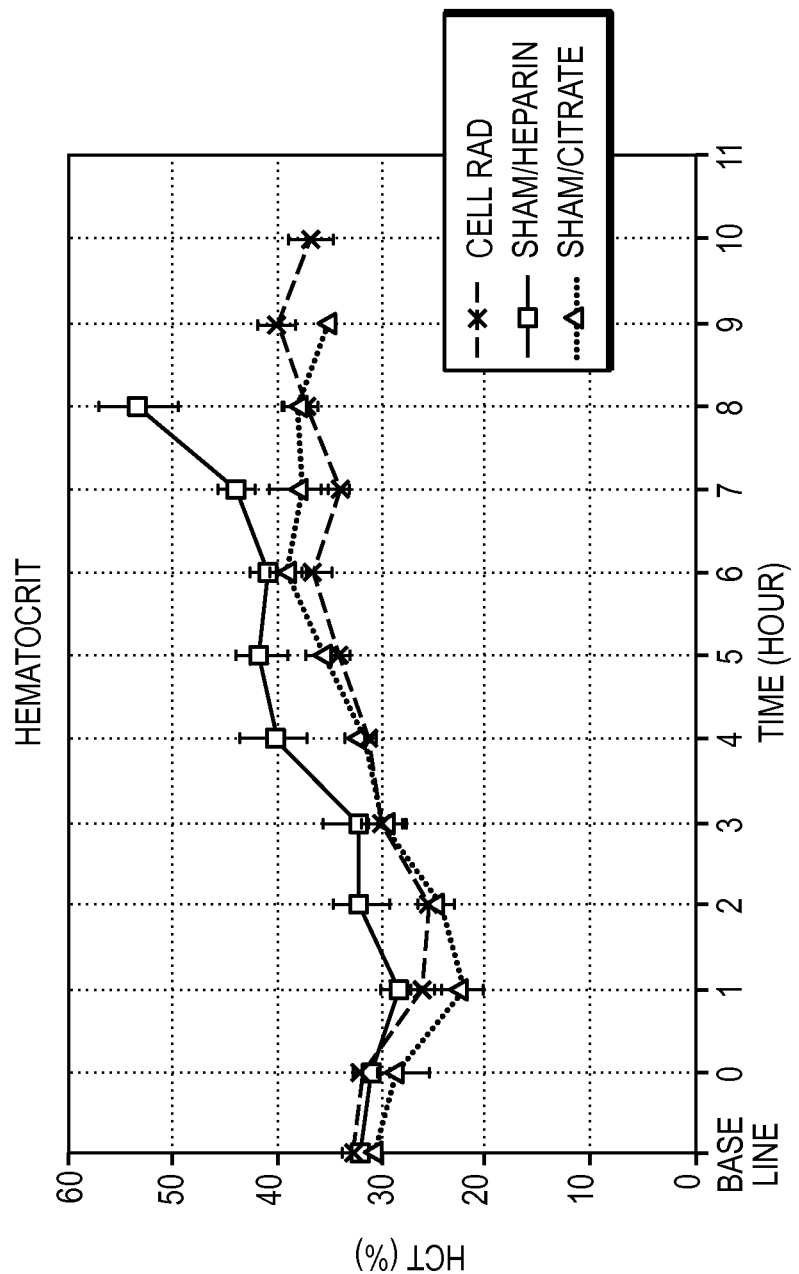
FIG. 11 shows hematocrit levels in porcine model groups treated with a system of the present invention, as described in Example 1.
Figure 12:
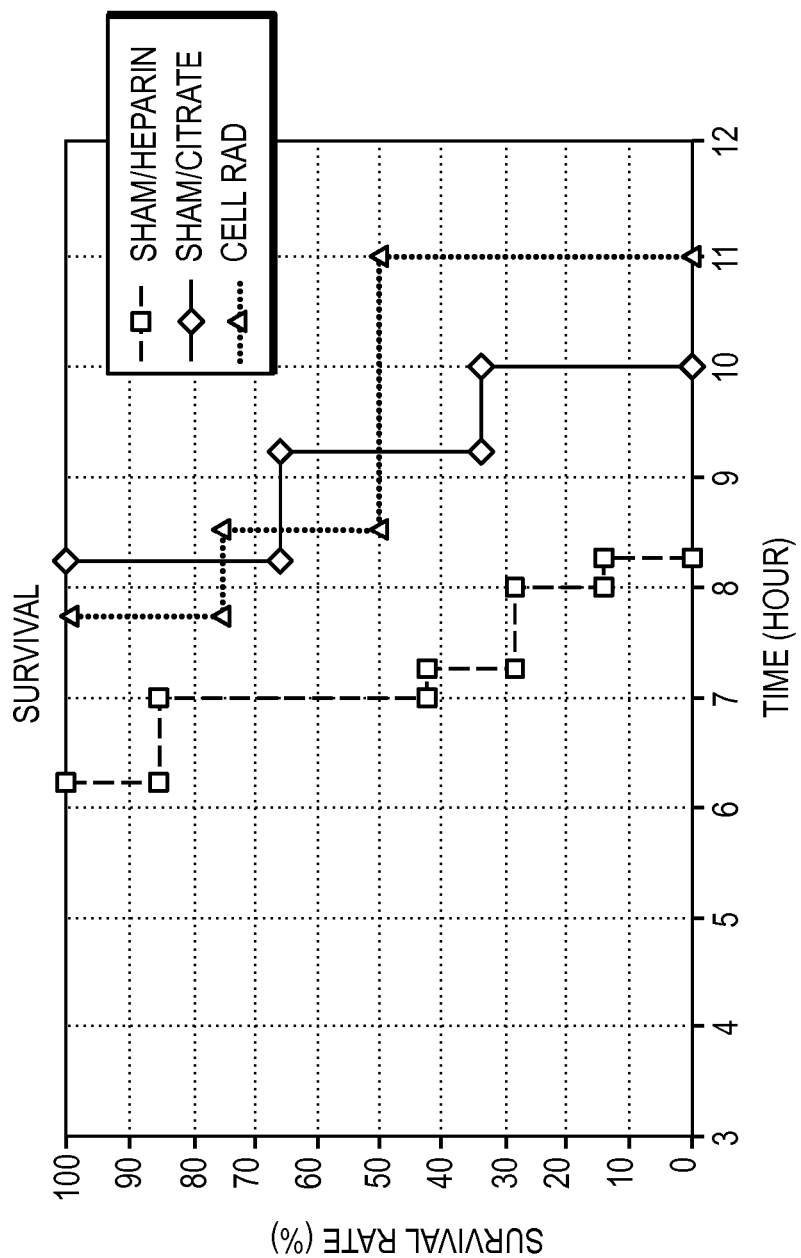
FIG. 12 shows survival curves of porcine model groups treated with a system of the present invention, as described in Example 1.

As an approximate measure of systemic capillary leak induced with this septic course, the changes in hematocrit are shown in FIG. 11. In FIG. 11, the sham/heparin controls had a higher rate of increase with time, reflective of larger rates of volume loss from the intravascular compartment in the sham control group compared to both the RAD and SCID groups. These changes were associated with a substantial survival advantage in the RAD and SCID groups at this preliminary evaluation stage compared to sham/heparin group (see, FIG. 12). The average survival times were 7.25±0.26 hours for the sham/heparin group, 9.17±0.51 hours for the SCID (sham/ citrate) group, and 9.56±0.84 hours for the RAD (with cells in the ICS space) group. These data indicated that the RAD (with cells in the ICS space), and unexpectedly, the SCID, both improve cardiac output, renal blood flow and survival times compared to the sham/heparin control.

Observations of Inflammatory Parameters

To investigate the effect of various therapeutic interventions with the porcine SIRS model, bronchoalveolar lavage (BAL) fluid was obtained at the time of death and evaluated for protein content as a parameter of microvascular damage, various inflammatory cytokines and the absolute number of polymorphonuclear cells (PMNs). As summarized in Table 3, preliminary data indicated that both RAD and SCID treatments resulted in less vascular damage and protein leak and less inflammatory cytokine release in the early phase of pulmonary involvement in SIRS. Levels of IL-6, IL-8 and tumor necrosis factor (TNF)-α were lower in the treatment interventions versus sham controls. Levels of IL-1 and IL-10 were not different. Absolute neutrophil counts in the sham controls were above 1000 cells/mL, and the RAD and SCID groups trended lower, although the n=1 or 2 in each group.

TABLE 3

Protein and Cytokine Levels in Bronchoalveolar Lavage (BAL) Fluid from Pigs with Septic Shock

| | Protein (µg/mL) | TNF-α (pg/mL) | IL-1 (pg/mL) | IL-6 (pg/mL) | IL-8 (pg/mL) |
|---|---|---|---|---|---|
| Sham Control (n = 6) | 143 ± 11 | 21 ± 1 | 18 ± 2 | 63 ± 14 | 126 ± 42 |
| RAD (n = 3) | 78 ± 10 | 18 ± 5 | 18 ± 5 | 32 ± 6 | 33 ± 10 |
| SCD (n = 2) | 110 ± 12 | 13 ± 2 | 14 ± 8 | 33 ± 2 | 84 ± 62 |

Note:
Mean ± SE. BAL performed at time of death.

Observations of Leukocyte Sequestration

The hemodialysis literature suggests that blood circulation through the hollow fibers of a single cartridge results in a transient one-hour neutropenia response (see, e.g., Kaplow et al. (1968) JAMA 203:1135). To test whether blood flow through the extracapillary space of a second cartridge results in higher rates of adherence of circulating leukocytes, total white blood cell (WBC) counts and differentials in the septic animals were measured. The results are shown in FIG. 13.

Figure 13:
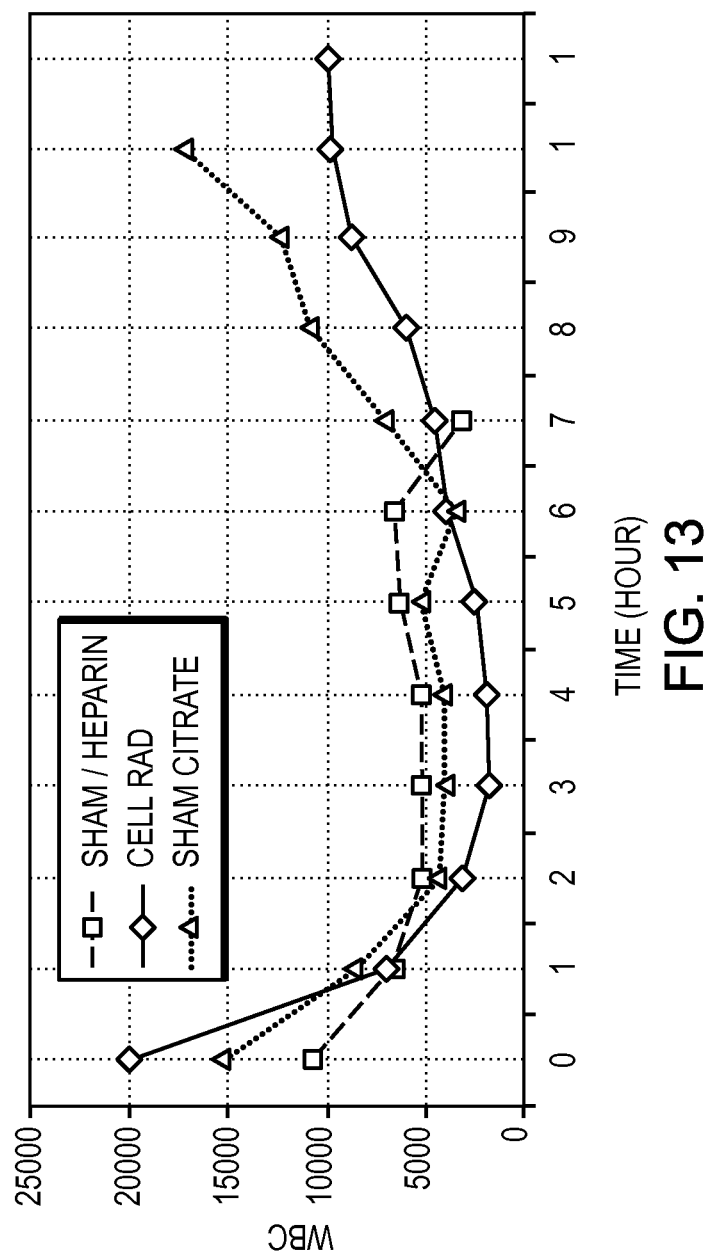
FIG. 13 shows the average total white blood cell counts with time of exposure to a SCID after bacterial challenge in each animal group (n=two to three for each group), as described in Example 1.

As shown in FIG. 13, each group had a leukopenia response to the extracorporeal circuit, with a nadir developing at 2 hours and recovering at 7 hours. The average differential counts from baseline to 3 hours in these animals (n=1-2 in each group, total=5) are detailed in Table 4. All subsets of leukocytes declined, most prominently the neutrophils.

TABLE 4

| | Total WBCs | Neutrophils | Lymphocytes | Monocytes |
|---|---|---|---|---|
| Baseline (hour 0) | 15,696 | 6,422 | 6,792 | 306 |
| Nadir (hour 3) | 2,740 | 684 | 1,856 | 94 |

Note:

TABLE 4-continued

| | Total WBCs | Neutrophils | Lymphocytes | Monocytes |
|---|---|---|---|---|

Values are averages from 5 animals: 1 sham control, 2 RAD-treated, and 2 SCD-treated animals.

To demonstrate the sequestration of leukocytes in the SCID, FIGS. 14A-D depicts the density of leukocyte adherence to the outer surfaces of the hollow fibers. These images demonstrate the sequestration of leukocytes in the SCID. Normal animals undergoing this treatment protocol do not drop their WBC below 9,000 during an 8-hour treatment course, suggesting that primed or activated leukocytes may be necessary to attach to the second membrane system.

These data confirm that the RAD improves cardiac output, renal blood flow (data not shown) and survival times compared to sham/heparin controls. Moreover, it was unexpected to find that the use of citrate in combination with a second, low shear force hollow fiber cartridge (i.e., a SCID) had a large anti-inflammatory effect, even though it contained no cells in the ICS.

Example 2

In Vitro Studies of Leukocyte Sequestration and Inhibition and/or Deactivation

The experiment described in this example shows that leukocytes adhered to a dialysis membrane are inhibited and/or deactivated in the presence of citrate. In addition, other data have demonstrated that citrate anticoagulation abolishes degranulation of neutrophils (a calcium-dependent event) during hemodialysis of subjects with end stage renal disease (ESRD). To evaluate this process in more detail and expand it to other leukocyte populations and cytokine release, the following in vitro experiments were performed.

Methods and Materials

Leukocytes were isolated from normal healthy individuals using established methods. The leukocytes ($10^6$ cells per well) were placed into 12-well tissue culture plates containing 14×14 mm squares of polysulfone membranes (Fresenius, Walnut Creek, Calif.) and allowed to adhere for 60 minutes at 37° C. in RPMI media. The media was removed, cells washed with PBS, and the removed supernatants were analyzed for cell release. RPMI media with citrate ($Ca_i$=0.25 mmol/L) or without citrate ($Ca_i$=0.89 mmol/L) was used to achieve the $Ca_i$ levels described in Table 5 below. Each calcium condition also had media with or without lipopolysaccharide (LPS, 1 µg/mL) to activate the leukocytes.

The cells were exposed to these conditions for 60 seconds and removed from the media to assess release of lactoferrin (LF) and myeloperoxidase (MPO), proteins in exocytotic vesicles from neutrophils, and cytokines, IL-6 and IL-8, released from leukocytes. These compounds were assayed with commercially available Elisa kits (R & D Systems, Cell Sciences, and EMD BioSciences).

Results and Discussion

The results are set forth in Table 5.

TABLE 5

| | Lactoferrin (ng/mL/$10^6$ cells) | | Myeloperoxidase (ng/mL/$10^6$ cells) | | IL-6 (pg/mL/$10^6$ cells) | | IL-8 (ng/mL/$10^6$ cells) | |
|---|---|---|---|---|---|---|---|---|
| | Baseline | Stimulated | Baseline | Stimulated | Baseline | Stimulated | Baseline | Stimulated |
| Normal Ca$_i$ (0.89 mmol/L) | 205 | 416 | 437 | 886 | 3.9 | 4.4 | 29.9 | 35.0 |
| Citrate Ca$_i$ (0.25 mmol/L) | 221 | 187 | 268 | 270 | 3.3 | 2.9 | 25.8 | 19.4 |

Note:
WBC isolations from two different normal controls; each condition analyzed in duplicate. Baseline was without LPS; stimulated condition was with LPS (1 µg/mL).

The citrate-containing media with low Ca$_i$ had no increases in LF, MPO, IL-6, or IL-8, in contrast to the normal Ca$_i$ media, which had substantial increases in these inflammatory proteins. These results demonstrate that the stimulation of leukocyte populations adhered to a dialysis membrane are inhibited and/or deactivated in the presence of citrate, which lowers the Ca$_i$ level in the culture media. This low Ca$_i$ level results in a change in cytosolic calcium levels to inhibit multiple inflammatory responses in leukocytes (e.g. release of a pro-inflammatory substance) and/or deactivate leukocytes.

Example 3

Treatment of Inflammation Associated with Acute Renal Failure (ARF) in Humans

The experiment described in this example shows the unexpected survival rates in human subjects treated with an embodiment of the present invention, namely, a SCID including hollow fiber tubes is in a system treated with citrate versus those patients treated with a similar device in a system treated with heparin. Specifically, in this experiment, SCID refers to a device of FIG. 7 in the circuit of FIG. 3. No renal cells were included in the ICS of the SCID.

Background

The safety and efficacy of renal cell therapy on ten critically ill patients with ARF and multiorgan failure receiving continuous venovenous hemofiltration (CVVH) previously was investigated in Phase I/II trials (see, e.g., Humes et al. (2004) Kidney Int. 66(4):1578-1588). The predicted hospital mortality rates for these patients averaged greater than 85%. The devices used in the previously reported trial were seeded with human renal proximal tubule cells isolated from kidneys donated for cadaveric transplantation but found to be unsuitable for transplantation due to anatomic or fibrotic defects. The results of this clinical trial demonstrated that the experimental treatment could be delivered safely under study protocol guidelines for up to 24 hours when used in conjunction with CVVH. The clinical data indicated that the this system exhibited and maintained viability, durability, and functionality in the clinical setting. Cardiovascular stability of the patients was maintained, and increased native kidney function, as determined by elevated urine outputs, temporally correlated with the treatment.

The system in the previous clinical investigation also demonstrated differentiated metabolic and endocrinologic activity. All but one treated patient with more than a 3-day follow-up showed improvement, as assessed by acute physiologic scores. Six of the 10 treated patients survived past 28 days with kidney function recovery, although mortality rates predicted for these 10 patients using the APACHE 3 scoring system were on average 85 percent. Plasma cytokine levels suggested that this cell therapy produced dynamic and individualized responses in patients depending on their unique pathophysiologic conditions.

The favorable Phase I/II trial results led to subsequent FDA-approved, randomized, controlled, Phase II investigations at 12-15 clinical sites to determine whether this cell therapy approach alters patient mortality. One Phase II study involved 58 patients, of whom 40 were randomized to RAD therapy and 18 made up a control group with comparable demographics and severity of illness by sequential organ failure assessment (SOFA) scores. The early results were as compelling as the Phase I/II results. Renal cell therapy improved the 28-day mortality rate from 61% in the conventional hemofiltration-treated control group to 34% in the cell-treated group (see, e.g., Tumlin et al. (2005) J. Am. Soc. Nephrol. 16:46A). This survival impact continued through the 90- and 180-day follow-up periods (p<0.04), with the Cox proportional hazard ratio indicating that the risk of death was 50% of that observed in the conventional CRRT group. This survival advantage with renal cell therapy was observed for various etiologies of ARF and regardless of organ failure number (1 to 5+) or the presence of sepsis.

Method

An additional study was undertaken to evaluate a commercial cell manufacturing process and the addition of citrate regional anticoagulation. The results of these patient treatment groups were analyzed to compare the mortality rates in patients treated with a SCID (no cells in the ICS) with systemic heparin anticoagulation or citrate regional anticoagulation. The device used in these experiments is schematically shown in FIG. 7 in the circuit depicted in FIG. 3 as described above. However, for this experiment, the second blood line pump is between the SCID and the subject (not between the devices as shown in FIG. 3).

Results

Table 6 shows that the SCID/citrate system yielded marked increases in survival rate at 28 days and between 90 to 180 days.

TABLE 6

| | Survival | | | | | | | |
|---|---|---|---|---|---|---|---|---|
| | (N) | 28 d | (N) | 90-180 d | SOFA | OF | MOF | Sepsis |
| SCID/citrate | 9/12 | 75% | 8/12 | 67% | 11.9 | 3.8 | 2.6 | 58% |
| SCID/heparin | 6/12 | 50% | 3/12 | 25% | 12.3 | 4.1 | 2.65 | 58% |

Note:
SOFA = sequential organ failure assessment;
OF = organ failure number;
MOF = multiple organ failure number.

Figure 15:
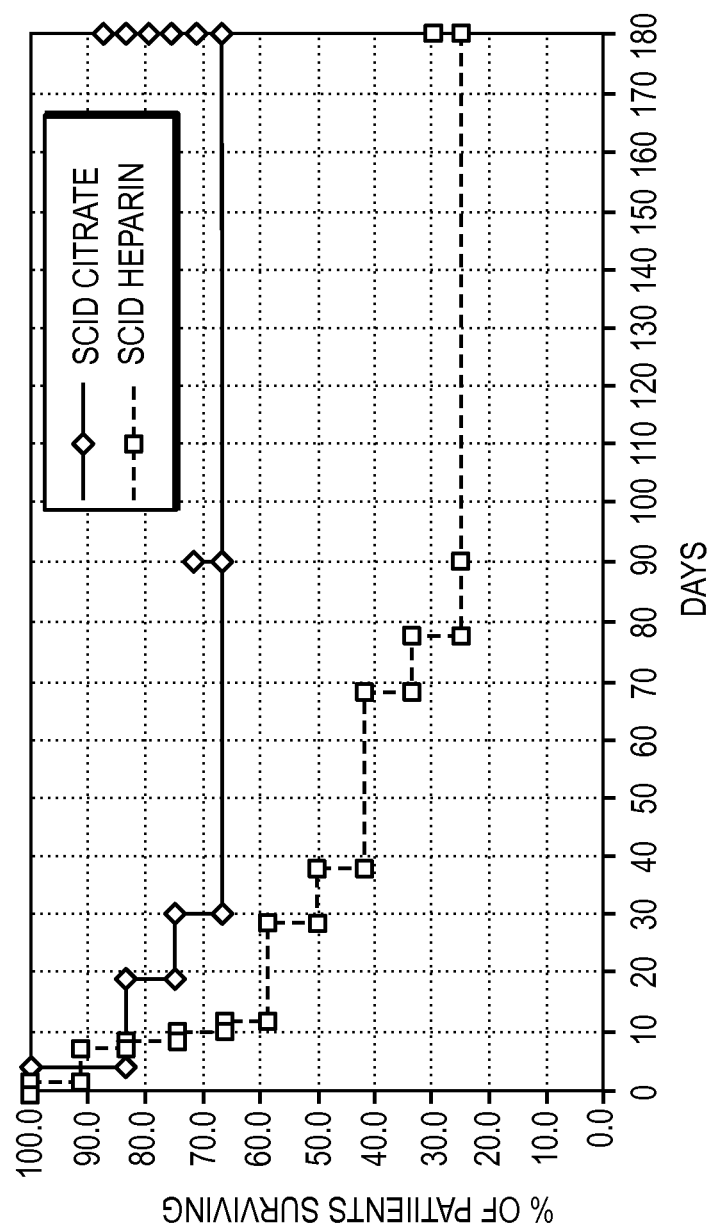
FIG. 15 is a graph showing the difference in survival rate in subjects treated with a SCID and either citrate or heparin treatment.

FIG. 15 graphically shows the marked increase in survival rate between 0 and 180 days in patients treated with devices utilizing citrate ("SCID/citrate") instead of heparin ("SCID/heparin"). These survival differences occurred even though the patient groups had similar activity of disease as measured by SOFA scores and organ failure number. Neither group had cells in the ICS of the second cartridge of the system.

Discussion

This clinical impact was unexpected. These results provided unprecedented and surprising success in maximizing patient survival. Although these clinical data were derived from patients with ARF, it is contemplated that the observation will apply more generally, for example, to SIRS, ESRD and other inflammatory conditions. Further evaluation into potential mechanisms was accomplished with the histological assessment of non-cell cartridges in the citrate- and heparin-treated groups. Similar to data from the animal models described above, the citrate/SCID system had the external surfaces of the hollow fibers of the second cartridge covered with white blood cells on the blood side of this cartridge. Similar binding was seen in the heparin/SCID system.

Example 4

Treatment of Inflammation with a One-Device System

In some instances, it may be beneficial to use a treatment system using a single treatment device (i.e. a SCID without other treatment devices). As discussed previously, certain embodiments of the invention utilize a first treatment device (e.g., a hemofilter) in an extracorporeal circuit that may activate leukocytes (in an unwanted fashion) in addition to performing its primary treatment function. The second treatment device in the series, the SCID, achieves adherence and systemic sequestration in the low-resistance compartment of the ECS (e.g., as shown in FIGS. 2C and 2D). Thus, if the first treatment device is not needed to perform its primary function, it may be beneficial to remove it and reduce unwanted activation of leukocytes. In other embodiments, such as sepsis, the circulating leukocytes may already be activated, and a single-device SCID system (e.g., as shown in FIGS. 2A and 2B) with the blood flow through the low-resistance compartment of the ECS may be adequate for adherence and sequestration of leukocytes. Only a single pump on the bloodline is needed with this circuit, simplifying the therapeutic intervention.

This experiment evaluates the effectiveness of selective cytopheresis, as well as survival rate and the effect of diminishing and/or preventing an inflammatory response, in a subject (e.g., an animal or human patient having an inflammatory response or at risk for developing an inflammatory response). Specifically, this experiment compares a one-device system having only a SCID in the system with a two-device system having a SCID as well as other system components that treat blood, for example, one or more hemofiltration cartridges in the system. The one-device system can be particularly useful for subjects having or at risk of having conditions such as SIRS, in which leukocyte sequestration and, optionally, leukocyte deactivation and/or inhibition of release of a proinflammatory substance from a leukocyte, is a primary treatment objective for the extracorporeal circuit. A two-device (or multiple-device) system can be useful for subjects in need of more than one treatment using an extracorporeal circuit, for example, for a subject with acute renal failure who needs both kidney dialysis treatment and leukocyte sequestration and, optionally, leukocyte deactivation and/or inhibition of release of a proinflammatory substance from a leukocyte.

A first test system will include a single SCID as shown in one of FIG. 5 or 6 in the circuit of either FIG. 2A or 2B, respectively. A second test system will include a SCID as shown in one of FIG. 5 or 6 in the multi-device circuit of either FIG. 2C or 2D, respectively. For both test systems, the SCID hollow fiber cartridge or the entire system will contain citrate. For both systems, ultrafiltrate and cells will not be included in the ICS of the SCID.

Two groups of subjects (e.g., pigs) will be administered bacteria to induce sepsis and SIRS as described in Example 1 above. Each group will then be treated with one of the test systems and measurements such as those described in Example 1 will be taken. The measurements of the two groups will be compared. In addition to the one-device and two-device system configurations described, other configurations of the devices and systems containing those devices may also be tested.

It is anticipated that the magnitude of transient leukopenia and neutropenia will be comparable between the one-device and two-device systems. The relationship of WBC counts and influence on cardiovascular and pulmonary functional parameters, systemic and pulmonary inflammatory indicators, and change in leukocyte activation markers across the single- versus two-device systems will confirm whether the simpler single-device system or the two-device system is beneficial in situations not requiring a second treatment device, although it is anticipated that both single-device and two-device configurations will be effective.

Example 5

Comparison of Leukocyte Sequestration Surface Areas

This experiment evaluates the effectiveness of one or more SCID hollow fiber cartridges having different leukocyte sequestration surface areas in performing selective cytopheresis, to prevent an inflammatory response, and to enhance survival rates in test subjects. Several membrane sizes will be tested. Initial tests will include a comparison of SCID membranes with surface areas of about $0.7\ m^2$ and about $2.0\ m^2$, respectively. Additional test groups can include comparisons of membrane surface areas between about $0.7\ m^2$ and about $2.0\ m^2$ and/or membrane surface areas greater than about $2.0\ m^2$.

In one study, SCIDs having hollow fiber cartridges with various leukocyte sequestration surface areas, as described above, will be prepared. SCIDs of the general design of FIG. 5 will be placed in the circuits of FIG. 2A or 2C, or SCIDs of the general design of FIG. 6 will be placed in the circuits of FIG. 2B or 2D. Subjects (e.g., pigs) will be administered bacteria to induce sepsis and SIRS as described in Example 1 above. Groups of the subjects will then be treated with one or more of the systems described herein. For each system tested, at least two different SCID membrane surface area sized (e.g., $0.7\ m^2$ and $2.0\ m^2$) will be tested. Measurements such as those described in Example 1 will be taken, and the measurements from each of the groups will be compared.

In another study, subjects (e.g. pigs or calves) undergoing CPB will be studied. Treatment with CPB can cause organ dysfunction, including acute kidney injury (AKI) and acute lung injury (ALI). SCIDs having hollow fiber cartridges with various leukocyte sequestration surface areas, will be tested in a CPB circuit.

CPB will be performed on subjects as described in Examples 8 and 9 herein with SCIDs configured in circuits as shown in any of FIGS. 4A-4F. For each system, at least two different SCID membrane surface area sizes (e.g., 0.7 m$^2$ and 2.0 m$^2$) will be tested. Endpoint measurements will include those described herein, for example, in Example 1 or 8. In addition, the severity of CPB-induced AKI and CPB-induced ALI can be assessed as a function of SCID membrane sequestration surface area.

It is anticipated that increased membrane surface area will increase leukocyte binding and cause a longer time interval of the leukopenia induced with the SCID. Accordingly, it is anticipated that SCIDs with larger sequestration surface areas (relative to smaller sequestration surface areas) will improve the effectiveness of selective cytopheresis (e.g., as measured by improved survival rate and/or improved effect of diminishing and/or preventing an inflammatory response) and will have greater beneficial effects on alleviating complications associated with CPB, such as organ injury associated with CPB (e.g., AKI and ALI).

Example 6

A Selective Cytopheresis Device in a Septic Shock Model with Acute Kidney Injury The experiments described in this Example describe preclinical testing of one-pump and two-pump systems with a SCID and either citrate or heparin administration in a porcine model of septic shock with AKI. The experiments generally were directed to two assessments. First, the experiments assessed the efficacy of utilizing a SCID in a one-pump circuit (e.g., the SCID of FIG. 6 in the circuit of FIG. 2D) versus a SCID in a two-pump circuit (e.g., the SCID of FIG. 7 in the circuit of FIG. 3). "One-pump" or "two-pump" refers to the number of pumps on the blood line of a circuit as shown, for example, by pump 204 in FIG. 2D (a one-pump system) or by pumps 204 and 300 in FIG. 3 (a two-pump system). An advantage to using a one-pump circuit is that existing dialysis equipment can be utilized without additional training or pump systems to deliver care at the bedside. In addition, the experiments assessed the mechanism of action of the SCID to sequester activated leukocytes and inhibit their activation state using citrate versus heparin.

Materials and Methods

To assess the efficacy of the SCID in a one-pump circuit versus a two-pump circuit, the following two test systems were prepared. First, a one-pump test system included the SCID of FIG. 6 in the circuit of FIG. 2D. Second, a two-pump test system included the SCID of FIG. 7 in the circuit of FIG. 3. Both test systems also included citrate or heparin and did not include cells in the ICS of the SCID.

The experiments in this example utilized the established porcine model of septic shock with associated AKI and multiorgan dysfunction, as described in Example 1. (See, e.g., Humes et al. (2003) Crit. Care Med. 31:2421-2428.) Briefly, two groups of subjects (pigs) were administered bacteria to induce sepsis and SIRS as described in Example 1 above. Each group then was treated with one of the one-pump or two-pump test systems. Each one-pump and two-pump system had two treatment subgroups, treatment with either citrate infusion or heparin infusion. Thus one group of subjects having sepsis and SIRS was treated with the one-pump system and with either citrate or heparin; the other group of subjects having sepsis and SIRS was treated with the two-pump system and with either citrate or heparin.

White blood cells, neutrophils, and platelets were measured to assess the relative efficacy of the one-pump and two-pump systems. In addition, to assess the mechanism of action for the sequestration and inhibition of activated leukocytes by the SCID with citrate versus heparin, several parameters were measured in systems that used either citrate or heparin. The assessed parameters included myeloperoxidase (MPO) and CD11b, which are indicators of neutrophil activation. For the measurement of CD11b, blood samples from animals were taken and a fluorescent antibody was added that binds to CD 11b protein expressed on a leukocyte's cell surface. The white blood cells were separated into various subsets with cell sorting, and the neutrophils in the neutrophil gate were then analyzed by fluorescent intensity, which is proportional to the number of CD 11b molecules on the surface that bound the fluorescent antibody. The entire neutrophil population was then analyzed, and the level of activation with CD 11b expression was quantitatively assessed as mean fluorescent intensity (MFI). The assessed parameters also included animal survival.

Results

Figure 16A:
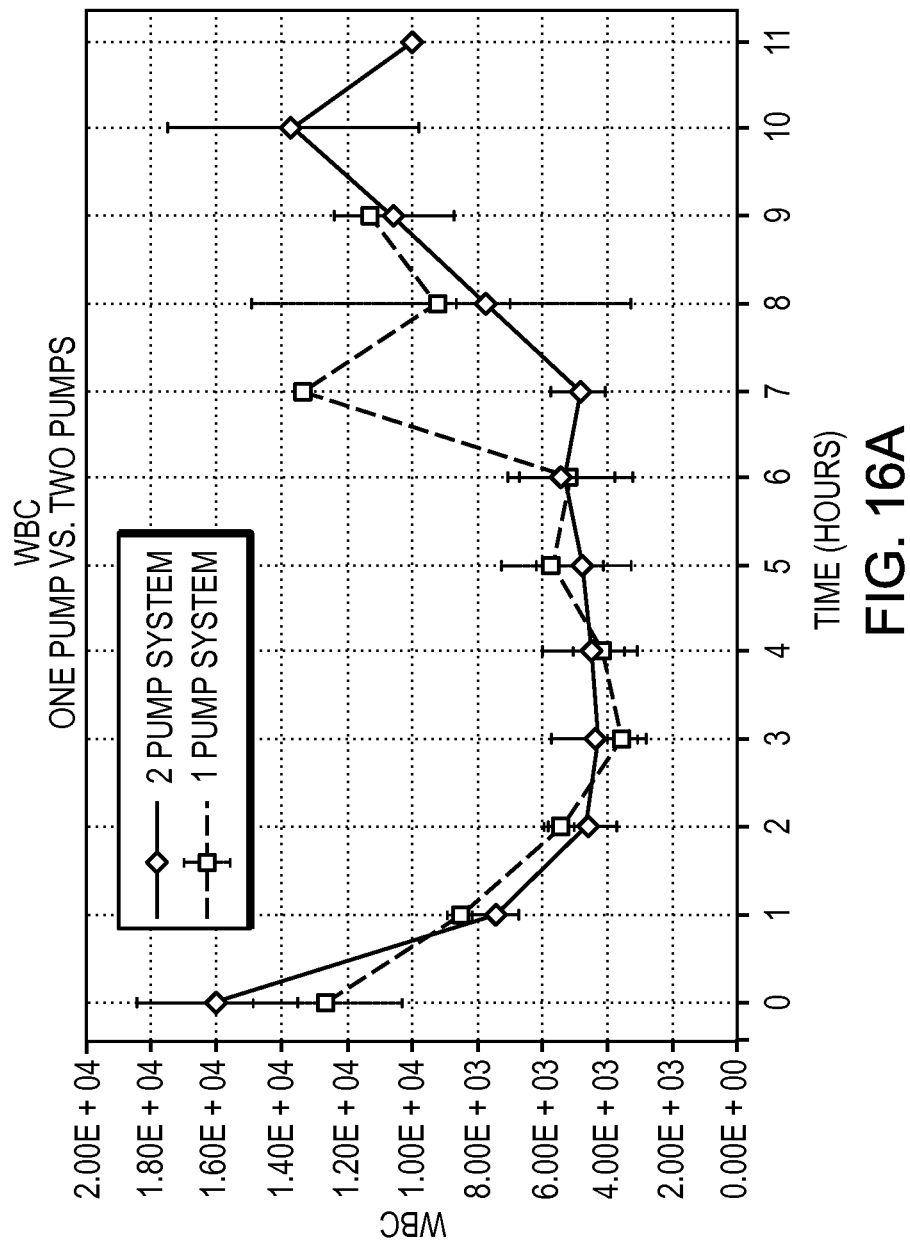
FIGS. 16A and 16B are graphs comparing the number of white blood cells (WBC) and neutrophils, respectively, in one pump and two pump system configurations of the present invention.
Figure 16B:
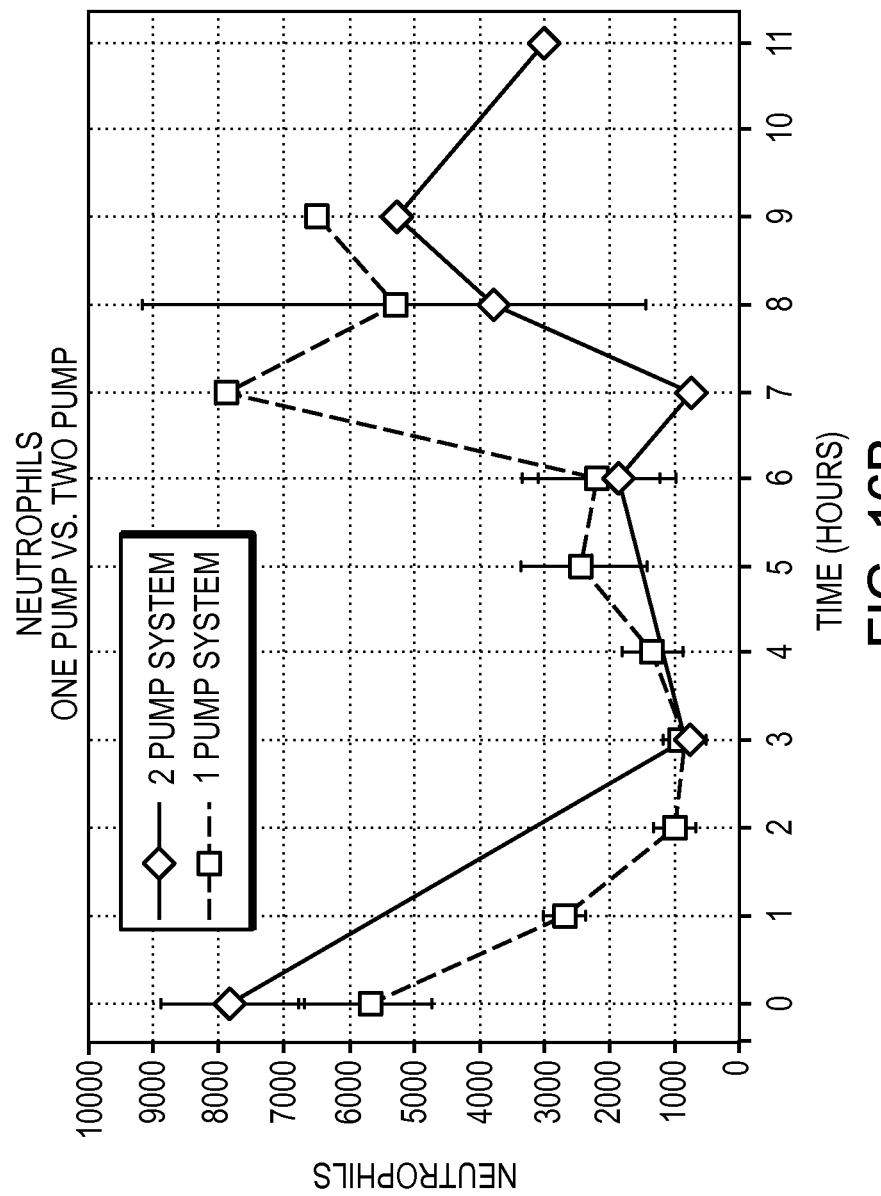
Figure 17:
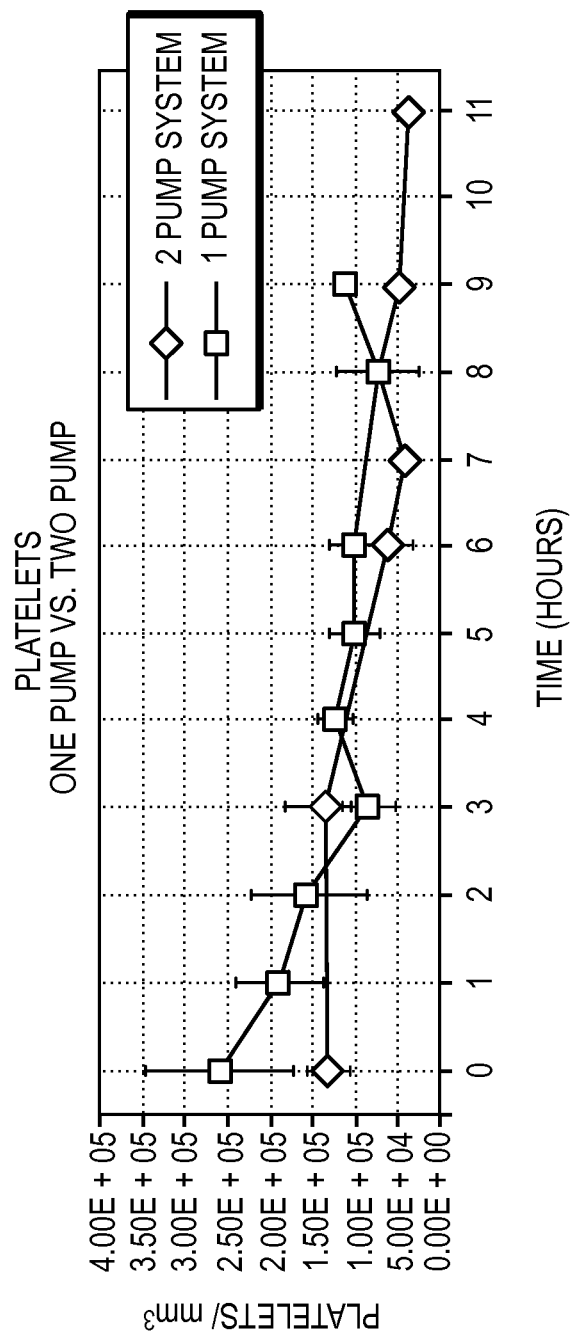
FIG. 17 is a graph showing the amount of platelets in two exemplary embodiments of system configurations of the present invention.

FIGS. 16A, 16B, and 17 show results of the effect of the one-pump and two-pump systems on leukocyte counts, neutrophil counts, and platelet counts. Because leukocyte sequestration (FIG. 16A), neutrophil sequestration (FIG. 16B) and platelet sequestration (FIG. 17) were generally the same for citrate-treated and heparin-treated one-pump systems and for citrate-treated and heparin-treated two-pump systems, these figures display an average of the two one-pump subgroups as compare to an average of the two two-pump subgroups. FIGS. 18-21 show the results of the citrate-treated or heparin-treated systems. Because the measured characteristic for FIGS. 18-21 were generally the same for one-pump and two-pump systems treated citrate and for one-pump and two-pump systems treated with heparin, these figures display an average of the two citrate subgroups as compared to an average of the two heparin subgroups.

Two-pump versus one-pump test system comparison. To assess possible effects that pressure and/or flow differences between the one-pump and two-pump circuits might have on the sequestration of leukocytes in the SCIDs of the two test systems, white blood cell (WBC) and neutrophil counts in the systemic blood were examined. The results for the one-pump and two-pump systems relating to WBC and neutrophil counts are shown in FIG. 16A and FIG. 16B, respectively. As detailed in the Figures, no difference was observed in these parameters between the one-pump system (n=5) and two-pump system (n=5).

Platelet sequestration. The platelet count was also assessed for animals treated with either the one-pump or two-pump systems. As indicated in FIG. 17, both the one-pump and the two-pump systems with the SCID showed decreased platelet counts for at least 9 hours following treatment with the SCID. These data indicate that systems having a SCID sequester platelets.

Figure 18:
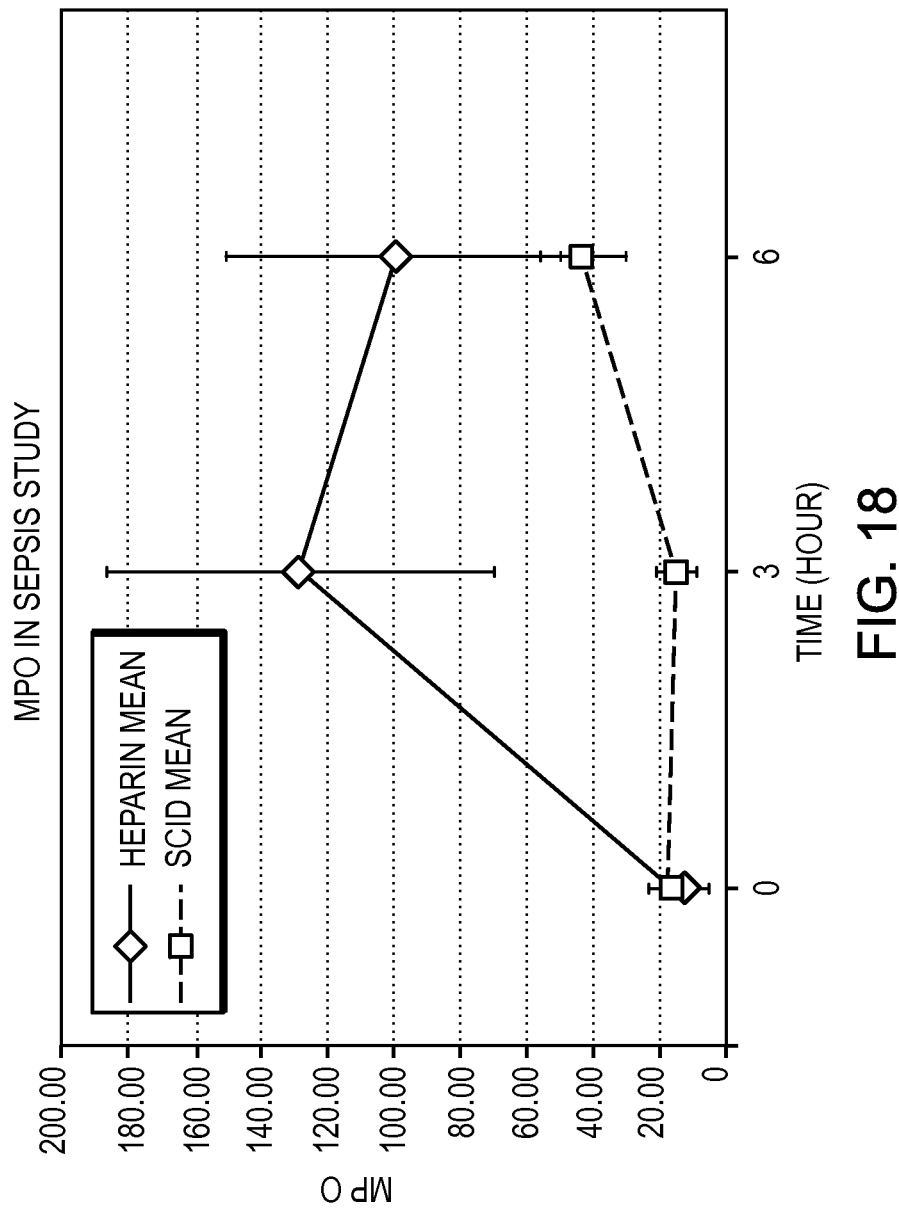
FIG. 18 is a graph showing the average myeloperoxidase (MPO) levels in animals treated with either a SCID and citrate or a SCID and heparin.
Figure 19:
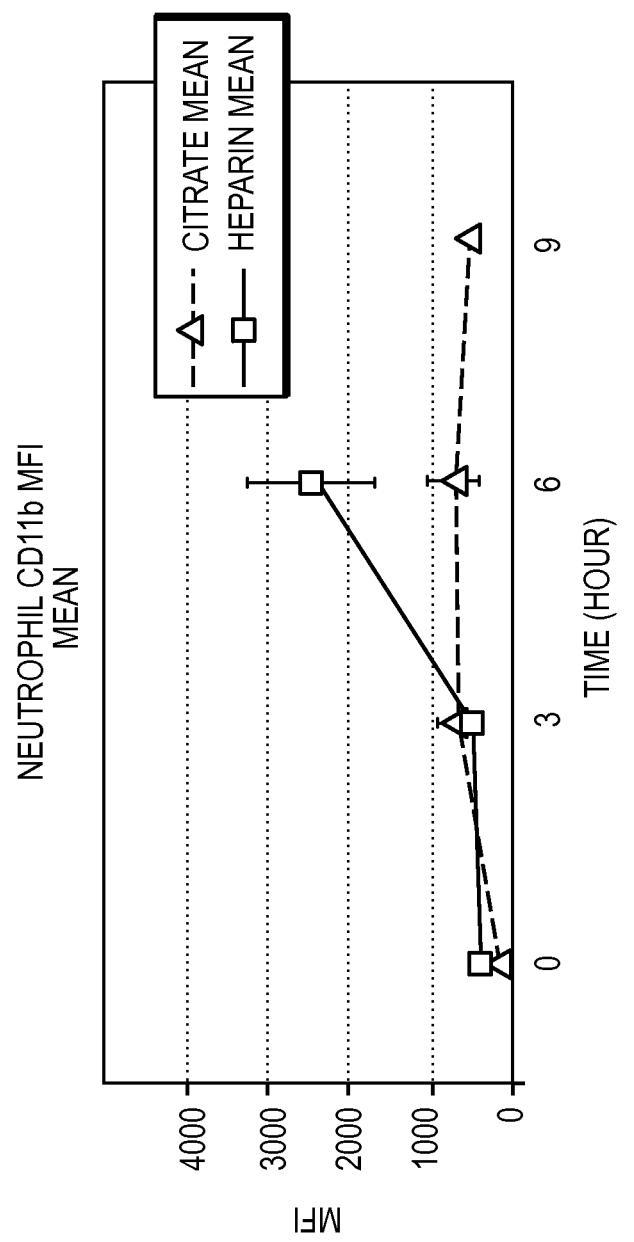
FIG. 19 is a graph showing the expression of CD11b, a neutrophil membrane protein responsible for neutrophil binding to endothelium, in animals treated with either a SCID and citrate or a SCID and heparin.

Neutrophil activation. Activated neutrophils release various enzymes in response to invading microbes or tissue injury to initiate tissue repair. The dominant enzyme released from neutrophil granules is myeloperoxidase (MPO). Accordingly, systemic levels of MPO were measured to indicate the level of neutrophil activation in subjects. FIG. 18 shows that the average MPO levels in animals treated with the SCID and citrate (SCID Mean; n=5) was lower than in animals treated with SCID and heparin (Heparin Mean; n=3). The level of neutrophil activation also was quantitated by measuring the expression of CD11b, a membrane protein responsible for binding onto the endothelium as a first step to exiting the circulation to a site of inflammation. As detailed in FIG. 19, at hour 6 of sepsis induction, the MFI of neutrophils in the systemic circulation was dramatically increased in the animals treated with the SCID and heparin (Heparin (Systemic); n=4) compared to the animals treated with the SCID and citrate (Citrate (Systemic); n=4).

Figure 20:
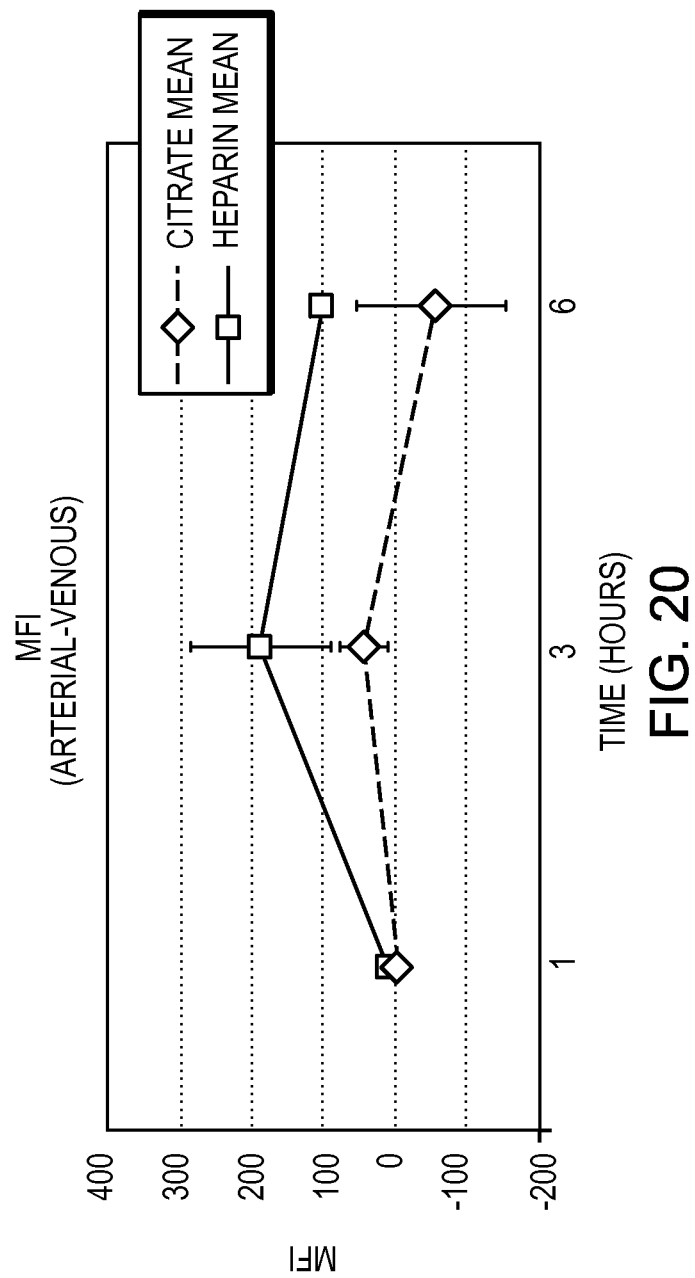
FIG. 20 is a graph showing the number of neutrophils in the arterial and venous lines of systems according to the present invention, in animals treated with either a SCID and citrate or a SCID and heparin.

The analysis was further refined by assessing neutrophil MFI in the arterial and venous lines of the circuits to obtain an average across the whole circuit. Samples were taken simultaneously from the arterial line of the circuit where blood exits the subject into the bloodline and from the venous line of the circuit where blood exits the bloodline and re-enters the subject. The difference in MFI (arterial–venous) in the heparin group (n=4) and citrate group (n=4) was dramatically different at 3 and 6 hours, as shown in FIG. 20. This data suggests that citrate infusion suppresses the level of neutrophil activation along the circuit, which can be indicative of less activated circulating neutrophils systemically for the same time periods.

Figure 21:
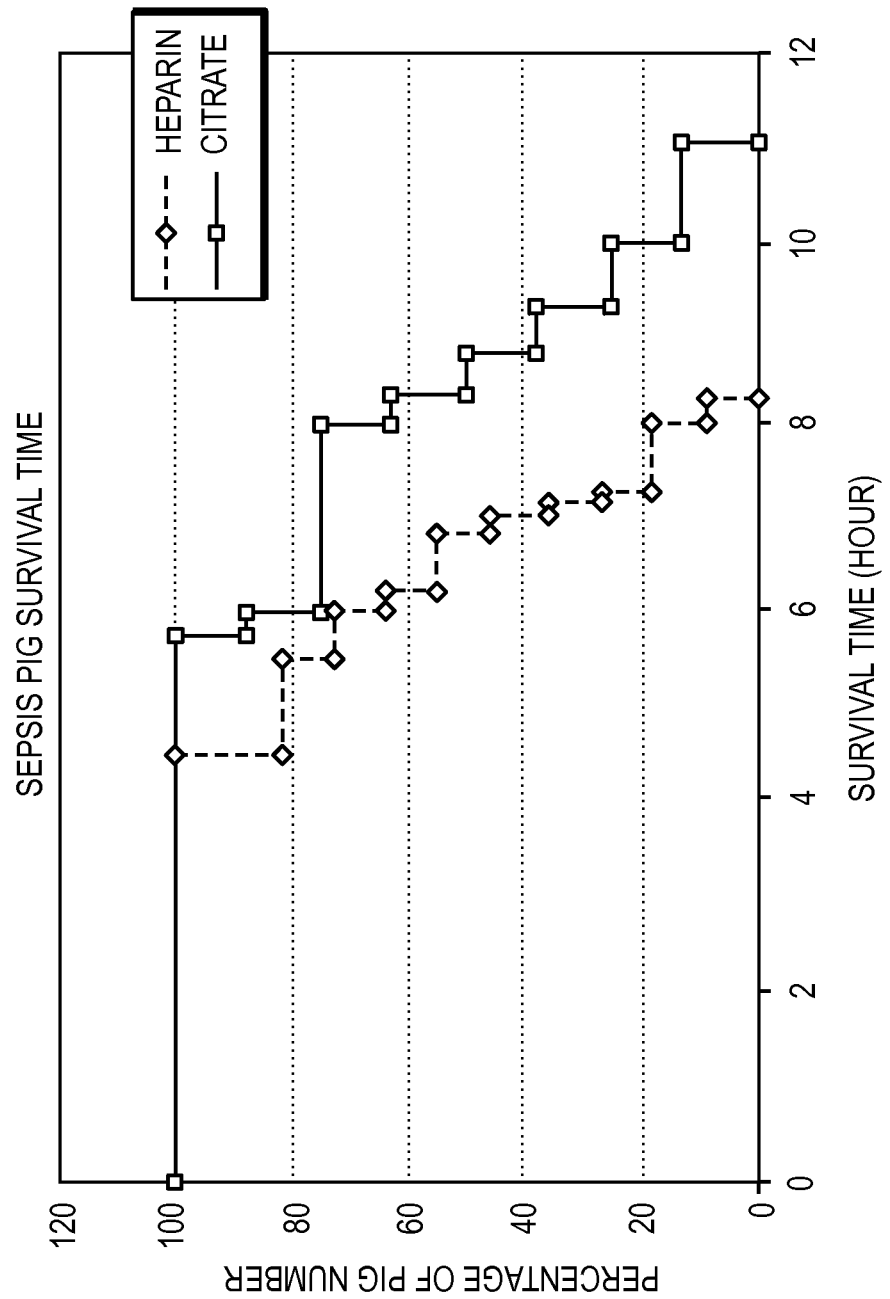
FIG. 21 is a graph showing the percentage of septic animals surviving as a function of time in animals treated with either a SCID and citrate or a SCID and heparin.

Animal survival. The ultimate assessment of the efficacy of the SCID with citrate as compared to the SCID with heparin is the survival effect. As shown in FIG. 21, a consistent survival time advantage was observed in the citrate group, as compared to the heparin group. The mean survival time for animals treated with the SCID with citrate was 8.38+/−0.64 hours (n=8), whereas the mean survival time for animals treated with the SCID with heparin was 6.48+/−0.38 hours (n=11).

Additional assessments are contemplated. For example, data sets to evaluate the effect of the SCID with systemic heparinization versus regional citrate anticoagulation, or the effect of a one-pump or two-pump system can include: 1. cardiovascular parameters (heart rate; systolic, diastolic, and MAP; cardiac output; systemic vascular resistance, stroke volume; renal artery blood flow; central venous pressure; pulmonary capillary wedge pressure); 2. pulmonary parameters (pulmonary artery systolic and diastolic pressures, pulmonary, vascular resistance, arterial to alveolar $O_2$ gradient); 3. arterial blood gases ($pO_2$, $pCO_2$, pH, total $CO_2$); 4. complete blood counts (hematocrit (indirect measurement of capillary leak); WBC and Differential); 5. inflammatory indices (systemic serum levels of cytokines (IL-6, IL-8, IL-1, INF-$\gamma$, TNF-$\alpha$)); and 6. pulmonary inflammation by BAL fluid parameters (protein content (vascular leak); total cell counts with differential; TNF-$\alpha$, IL-6, IL-8, IL-1, INF-$\gamma$, neutrophil myeloperoxidase and elastase; alveolar macrophages from BAL fluid and baseline and stimulated levels of cytokines assessed after LPS challenge). In addition, SCID inflammatory parameters (serum levels from pre-hemofilter, pre-second cartridge and post-second cartridge of various cytokines (IL-6, IL-8, TNF-$\alpha$, IL-1, INF-$\gamma$)) and neutrophil exocytotic compounds (myeloperoxidase, elastase and lactoferrin) can be measured to assess leukocyte activity, and simultaneous measurements of these elements also can be made in the UF pre- and post-second cartridge to correlate with the blood and UF compartments during the progression of treatment. Moreover, oxidative markers in serum and BAL fluid can be measured using gas chromatography and mass spectrometry to assess inflammation-induced oxidative stress in the various groups.

Conclusions

The data from the experiments confirm that an extracorporeal circuit that includes a SCID and citrate treatment can effectively sequester and inhibit the release of a pro-inflammatory substance from, or deactivate, a leukocyte. Specifically, these data show that leukocyte sequestration effects are similar between the one-pump and the two-pump circuits. In addition, the SCID and citrate treatment system diminished the level of neutrophil activation as compared to a SCID and heparin treatment system in a septic shock animal model. The efficacy of the SCID and citrate treatment system resulted in increased survival time in a lethal animal model of sepsis. Moreover, both the one-pump system and the two-pump system effectively sequestered platelets for at least nine hours. Based on this data, it is contemplated that sequestration of platelets and deactivating the platelets and/or inhibiting release of pro-inflammatory substances from the platelets may have beneficial effects similar to those achieved by sequestering leukocytes and deactivating the leukocytes and/or inhibiting release of pro-inflammatory substances from the leukocytes as described throughout the description and examples.

Example 7

Treatment of End Stage Renal Disease in Humans

The experiment described in this example is designed to evaluate survival rates in human subjects treated with an embodiment of the present invention, namely, a cartridge comprising a hollow fiber tube in a system treated with citrate versus a similar system treated with heparin. The system configuration in this experiment will be the SCID of one of FIG. 5 or 6 in the circuit of one of FIG. 2C or 2D, respectively, without cells in the ICS of the SCID. Methods and observations can include a comparison of the citrate versus heparin systems without additional renal cells in the SCID cartridge.

Background

One example of disease associated with a chronic pro-inflammatory state is end stage renal disease (ESRD). (see, e.g., Kimmel et al. (1998) Kidney Int. 54:236-244; Bologa et al. (1998) Am. J. Kidney Dis. 32:107-114; Zimmermann et al. (1999) Kidney Int. 55:648-658). Dialysis, the predominant therapy, is focused on small-molecule waste removal and fluid balance. However, it does not address the chronic inflammation associated with ESRD. In ESRD patients it is associated with severe morbidity and unacceptably high annual mortality rates of up to 21% (see, e.g., USRD System, USRDS 2001 Annual data report: Atlas of end-stage renal disease in the United States, 2001, National Institutes of Health, National Institute of Diabetes and Digestive and Kidney Diseases: Bethesda. p. 561).

The life expectancy for patients with ESRD averages four to five years. Vascular degeneration, cardiovascular disease, poor blood pressure control, frequent infections, chronic fatigue, and bone degeneration impact significantly on the quality of life and generate high morbidity, frequent hospitalizations, and high costs. The dominant cause of mortality in ESRD patients is cardiovascular disease, accounting for nearly 50% of overall mortality in ESRD (see, e.g., USRD System, USRDS 2001 Annual data report: Atlas of end-stage renal disease in the United States, 2001, National Institutes of Health, National Institute of Diabetes and Digestive and Kidney Diseases: Bethesda. p. 561), followed by infectious events.

ESRD patients develop a chronic inflammatory state that predisposes them to both cardiovascular disease as well as acute infectious complications. ESRD patients are more susceptible to infection despite adequate hemodialysis. Chronic hemodialysis induces a change in the pattern of cytokines equivalent to a chronic pro-inflammatory state (see, e.g., Himmelfarb et al. (2002) Kidney Int. 61(2):705-716; Himmelfarb et al. (2000) Kidney Int. 58(6):2571-2578), independent of membrane activation, inflammation, and clearance.

These small proteins can be hemofiltered, but plasma levels are not changed due to increased rates of production (see, e.g., Kimmel et al. (1998) supra; Bologa et al. (1998) supra; Zimmermann et al. (1999) supra; Himmelfarb et al. (2002) supra; Himmelfarb et al. (2000) supra). Enhanced exposure to oxidative stress in ESRD patients undergoing hemodialysis further compromises the immune system and enhances susceptibility to infection (see, e.g., Himmelfarb et al. (2002) supra; Himmelfarb et al. (2000) supra).

Clinically, the chronic inflammatory state in ESRD patients is evident by elevated levels of CRP, an emerging clinical marker, along with elevated levels of pro-inflammatory cytokines, including IL-1, IL-6, and TNF-α (see, e.g., Kimmel et al. (1998) supra; Bologa et al. (1998) supra; Zimmermann et al. (1999) supra). All these parameters are associated with enhanced mortality in ESRD patients. Specifically, IL-6 has been identified as a single predictive factor closely correlated with mortality in hemodialysis patients. Each picogram per milliliter increase of IL-6 increases the relative mortality risk of cardiovascular disease by 4.4% (see, e.g., Bologa et al. (1998) supra). Indeed, growing evidence suggests that the pro-inflammatory state is due to the priming and activation of neutrophils in patients with ESRD (see, e.g., Sela et al. (2005) J. Am. Soc. Nephrol. 16:2431-2438).

Method

Patients with end-stage renal failure will have their blood treated with an extracorporeal circuit comprising a hemofiltration device, a SCID, and citrate or, as a control, a hemofiltration device, a SCID, and heparin (i.e., the SCID of one of FIG. 5 or 6 in the circuit of one of FIG. 2C or 2D, respectively, with citrate or with heparin treatment). The studies may also include within each SCID, renal tubule cells (so that the SCID also acts as a renal assist device or RAD). Blood will flow from the patient to the hemofiltration device, to the SCID, and back to the patient. Appropriate pumps and safety filters may also be included to facilitate flow of the blood back to the patient.

Data sets to evaluate the effect of the SCID with citrate or heparin will include SCID inflammatory parameters (serum levels from pre-hemofilter, pre-second cartridge and post-second cartridge of various cytokines (IL-6, IL-8, TNF-α, IL-1, INF-γ)) and neutrophil exocytotic compounds (myeloperoxidase, elastase and lactoferrin), which are measured to assess leukocyte activity across the various component cartridges within the SCID. If a circuit with a SCID and UF is used (e.g., the SCID of FIG. 7 in the circuit of FIG. 3), simultaneous measurements of these elements will also be made in the UF pre- and post-second cartridge to correlate with the blood and UF compartments during the progression of treatment.

Results and Discussion

It is expected that ESRD patients whose blood is treated with the extracorporeal circuit comprising the SCID and citrate will show significantly better results as compared to ESRD patients treated with the extracorporeal circuit comprising the SCID and heparin. Specifically, it is expected that the pro-inflammatory markers will be lowered in patients receiving SCID with citrate treatment versus those receiving SCID with heparin treatment.

Example 8

A Selective Cytopheresis Device as Part of a Cardiopulmonary Bypass Circuit

The experiments described in this example employed a single hemofilter cartridge as the SCID (e.g., the SCID shown in FIG. 5 or 6), which was connected to an extracorporeal circuit with blood flow (200 mL/minute) in a parallel circuit to a larger volume flow circuit. Citrate regional anticoagulation was used to improve both anticoagulation of this parallel circuit as well as a means to deactivate leukocytes, which were sequestered along the outer surface of the membranes within the SCID.

The protocol included an extracorporeal CPB circuit with a SCID in a calf model. The use of a SCID in each circuit had a temporal correlation to substantive falls in circulating leukocytes, predominantly neutrophils. This decline was sustained throughout the procedures without breakthrough of the sequestration effect. Circuit designs for easy incorporation of the SCID into the existing CPB circuits without safety issues are shown in FIGS. 4B and 4C.

Background

Cardiac surgery advances have been absolutely dependent upon the techniques for CPB. Unfortunately, it has been recognized that a systemic inflammatory response occurs in association with CPB, resulting in multiple organ dysfunctions following surgery. Multiple insults during CPB have been shown to initiate and extend this inflammatory response, including artificial membrane activation of blood components (membrane oxygenator), surgical trauma, ischemia-reperfusion injury to organs, changes in body temperature, blood activation with cardiotomy suction, and release of endotoxin. These insults promote a complex inflammatory response, which includes leukocyte activation, release of cytokines, complement activation, and free-radical generation. This complex inflammatory process often contributes to the development of ALI, AKI, bleeding disorders, altered liver function, neurologic dysfunction, and ultimately multiple organ failure (MOF).

Pulmonary dysfunction is very common after surgery requiring CPB. This acute lung injury can be mild, with postoperative dyspnea to fulminant ARDS. Nearly 20% of patients require mechanical ventilation for more than 48 hours following cardiac surgery requiring CPB. ARDS develops in approximately 1.5-2.0% of CPB patients with a mortality rate exceeding 50%. Renal dysfunction with AKI is also a common occurrence in adult patients after CPB. Up to 40% of these patients develop rises in serum creatinine and BUN and in the 1-5% requiring dialytic support, the post-operative mortality rate approaches 80%.

The mechanisms responsible for multiple organ dysfunction following CPB are numerous, interrelated and complex, but growing evidence suggests a critical role in the activation of circulating blood leukocytes, especially the neutrophil, in the development of ARDS in CPB-induced post-pump syndrome. Increasing evidence supports that the acute lung injury in both ARDS and the post-pump syndrome is predominantly neutrophil mediated following PMN sequestration in the lungs. The sequestered and activated PMNs migrate into lung tissue, resulting in tissue injury and organ dysfunction. Therapeutic interventions described in the art that are directed toward leukocyte depletion during CPB have been evaluated both in pre-clinical animal models and early clinical studies. The results with leukocyte-depleting filters of the art have been inconsistent, with no reduction in circulating leukocyte counts during CPB but mild improvement of oxygen requirements. No significant clinical improvement was seen in patients undergoing elective coronary artery bypass graft (CABG) with a leukocyte-depleting filter of the art. In contrast, the systems, devices, and methods of the present invention will have beneficial effects, as described below. Depletion of leukocytes with a blood separator may improve postoperative lung gas exchange function.

Methods and Results

Surgery was performed on each of three calves, identified as SCID 102, SCID 103, and SCID 107. Each calf (approx. 100 kg) was placed under general anesthesia and connected to a CPB circuit in order to place a ventricular assist device (VAD). CPB was accomplished between 60-90 minutes with cardioplegia and aortic cross-clamping. The SCID was placed at the site depicted in either FIG. 4B or FIG. 4C, as identified below for each animal. Results of the three animals (SCID 102, SCID 103, and SCID 107) are summarized in FIGS. 22A-22F and 23A-23B.

Figure 22A:
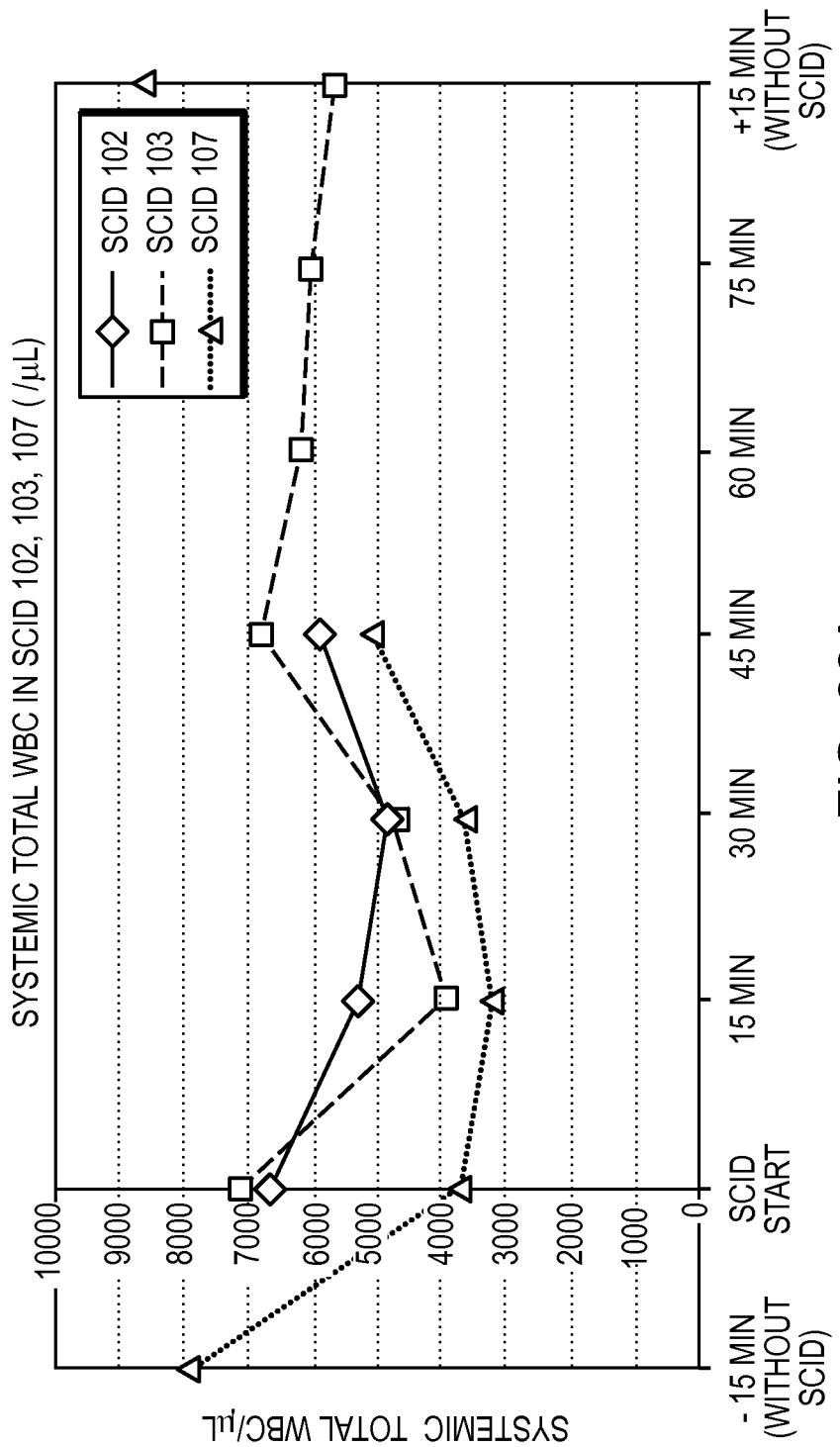
FIGS. 22A-22F are graphs showing the concentration of systemic total white blood cells (WBC), systemic neutrophils, systemic lymphocytes, systemic monocytes, systemic eosinophils, and systemic platelets, respectively, in animals subjected to cardiopulmonary bypass surgery and treated with a system of the present invention that included a SCID and citrate.
Figure 22B:
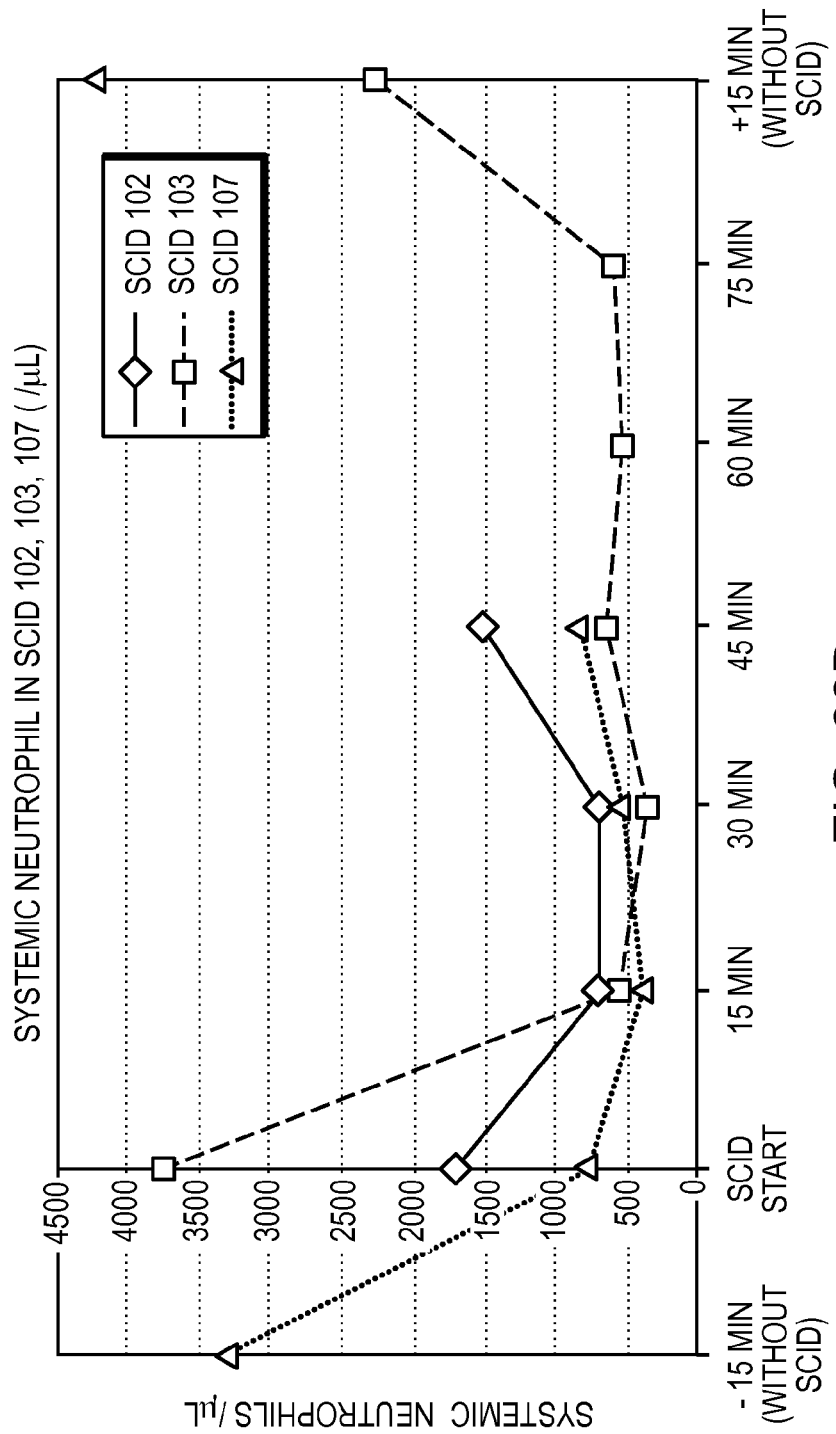
Figure 22C:
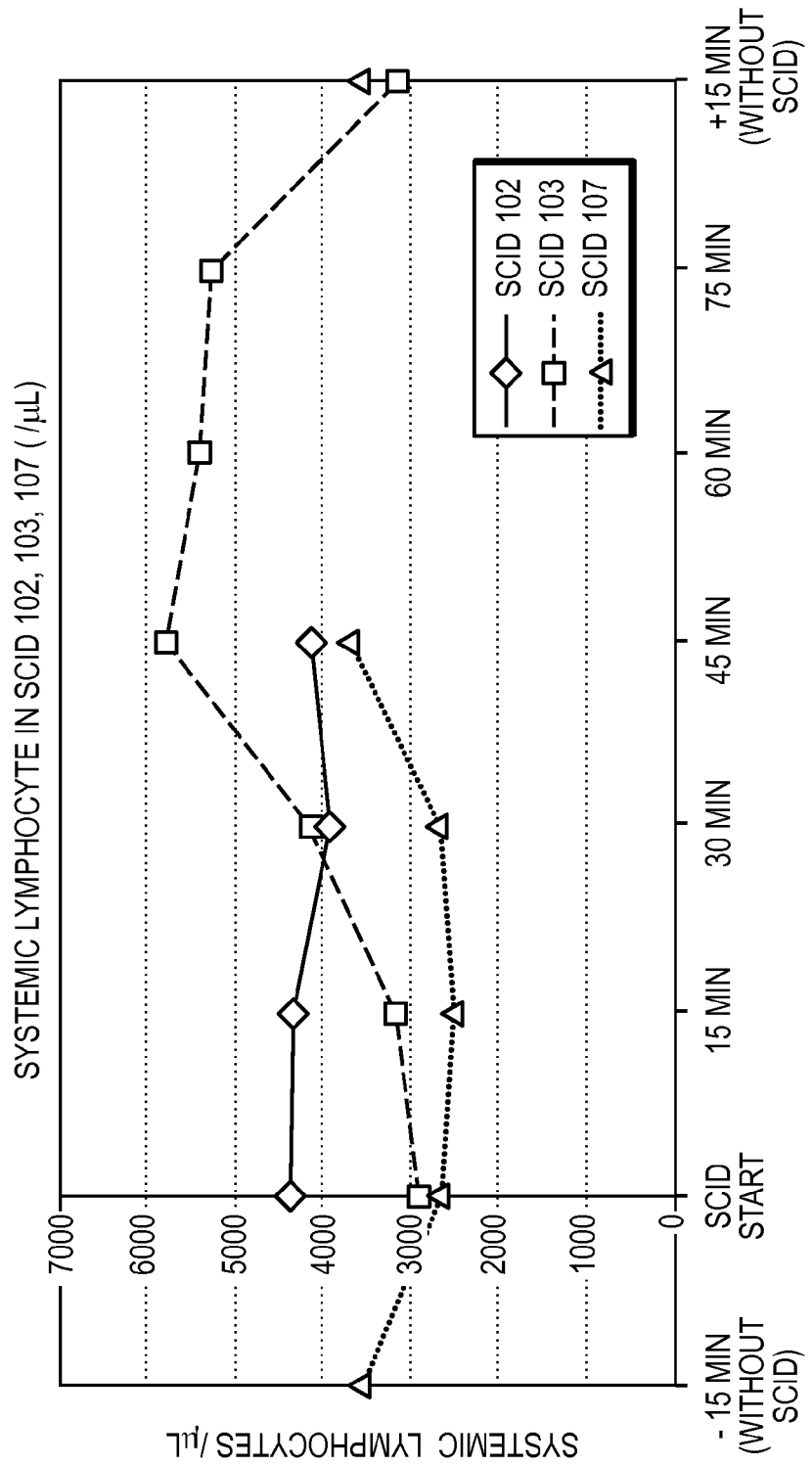
Figure 22D:
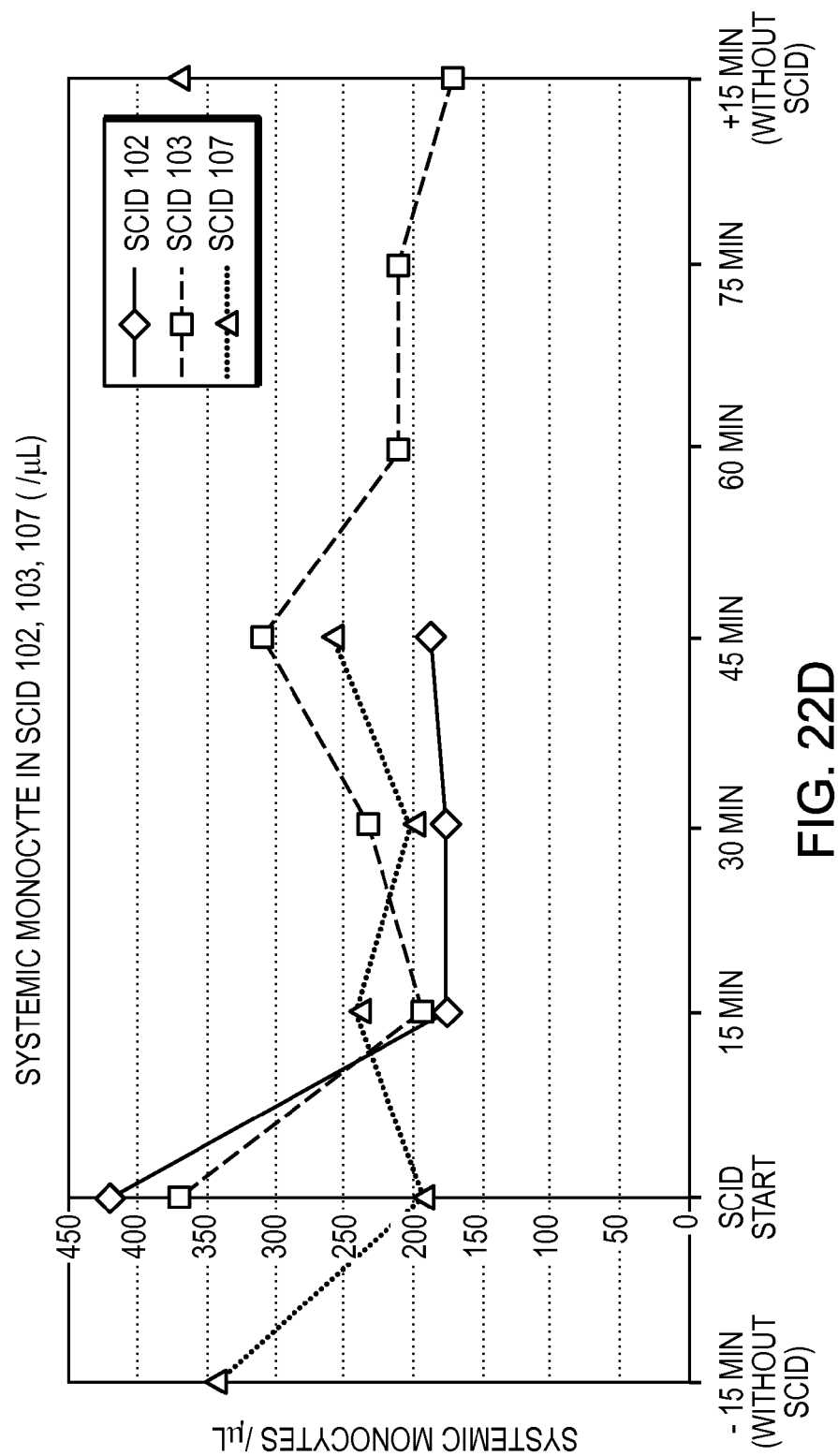
Figure 22E:
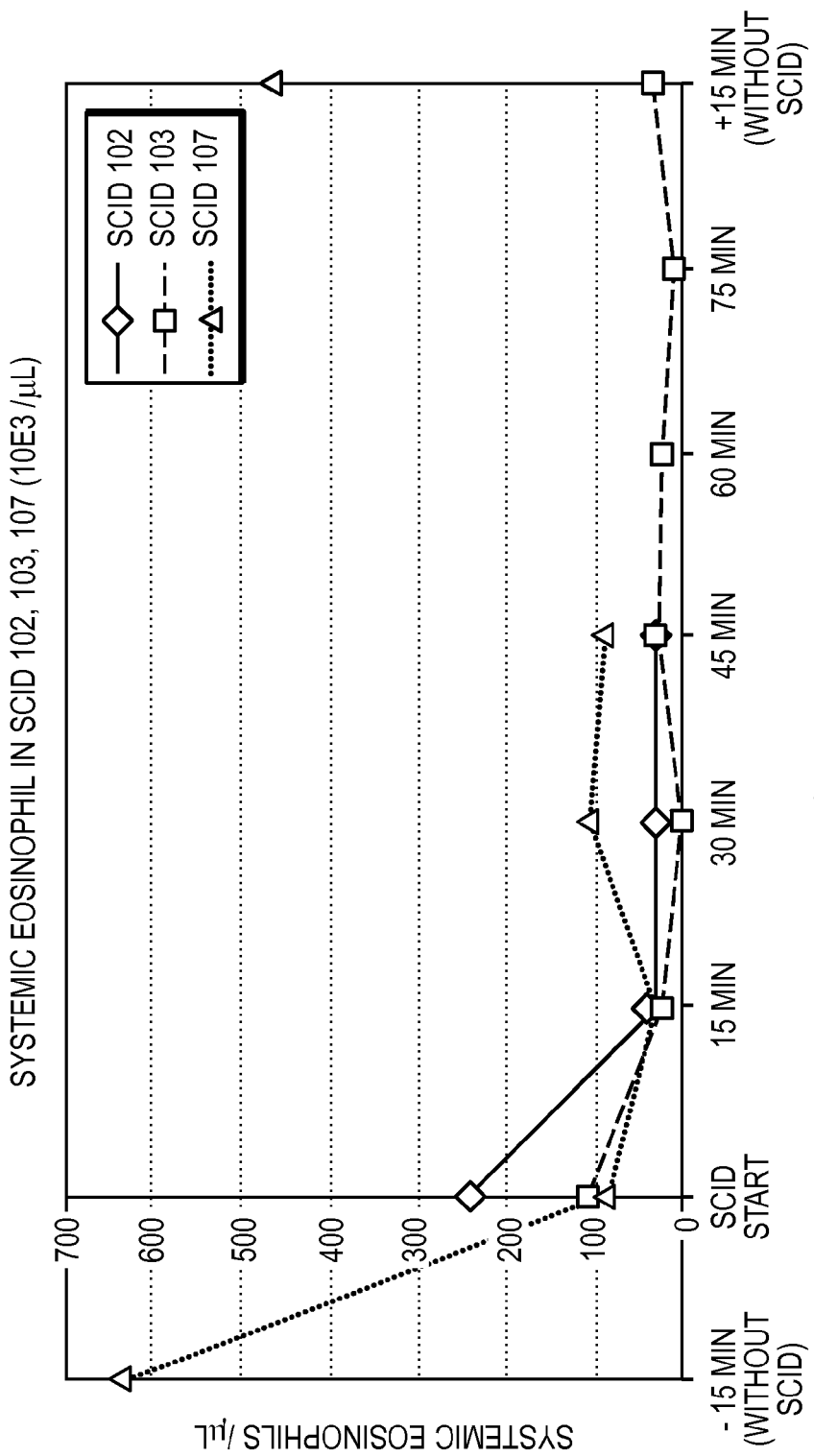
Figure 22F:
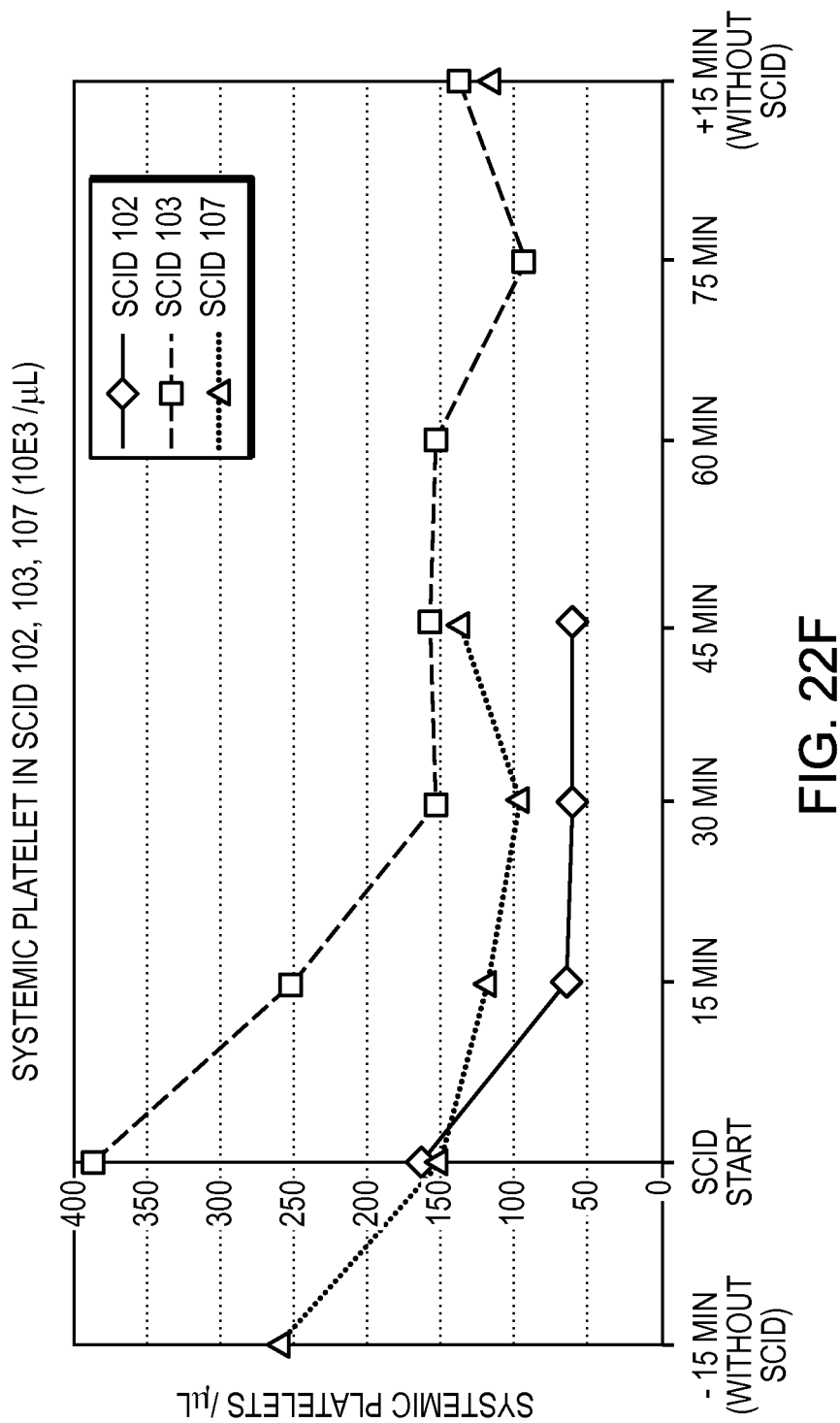

Surgery details and results. For SCID 102, the circuit was set up as in FIG. 4B, with an F40 cartridge (Fresenius Medical Care, Germany) as the SCID in the circuit. As shown in FIGS. 22A-22F, declines were observed in leukocyte and platelet counts. As shown in FIG. 22E, there was a decline in eosinophil count, which may be important in acute lung injury.

For SCID 103, the circuit was set up as in FIG. 4B, with a HPH 1000 Hemoconcentrator (Minntech Therapeutic Technologies, Minneapolis, Minn.) as the SCID in the circuit. SCID treatment lasted 75 minutes, and an additional sample was taken 15 minutes following the end of SCID treatment. As shown in FIGS. 22A-22E, time-dependent declines in leukocytes were observed. The SCID was disconnected at 75 minutes with a dramatic rebound in neutrophils within 15 minutes. No clotting was observed.

For SCID 107, the circuit was set up as in FIG. 4C, with HPH 1000 Hemoconcentrators (Minntech Therapeutic Technologies, Minneapolis, Minn.) used as each of the SCID and the hemofilter/hemoconcentrator in the circuit. CPB was initiated 15 minutes before the SCID was incorporated and SCID treatment lasted 45 minutes. An additional sample was taken 15 minutes following the end of SCID treatment. As shown in FIGS. 22A-22F, leukocyte and platelet numbers declined before incorporation of the SCID into the circuit, and except for monocytes, declined further with introduction of the SCID. In this surgery, pressure profiles were obtained and a UF flow of 50 mL/minute was demonstrated.

Figure 23A:
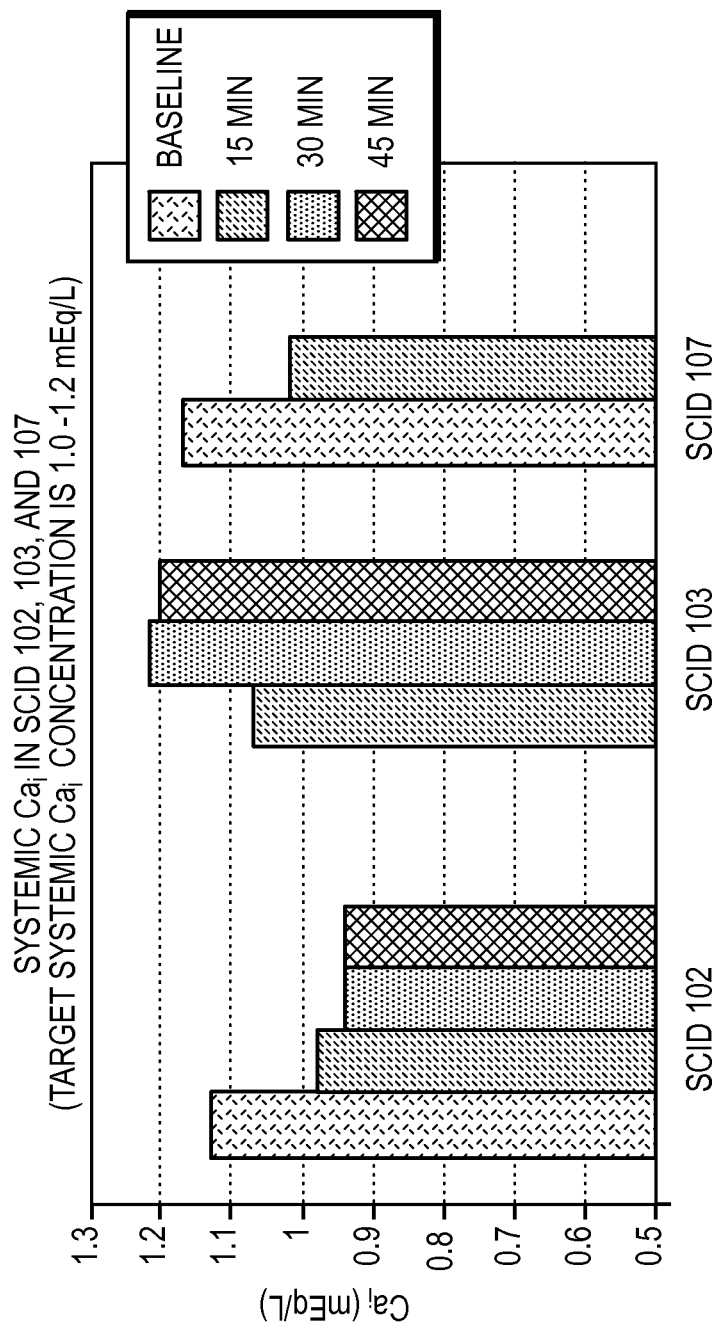
FIGS. 23A and 23B are graphs showing systemic and circuit $Ca_i$, respectively, in animals subjected to cardiopulmonary bypass surgery and treated with a system of the present invention that included a SCID and citrate.
Figure 23B:
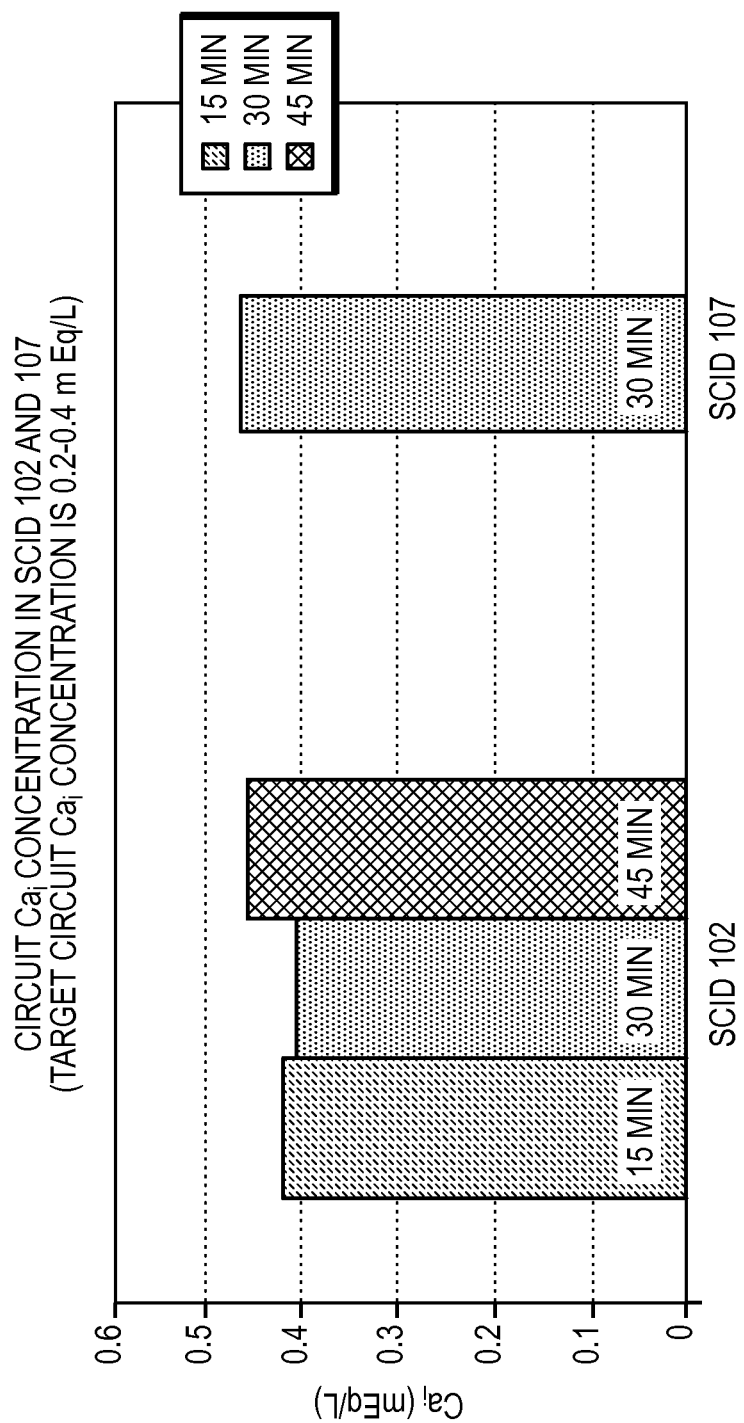

As shown in FIGS. 23A and 23B, systemic $Ca_i$ was maintained, and the SCID circuit $Ca_i$ was in the target range. Of general note from these surgeries, no ultrafiltrate (UF) was observed with lower SCID pressures.

Conclusion

The experiments described in this Example suggest that incorporation of a SCID device into an extracorporeal circuit, such as a CPB circuit, can sequester leukocytes and platelets and enhance the likelihood of a successful clinical outcome during surgery.

Example 9

Treatment of Inflammation Associated with Cardiopulmonary Bypass-Induced Acute Lung Injury (ALI) and Acute Kidney Injury (AKI) in an Animal Model As an extension of the experiments described in Example 8, the experiments described in this Example are designed to show efficacy of a device of the present invention to sequester leukocytes and inhibit their inflammatory action in the treatment of CPB-induced ALI and AKI.

Specifically, the aim of this Example entails optimizing a SCID protocol that effectively treats CPB-induced ALI or AKI. To achieve this goal, animals can be treated with any of the CPB circuits described in FIG. 4B, 4C, 4E, or 4F, each of which includes a SCID and citrate feed. Alternatively, CPB circuits described in FIG. 4A or 4D can be tested, each of which includes a SCID without citrate infusion. Moreover, a SCID used during CPB can be replaced with a fresh SCID while the treatment is occurring, and/or one or more SCIDs can be placed in series or in parallel in the "SCID" location of any of FIGS. 4A-4F.

A variety of porcine models have been reported in the literature to assess the mechanisms and therapeutic interventions of CPB-induced ALI. For example, it has been demonstrated in prior porcine models that demonstrable ALI can be incrementally induced with additive insults, which include the following: (1) the length of time for CPB from 60 to 120 minutes; (2) aortic cross clamping and cardiac cold cardioplegia producing ischemia/reperfusion injury; (3) cardiotomy suction with open reservoirs promoting activation of blood elements (leukocytes, platelets, and complement); and (4) endotoxin infusion post CPB promoting a SIRS response similar to that observed in patients due to detectable levels of endotoxin post CPB, presumably due to gastrointestinal barrier dysfunction following cardiac surgery and mild ischemia/reperfusion injury.

An established porcine protocol of CPB-induced ALI with significant changes in pulmonary function and molecular markers in bronchoalveolar (BAL) fluid within 3.5 hours following CPB and 2 hours post sequential lipopolysaccharide (LPS; 1 µg/kg over 60 minutes) has been reported. This reported protocol uses a femoral-femoral hypothermic bypass procedure followed by a 60-minute LPS infusion beginning 30 minutes after CPB was discontinued. Lung parameters were measured up to 2 hours following these sequential insults, with significant injury parameters observed. Other protocols could be developed to produce measurable ALI in 4 hours while being more reflective of clinical practice with CPB.

This example will use a clinically relevant model of ALI and AKI utilizing 60 minutes of CPB, aortic cross clamping and cardiac hypothermic cardioplegia as the baseline protocol, along with cardiotomy and cardiac suctioning during CPB into an open venous reservoir to promote incremental insults. If this is not sufficient to cause measurable ALI and AKI, then a 30-60-minute infusion of *E. Coli* LPS (0.5-1.0 µg/kg) beginning 30 minutes following completion of CPB will be added. The general approach to this CPB porcine model is detailed below.

CPB Protocol

In one exemplary protocol, Yorkshire pigs (30-35 kg) are premedicated with 1M atropine (0.04 mg/kg), azaperone (4 mg/kg), and ketamine (25 mg/kg), and then anesthetized with 5 µg/kg of fentanyl and 5 mg/kg of thiopental. After intubation with an 8-mm endotracheal tube (Mallinckrodt Company, Mexico City, Mexico), the pigs are placed in the supine position. Anesthesia is maintained by continuous infusion of 5 mg/kg/hour of thiopental and 20 µg/kg/hour of fentanyl. Muscle relaxation is induced with 0.2 mg/kg of pancuronium followed by intermittent reinjections of 0.1 mg/kg to achieve optimal surgical and ventilatory conditions.

Ventilation is established using a volume cycle ventilator at 10 mL/kg total volume and an inspired oxygen fraction of 1 with no positive end expiratory pressure. Polyethylene monitoring lines are placed in the external jugular vein and the femoral artery and vein. Esophageal and rectal temperature probes are inserted. Median sternotomy is performed. A 16 or 20 mm Transonic perivascular flow probe is placed on the main pulmonary artery, and Millar microtip pressure transducers are placed in the pulmonary artery and left atrium. Prior to initiating CPB, baseline pulmonary artery pressure and flow rate and left atrial pressure readings are taken for determination of cardiac output. After systemic heparinization (300 U/kg), an 18F Medtronic DLP arterial cannula is placed in the ascending aorta and a 24F Medtronic DLP single-stage venous cannula is placed in the right atrium.

The CPB circuit is primed with 1,000 mL of lactated Ringer's solution and 25 mEq of $NaHCO_3$. The circuit consists of a Medtronic Biomedicus Centrifugal blood pump, a Medtronic Affinity hollow fiber oxygenator with integral heat exchanger, and a cardiotomy reservoir. A Medtronic Affinity 38-µm filter is placed in the arterial limb to capture particulate debris. The left ventricle is vented using a 12-Ga Medtronic standard aortic root cannula with vent line connected to a Sarns roller pump and the cardiotomy reservoir. Scavenged blood is salvaged with a cardiotomy suction catheter, also connected to the Sarns roller pump and the cardiotomy reservoir. Cardiopulmonary bypass is initiated, ventilation is discontinued, and systemic perfusion maintained at 2.4 $L/min/m^2$ body surface area. Moderate perfusion hypothermia (32° C. rectal temperature) is used, and mean aortic pressure kept at 60-80 mmHg by modification of flow and intravenous phenylephrine infusion (0-2 µg/kg/min). The ascending aorta is cross clamped, and cardioplegia is delivered into the aortic root cannula at 7 degrees, consisting of the University of Michigan standard cardioplegia solution diluted with blood at a 4:1 ratio. The solution consists of citrate phosphate and dextrose (CPD), tromethamine, and potassium chloride. A total dose of 1 L of cardioplegia is delivered, and 500 mL is repeated every 20 minutes. Systemic rewarming is started after 40 minutes, and extracorporeal circulation discontinued after 60 minutes (clamping time 45 minutes). Prior to weaning from CPB, the lungs are inflated to 30-cm $H_2O$ airway pressure for 10 seconds for three breaths, and the mechanical ventilation is resumed using the same ventilator settings. During weaning from CPB, an infusion of epinephrine (0-1 µg/kg/minute) is titrated to maintain aortic blood pressure within normal ranges. Within 30 minutes of discontinuation of extracorporeal circulation, the blood in the oxygenator is transferred back into the circulation, heparin is reversed by protamine (1 mg for 100 U heparin) and normothermic rectal temperature achieved. Physiologic measurements are recorded before and during CPB and for 4 hours after CPB.

Extracorporeal Circuit

With a porcine model of CPB with substantive changes reflective of ALI and AKI, the influence of the SCID in ameliorating organ injury can be directly tested. A single-cartridge SCID will be placed in a parallel circuit after the membrane oxygenator (as shown, for example, in FIG. 4F). It is contemplated that the membrane oxygenator will activate circulating leukocytes, which are then sequestered in the SCID. Citrate will be added to the regional SCID parallel blood circuit to lower blood ionized $Ca_i$ to target levels, for example, about 0.2 to about 0.4 mM, with $Ca^{2+}$ reinfusion at the end of the parallel circuit. Two groups of animals will be evaluated and compared. The first group will receive SCID and heparin anticoagulation, and the second group will receive SCID and citrate anticoagulation. Each group will have six animals, with initial analysis of the two groups after 3 animals from each group have been treated. Regional citrate anticoagulation will be achieved utilizing standard practice solutions and clinical protocols. Citrate acts as an anticoagulation agent by binding with calcium. The bound calcium is then unavailable to trigger clotting factors. Calcium is added to the bloodstream just before the blood is returned to the animal in order to restore systemic $Ca_i$ levels that will allow adequate coagulation and cardiac function.

The current standard protocol used for continuous renal replacement therapy for citrate anticoagulation will be used. The ACD-A citrate IV solution (Baxter Healthcare) will be connected to a citrate infusion pump and the line to the SCID blood infusion port prior to the SCID. Calcium will be administered into the returned blood after the SCID via an infusion port to restore systemic calcium. Citrate infusion fluid rate (mL/hour) will be 1.5 times the blood flow rate (mL/minute) to achieve an $Ca_i$ level pre-cartridge between 0.2 and 0.4 mmol/L.

The SCID blood flow rate is targeted to be 200 mL/minute and will be controlled with a pump placed in the blood circuit pre-SCID set at a flow rate of 200 mL/minute. Calcium chloride (20 mg/mL, 0.9% N.S.) will be infused into the blood line post-SCID to achieve an $Ca_i$ level in the system (animal bloodstream values) between 0.9 and 1.2 mmol/L. Initial $Ca^{2+}$ infusion rate is 10% of the citrate infusion rate. $Ca_i$ levels will be evaluated in the arterial end of the CPB circuit prior to the pump system to reflect systemic $Ca_i$ levels and in the venous end of the SCID parallel circuit. All $Ca_i$ will be measured with an i-STAT® diagnostic device (Abbott Labs).

Measurement of Acute Lung Injury (ALI)

Pulmonary function. ALI following CPB results in increases in alveolar-arterial oxygenation gradients, intrapulmonary shunt fraction, pulmonary compliance and pulmonary vascular resistance. These parameters will be measured every 30 minutes during the 4 hour post-CPB period.

Lung Tissue analysis. ALI in the post-pump syndrome is associated with neutrophil accumulation in the lung and increases in interstitial fluid. Neutrophil aggregation will be assessed at the end of the research protocol by obtaining lung tissue from a segment not used for BAL. Samples of tissue will be used for myeloperoxidase tissue activity reflective of tissue neutrophil infiltration, histologic processing for semi-quantitative neutrophil counts, and water weight in lung tissue, with the difference in weights prior to and after desiccation and expressed as percent of wet weight [(wet weight−dry weight)/wet weight].

BAL fluid analysis. BAL fluid is obtained by cannulation of the right middle lobe of the lung with three successive infusions of 20 mL of normal saline and gentle aspiration. The fluid is evaluated for protein content (reflective of microvascular injury) and cytokine concentration (IL-1, IL-6, IL-8, IL-10, IFN-γ, and TNF-α). Cell counts in the BAL fluid are determined after a cytospin with cytology staining to provide the total and percentage of various cell components, including epithelial, neutrophil, and macrophage/monocyte. Alveolar macrophages will be isolated, incubated overnight and their cytokine response to LPS evaluated the next day. Fluid levels of matrix-metalloproteinase-2 and -9, elastase, and myeloperoxidase are measured with well-established assays as a reflection of activated neutrophil-secreted products important in developing tissue injury.

Measurement of Acute Kidney Injury (AKI)

Recent clinical data have clearly demonstrated that neutrophil gelatinase-associated lipocalin (NGAL) is an early biomarker for AKI following CPB. The amount of NGAL in the urine and serum at 2 hours following CPB is a highly specific and sensitive predictive marker of AKI with subsequent increases in serum creatinine and BUN. Serum and urine will be collected at baseline, time of CPB discontinuance and q one hour after CPB in all animals. NGAL levels will be determined by a sensitive ELISA assay for pig. Differences in NGAL levels should reflect the degree of AKI in this animal model.

Serum chemistries will be measured with an automated chemical analyzer. Cytokine levels will be measured with commercial ELISA assay kits reactive to porcine cytokines: IL-1, IL-6, IL-8, IL-10, IFN-γ and TNF-α (R & D Systems).

BAL fluid will be obtained for cell counts and cell-type distribution, protein as a measure of vascular leak, and cytokine levels, including IL-1, IL-6, IL-8, IL-10, IFN-γ and TNF-α

Cardiovascular and biochemical data will be analyzed by repeated-measures analysis of variance (ANOVA). Plasma levels of various moieties, and survival times will be compared utilizing Student's T-test, paired or non-paired as appropriate.

It is contemplated that animals receiving citrate regional anticoagulation in the CPB system that includes a SCID will have less pulmonary dysfunction, lung inflammation, and AKI as measured with NGAL. It is also contemplated that the degree of systemic WBC count with neutropenia and leukopenia will nadir at 3 hours but be of the same magnitude in both groups. It is also contemplated that the release of leukocytic inflammatory indices will be inhibited in the citrate versus heparin groups.

INCORPORATION BY REFERENCE

The entire disclosure of each of the publications and patent documents referred to herein is incorporated by reference in its entirety for all purposes to the same extent as if each individual publication or patent document were so individually denoted.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. A system for treating primed or activated leukocytes from a subject in need thereof, the system comprising:
a device defining a passageway that permits body fluid from the subject to pass therethrough, the passageway comprising a region configured to bind the primed or activated leukocytes; and
a calcium chelating agent capable of inhibiting release of a pro-inflammatory substance from the primed or activated leukocytes or deactivating the primed or activated leukocytes.

2. The system of claim 1, further comprising a second device in series with the device defining the passageway.

3. The system of claim 1, wherein the agent is associated with a surface of the passageway.

4. The system of claim 1, wherein the agent is infused into the passageway.

5. The system of claim 1, wherein the calcium chelating agent comprises citrate.

6. The system of claim 1, wherein the calcium chelating agent is one or more of citrate, sodium hexametaphosphate, ethylene diamine tetra-acetic acid (EDTA), triethylene tetramine, diethylene triamine, o-phenanthroline, and oxalic acid.

7. The system of claim 1, wherein the region configured to bind the leukocytes comprises a membrane.

8. The system of claim 7, wherein the membrane is porous.

9. The system of claim 7, wherein the membrane has a surface area greater than about 0.2 $m^2$.

10. The system of claim 7, wherein the membrane permits the passage of fluid therethrough.

11. The system of claim 7, wherein the surface of the membrane binds the leukocytes.

12. The system of claim 1, wherein the region configured to bind the leukocytes is configured such that shear force within the region is less than about 1000 dynes/$cm^2$ when fluid passes through the passageway at a rate of from about 100 mL/minute to about 500 mL/minute.

13. The system of claim 12, wherein the region configured to bind leukocytes is configured such that shear force within the region is less than about 100 dynes/$cm^2$ when fluid passes through the passageway at a rate of from about 100 mL/minute.

14. The system of claim 1, wherein the region configured to bind the leukocytes comprises a cell-adhesion molecule.

15. The system of claim 1, wherein the region is defined by the surface of a fiber or plurality of fibers.

16. The system of claim 15, wherein the device comprises a housing and a fiber or a plurality of fibers disposed therein, wherein each fiber has an exterior surface that binds the leukocytes.

17. The system of claim 16, wherein the passageway is formed by the space surrounding the fiber or fibers within the housing.

18. The system of claim 16, wherein the exterior surface of the fiber binds the leukocytes.

19. The system of claim 15, wherein the fiber is, or plurality of fibers are, hollow.

20. The system of claim 1, wherein the subject has an inflammatory condition selected from the group consisting of systemic inflammatory response syndrome (SIRS); cardiopulmonary bypass syndrome; acute respiratory distress syndrome (ARDS); sepsis; rheumatoid arthritis; systemic lupus erythematosis, inflammatory bowel disease; multiple sclerosis; psoriasis; allograft rejection; asthma; acute renal failure; chronic renal failure; cardiorenal syndrome; hepatorenal syndrome; acute organ failure from ischemic reperfusion injury to myocardium, central nervous system, liver, kidney, or pancreas; and an inflammatory condition associated with end-stage renal disease or a cardiopulmonary-bypass procedure.

21. The system of claim 1, wherein the subject has sepsis.

22. The system of claim 1, wherein the subject has acute renal failure or end-stage renal disease.

23. The system of claim 1, wherein the subject has an inflammatory condition associated with a cardio-pulmonary bypass procedure.

24. The system of claim 1, wherein the device has an outlet configured to return leukocytes to the subject.

25. The system of claim 1, wherein the device is cell-free.

26. The system of claim 1, wherein the device is configured to bind the leukocytes for a time sufficient to permit the subsequent inhibition or release of a pro-inflammatory substance from the leukocytes and/or deactivation of the leukocytes.

27. The system of claim 1, wherein a surface of the passageway binds the leukocytes.

* * * * *